(12) United States Patent
Toyoda et al.

(10) Patent No.: US 7,921,105 B2
(45) Date of Patent: Apr. 5, 2011

(54) BIOITEM SEARCHER, BIOITEM SEARCH TERMINAL, BIOITEM SEARCH METHOD, AND PROGRAM

(75) Inventors: Tetsuro Toyoda, Yokohama (JP); Norio Kobayashi, Yokohama (JP); Yoshiki Mochizuki, Yokohama (JP)

(73) Assignee: Riken, Wako-shi (JP)

( * ) Notice: Subject to any disclaimer, the term of this patent is extended or adjusted under 35 U.S.C. 154(b) by 274 days.

(21) Appl. No.: 11/992,492

(22) PCT Filed: Apr. 27, 2007

(86) PCT No.: PCT/JP2007/059268
§ 371 (c)(1),
(2), (4) Date: May 19, 2008

(87) PCT Pub. No.: WO2007/126088
PCT Pub. Date: Nov. 8, 2007

(65) Prior Publication Data
US 2009/0112850 A1    Apr. 30, 2009

(30) Foreign Application Priority Data

Apr. 28, 2006   (JP) .................................. 2006-125786

(51) Int. Cl.
G06F 7/00 (2006.01)
G06F 17/30 (2006.01)
(52) U.S. Cl. ..................... 707/722; 707/730; 707/941
(58) Field of Classification Search ............ 707/999.001–999.005, 722, 730, 707/941

See application file for complete search history.

(56) References Cited

U.S. PATENT DOCUMENTS
2002/0004792 A1   1/2002   Busa
(Continued)

FOREIGN PATENT DOCUMENTS
JP   8-30629 A   2/1996
(Continued)

OTHER PUBLICATIONS

H. Tsujimoto et al., "Parallel Keyword Recommendation System and its application to Genome Database," Annual Conference of JSAI, Japanese Society of Artificial Intelligence, 2000, pp. 168-170.

(Continued)

*Primary Examiner* — Mohammad Ali
*Assistant Examiner* — Kannan Shanmugasundaram
(74) *Attorney, Agent, or Firm* — Foley & Lardner LLP

(57) ABSTRACT

According to one aspect of the present invention, a bio-item searching apparatus searches for a target bio-item with a keyword input by a user. In the bio-item searching apparatus, the storage device stores a bio-item literature set having a literature in which the bio-item name is described for each of bio-items. The control device searches each of the bio-item literature sets with the keyword to acquire the number (Nh) of literatures including the keyword for each of the bio-items, selects the bio-item in which the number-of-literatures Nh is 1 or larger as a candidate bio-item, creates, for each of the candidate bio-items, a number-of-literatures table constituted by any one or both of a) the number-of-literatures Nh, and b) the number of literatures each not including the keyword and including the bio-item name (the number of literatures in the bio-item literature set of the bio-item—Nh), calculates a correlation score between the bio-item and the keyword based on statistical calculation by using the number-of-literatures table for each of the candidate bio-items, and outputs the candidate bio-items to the output device based on the correlation score.

15 Claims, 32 Drawing Sheets

U.S. PATENT DOCUMENTS

| | | | |
|---|---|---|---|
| 2002/0133498 A1* | 9/2002 | Keefer et al. | 707/100 |
| 2003/0175722 A1* | 9/2003 | Mann et al. | 435/6 |
| 2003/0220910 A1* | 11/2003 | Kincaid | 707/3 |
| 2003/0225773 A1* | 12/2003 | Jenssen et al. | 707/100 |
| 2005/0160082 A1* | 7/2005 | Dawson | 707/3 |
| 2005/0197783 A1* | 9/2005 | Kuchinsky et al. | 707/1 |
| 2005/0240583 A1 | 10/2005 | Li et al. | |
| 2005/0251514 A1 | 11/2005 | Houle | |

FOREIGN PATENT DOCUMENTS

| | | |
|---|---|---|
| JP | 10-149376 A | 6/1998 |
| JP | 2001-290822 A | 10/2001 |
| JP | 2003-044481 A | 2/2003 |
| JP | 2003-141123 A | 5/2003 |
| JP | 2005-301786 A | 10/2005 |
| JP | 2006-72671 A | 3/2006 |
| WO | WO 2004/027706 A1 | 4/2004 |

OTHER PUBLICATIONS

A. Takano et al., "Development of the generic association engine for processing large corpora," 2002, retrieval date Jul. 24, 2007, Internet <URL http://geta.ex.nii.ac.jp/pdf/itx2002.pdf>.

C. Von Mering et al., "STRING: known and predicted protein—protein associations, integrated and transferred across organisms", *Nucleic Acids Research*, vol. 33, 2005, pp. D433-D437.

B. Alako et al., "CoPub Mapper: mining MEDLINE based on search term co-publication", *BioMed Central*, vol. 6, No. 1, 2005, pp. 1-15.

* cited by examiner

FIG.2

|  | KEYWORD INCLUDED | KEYWORD NOT INCLUDED |
|---|---|---|
| BIO-ITEM INCLUDED | a | b |
| BIO-ITEM NOT INCLUDED | c | d |

FIG.3

|  | KEYWORD IS INCLUDED | KEYWORD IS NOT INCLUDED |
|---|---|---|
| BIO-ITEM QUERY 1 IS SATISFIED | Nh | Ng-Nh |
| BIO-ITEM QUERY 1 IS NOT SATISFIED | Nk-Nh | Nall-Nk+Nh-Ng |

|  | | BIO-ITEM 1 | |
|---|---|---|---|
|  | | INCLUDED | NOT INCLUDED |
| BIO-ITEM 2 | INCLUDED | a | b |
|  | NOT INCLUDED | c | d |

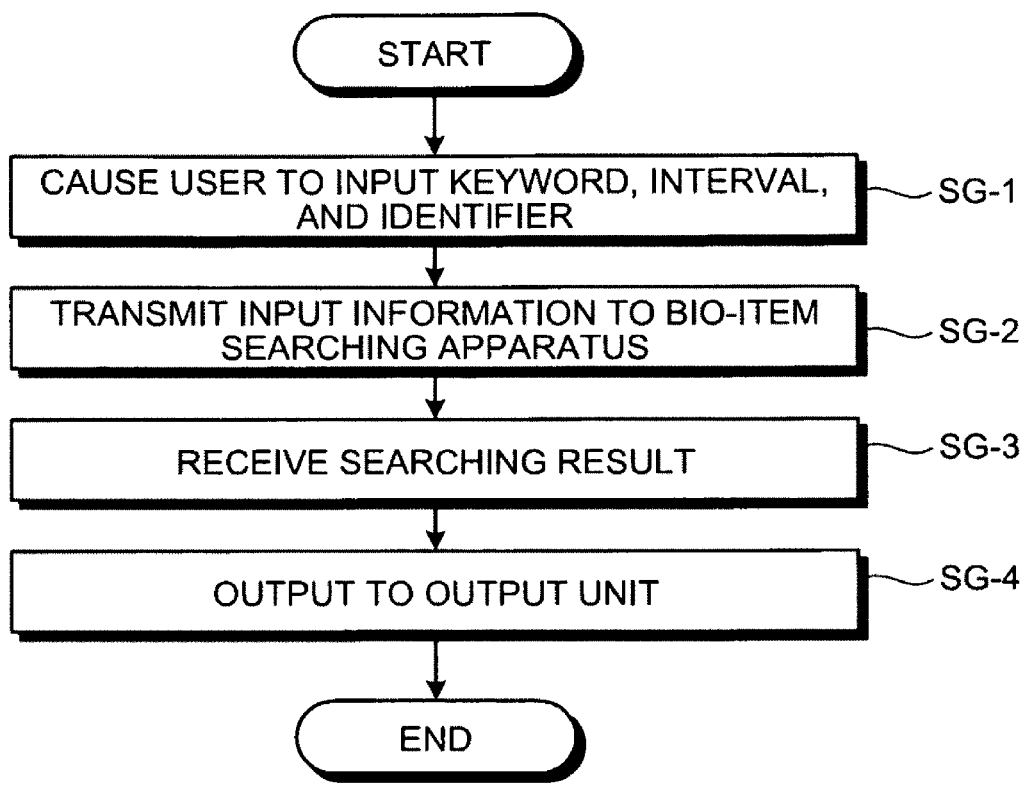

BIOITEM SEARCHER, BIOITEM SEARCH TERMINAL, BIOITEM SEARCH METHOD, AND PROGRAM

TECHNICAL FIELD

The present invention relates to a bio-item searching apparatus that prioritizes and searches for "bio-items" such as a gene, a polymorphism, an affection, a medical agent, a bio-resource, a protein, a person, a group, an organization, a compound, a technical term, and a literature folder, and information related to the bio-items in an information processing field such as biology (including genetics, epidemiology and system biology), chemistry, and the like which requires information search.

BACKGROUND ART

In an existing software system which searches a literature set with a keyword specified by a user to acquires a bio-item (hereinafter, a gene will be taken as an example) related to the keyword from the searching result, a method of calculating correlation scores between literatures and the keyword, ranking the literatures, and then displaying gene-related terms described in the literatures is used.

As a method for finding a promising gene closely related to the keyword, Patent Document 1 discloses a method for estimating a gene correlation from timings of expression of the genes. Patent Document 2 discloses an apparatus that performs link-searching for searching for objects connecting end-point keys, prioritizes the genes, takes in and searches for promising genes in a plurality of genes, and shows the promising genes with priorities.

Patent Documents 3 to 5 disclose methods for grouping keywords and searching for related keywords to make it easy to select keywords. More specifically, Patent Document 3 discloses an apparatus that searches with a keyword and keywords related to the keyword simultaneously and groups related keywords. Patent Document 4 discloses grouping of keyword. Patent Document 5 discloses an apparatus that extracts proven design data from a plurality of pieces of design data and evaluates design data by a statistic process.

A Generic Engine for Transposable Association (GETA) described in Nonpatent Literature 1 (accomplishment report in 2001) discloses a tool that rapidly calculates a similarity between rows or between columns (more specifically, between documents or between words) by an inner product measure in a large-scale and rough matrix typified by frequency index data (data representing a frequency of appearance of a specific word in a specific document) in a document search.

Patent Document 1: JP-A-2003-141123
Patent Document 2: JP-A-2001-290822
Patent Document 3: JP-A-8-30629
Patent Document 4: JP-A-2006-72671
Patent Document 5: JP-A-10-149376
Nonpatent Literature 1: Akihiko TAKANO et al., "Development of the generic association engine for processing large corpora", [online], 2002, Akihiko TAKANO, [searched on 23 Mar. 2007], the Internet <URL:http://geta.ex.nii.ac.jp/pdf/itx2002.pdf>

DISCLOSURE OF INVENTION

Problem to be Solved by the Invention

A conventional method of searching a literature set with a keyword and extracting a gene included in the retrieved literature has a problem that a promising gene closely related to the keyword cannot be always extracted at a higher rank. The conventional method also has a problem that selection of a keyword is not easy and requires a skilled user.

In particular, the method of Patent Document 1 has an object to investigate a relation of gene regulation between related genes from gene expression timings. The method has a problem that timing data is required to be acquired by using such as a DNA micro-array to investigate the relation.

The method of Patent Document 2 has a problem that selection of the both end-point keys involves trial and error by a user, making selection of an appropriate keyword still difficult.

The apparatus or the method according to any one of Patent Documents 3 to 5 has a problem that a keyword is required to be set in advance for grouping, selection of a keyword to reach a target gene is difficult, and a setting of manual grouping is cumbersome.

The apparatus or the method according to any one of Patent Document 1 to 5 has a problem that a searching result cannot be narrowed down in consideration of a genome range of genes to solve a problem in positional cloning.

In general, there has been a problem that degree of relativity between a keyword input by a user and a gene cannot be evaluated by a statistical significance probability. In the conventional method of extracting a gene included in a literature retrieved by searching with a keyword in a literature set, the problem that a promising gene closely related to the keyword cannot be always extracted at a higher rank cannot be solved even by using the above methods and apparatuses.

When a similarity between a keyword and each bio-item name is to be calculated by using the GETA according to Nonpatent Literature 1, an arithmetic process between a matrix having the keywords in columns and documents of each literature in rows and a matrix having the bio-item names in columns and documents of each literature in rows must be performed. When this method is attempted to be applied when the number of literatures is ten million or larger, the arithmetic process between matrices each having rows the number of which is equal to the number of literatures must be repeated the number of times which is equal to the number of bio-item names each time searching is executed, and a huge amount of time is taken to perform the calculation process.

In the GETA according to Nonpatent Literature 1, in solving the problem in positional cloning, bio-items serving as searching results and related bio-items cannot be narrowed down by genome positions of these bio-items. Since the similarity calculated by the GETA does not express the degree of relativity by a significance probability, the similarity cannot be statistically interpreted, and comprehensive evaluation by integrating with another significance probability is not possible. The GETA cannot rapidly rank bio-items similar to a keyword and related bio-items related to the bio-items similar to the keyword based on a statistical significance probability. Furthermore, since a matrix handled by the GETA, in which each column corresponds to a word cannot be prepared as a matrix which has, as one column, a combination of bio-item names or a plurality of words such as a conditional expression obtained by combining keywords by a Boolean expression, an unnecessary time is taken to perform a calculating process. For this reason, a method that makes it possible to rapidly calculate a correlation score without performing an arithmetic process between matrices each having rows the number of which is equal to the number of literatures during searching is necessary. Furthermore, a method that makes it possible to calculate a significance probability which can be statistically interpreted as a correlation score is necessary.

Even when the apparatuses and the methods are used with respect to combination constituted by three components including a keyword input by a user, an arbitrary bio-item 1 and an arbitrary bio-item 2, a table (three-dimensional number-of-literatures table) constituted by the numbers of literatures classified into eight classification items classified by checking whether the keyword is included or not, whether the bio-item 1 is included or not, and whether the bio-item 2 is included or not, cannot be rapidly created.

These are examples of the problems to be solved by the present invention.

The present invention has been made in consideration of the above circumstances, and has as its objective to provide a bio-item searching apparatus, a bio-item searching terminal apparatus, a bio-item searching method, and a program that acquires the number of literatures related to a keyword in an entire literature set to calculate a correlation score between the keyword and bio-items by a statistical process and to make it possible to display a ranking or a related item without requiring a setting of grouping for prioritization or association over the keywords. The present invention has as its objective to provide a bio-item searching apparatus and a bio-item searching method and a program that searches for a gene related to a keyword by using a large-scale literature set and displays a target gene at a higher rank in solving a problem in positional cloning.

The present invention has as its objective to provide a bio-item searching apparatus, a bio-item searching terminal apparatus, a bio-item searching method, and a program that needs not take an excessive calculating process time in searching without performing an arithmetic process between matrices each having rows the number of which is equal to the number of literatures including a keyword. The present invention has as its objective to provide a bio-item searching apparatus, a bio-item searching method, and a program that can perform an evaluation by a statistical significance probability, perform a comprehensive evaluation by integrating with another significance probability, and rapidly perform ranking.

Means for Solving Problems

To solve the above problems and to achieve the above objectives, according to one aspect of the present invention, a bio-item searching apparatus that searches for a target bio-item with a keyword input by a user, includes a control device, a storage device, and an output device. The storage device includes a bio-item literature set storage unit that stores a bio-item literature set having a literature in which the bio-item name is described for each of bio-items. The control device includes a number-of-literatures acquiring unit that searches each of the bio-item literature sets with the keyword to acquire the number (Nh) of literatures including the keyword for each of the bio-items, a candidate bio-item selecting unit that selects the bio-item in which the number-of-literatures Nh is 1 or larger as a candidate bio-item, a table creating unit that creates, for each of the candidate bio-items, a number-of-literatures table constituted by any one or both of a) the number of literatures Nh, and b) the number of literatures each not including the keyword and including the bio-item name (the number of literatures in the bio-item literature set of the bio-item—Nh), a correlation score calculating unit that calculates a correlation score between the bio-item and the keyword based on statistical calculation by using the number-of-literatures table for each of the candidate bio-items, and an output unit that outputs the candidate bio-items to the output device based on the correlation score calculated by the correlation score calculating unit.

According to another aspect of the invention, in the bio-item searching apparatus, the storage device further includes an all-literature set storage unit that stores an all-literature set having all the literatures included in each of the bio-item literature sets, and the number-of-literatures acquiring unit further searches the all-literature set with the keyword to acquire the number (Nk) of literatures including the keyword, the table creating unit creates, for each of the candidate bio-items, the number-of-literatures table constituted by at least one of the a) the number-of-literatures Nh, the b) the number of literatures each not including the keyword and including the bio-item name (the number of literatures in the bio-item literature set of the bio-item—Nh), c) the number of literatures each including the keyword and not including the bio-item name (Nk−Nh), and d) the number of literatures each not including the keyword and not including the bio-item (the total number of literatures in the all-literature set—the number of literatures in the bio-item literature set—Nk+Nh).

According to still another aspect of the invention, in the bio-item searching apparatus, the storage device further includes a bio-item relation database that stores arbitrary two of the bio-items and a co-occurrence correlation score between the two bio-items in association with each other. The control device further includes a related bio-item extracting unit that extracts the bio-item having correlation with the candidate bio-item as a related bio-item based on the co-occurrence correlation score stored in the bio-item relation database, and an integrated correlation score calculating unit that calculates an integrated correlation score between the related bio-item and the keyword by integrating the correlation score of the candidate bio-item with the co-occurrence correlation score. The output unit outputs the related bio-item to the output device based on the integrated correlation score calculated by the integrated correlation score calculating unit.

According to still another aspect of the invention, in the bio-item searching apparatus, the control device includes a co-occurrence correlation score calculating unit that calculates, for each of the two arbitrary bio-items, the co-occurrence correlation score based on the statistical calculation by using a number-of-co-occurrence-literatures table constituted by at least one of i) the number of literatures each including the one bio-item name and including the other bio-item name, j) the number of literatures each not including the one bio-item name and including the other bio-item name, k) the number of literatures each including the one bio-item name and including the other bio-item name, and m) the number of literatures each not including the one bio-item name and not including the other bio-item name, which are acquired by searching the bio-item literature set of the one bio-item with the other bio-item name, and a bio-item relation database creating unit that stores the co-occurrence correlation score calculated by the co-occurrence correlation score calculating unit in the bio-item relation database in association with the two bio-items.

According to still another aspect of the invention, the bio-item searching apparatus, the integrated correlation score calculating unit integrates the integrated correlation score based on the following numerical expression 1 or an approximate expression of the numerical expression 1, $$P=1-(1-P1)(1-P2) \quad \text{(Numerical Expression 1)}$$

(where P is the integrated correlation score, P1 is the correlation score of the candidate bio-item, and P2 is the co-occurrence correlation score).

According to still another aspect of the invention, in the bio-item searching apparatus, the storage device further includes a position information database that stores genome position information representing a position on a genome chromosome corresponding to the bio-item in association with each other for each of the bio-items, and a region information storage unit that stores genome region information input by the user and indicating a genome region including a position on the genome chromosome corresponding to the target bio-item. The control device further includes a genome region determining unit that determines whether the position based on the genome position information corresponding to the candidate bio-item or the related bio-item, stored in the position information database is included in the genome region of the genome region information, and performs control to output the candidate bio-item or the related bio-item when it is determined that the position is included in the genome region.

According to still another aspect of the invention, in the bio-item searching apparatus, the storage device further includes an identifier information database that stores identifier information indicating an identifier corresponding to the bio-item in association with the bio-item for each of the bio-items, and a target bio-item identifier storage unit that stores the one piece of identifier information or the pieces of identifier information input by the user and corresponding to the target bio-item. The control device further includes an identifier determining unit that determines whether the identifier stored in the identifier information database and based on the identifier information of the bio-item is included in the one identifier or the plurality of identifiers of the identifier information stored in the target bio-item identifier storage unit for the candidate bio-item or the related bio-item, and performs control to output the candidate bio-item or the related bio-item when it is determined that the identifier is included in the one identifier or the plurality of identifiers.

According to still another aspect of the invention, the bio-item searching apparatus, the number-of-literatures acquiring unit searches, for arbitrary two of the candidate bio-items, the bio-item literature set of the one candidate bio-item to acquire the number (Ns) of literatures each including the other bio-item name and including the keyword, the table creating unit creates the three-dimensional number-of-literatures table based on the number-of-literatures Ns, the number-of-literatures tables related to the two candidate bio-items, and the number-of-co-occurrence-literatures table related to the two candidate bio-items, the correlation score calculating unit includes co-occurrence keyword correlated score calculating unit that calculates a co-occurrence keyword correlation score among the two candidate bio-items and the keyword based on the statistical calculation by using the three-dimensional number-of-literatures table, and the output unit outputs the co-occurrence keyword correlation score calculated by the co-occurrence keyword correlation score calculating unit to the output device in association with the two candidate bio-items.

According to still another aspect of the invention, in the bio-item searching apparatus, the co-occurrence keyword correlation score calculating unit, by using the three-dimensional number-of-literatures table, calculates a correlation score of the two candidate bio-items when the keyword is included as a keyword-included correlation score, calculates a correlation score of the two candidate bio-items when the keyword is not included as a keyword-not-included correlation score, and calculates any one of both the keyword-included correlation score and the keyword-not-included correlation score and a comparison result therebetween or both as the co-occurrence keyword correlation score.

According to still another aspect of the invention, in the bio-item searching apparatus, the statistical calculation calculates the correlation score based on a test.

According to still another aspect of the invention, in the bio-item searching apparatus, the statistical calculation uses a Fisher's exact test, a chi-square test, or a Bayes conditional probability.

According to still another aspect of the invention, in the bio-item searching apparatus, the output unit includes a searching result order output unit that ranks the candidate bio-item or the related bio-item to be output to the output device, based on the correlation score, the co-occurrence keyword correlation score, or the integrated correlation score.

According to still another aspect of the invention, in the bio-item searching apparatus, the bio-item name includes a concept word.

According to still another aspect of the invention, a bio-item searching terminal apparatus includes a control unit, an input unit, and an output unit connected to the bio-item searching apparatus. The control unit includes an input control unit that performs control to cause a user to input any one, two or all of the keyword, the genome region information and the identifier information through the input unit, a transmitting unit that transmits any one, two, or all of the keyword, the genome region information and the identifier information input by control of the input control unit to the bio-item searching apparatus, and a receiving output unit that receives and outputs the candidate bio-item, the related bio-item, or the co-occurrence keyword correlation score based on at least the keyword transmitted by the transmitting unit and output from the bio-item searching apparatus, to the output unit.

According to still another aspect of the invention, a bio-item searching method for searching for a target bio-item with a keyword input by a user, is executed by a bio-item searching apparatus comprising a control device, a storage device, and an output device. The storage device includes a bio-item literature set storage unit that stores a bio-item literature set having a literature in which the bio-item name is described for each of bio-items. The bio-item searching method includes searching each of the bio-item literature sets with the keyword to acquire the number (Nh) of literatures including the keyword for each of the bio-items, selecting the bio-item in which the number-of-literatures Nh is 1 or larger as a candidate bio-item, creating, for each of the candidate bio-items, a number-of-literatures table constituted by any one or both of a) the number-of-literatures Nh, and b) the number of literatures each not including the keyword and including the bio-item name (the number of literatures in the bio-item literature set of the bio-item—Nh), calculating a correlation score between the bio-item and the keyword based on statistical calculation by using the number-of-literatures table for each of the candidate bio-items, and outputting the candidate bio-items to the output device based on the correlation score calculated at the calculating, that are executed by the control device.

According to still another aspect of the invention, a computer program makes a bio-item searching apparatus execute a method for searching for a target bio-item with a keyword input by a user. The bio-item searching apparatus includes a control device, a storage device, and an output device. The storage device includes a bio-item literature set storage unit that stores a bio-item literature set having a literature in which the bio-item name is described for each of bio-items. The method includes searching each of the bio-item literature sets with the keyword to acquire the number (Nh) of literatures including the keyword for each of the bio-items, selecting the bio-item in which the number-of-literatures Nh is 1 or larger as a candidate bio-item, creating, for each of the candidate bio-items, a number-of-literatures table constituted by any one or both of a) the number-of-literatures Nh, and b) the number of literatures each not including the keyword and including the bio-item name (the number of literatures in the bio-item literature set of the bio-item—Nh), calculating a correlation score between the bio-item and the keyword based on statistical calculation by using the number-of-literatures table for each of the candidate bio-items, and outputting the candidate bio-items to the output device based on the correlation score calculated at the calculating, that are executed by the control device.

EFFECT OF THE INVENTION

A keyword for searching for a bio-item is limited to a phrase which specifies a bio-item such as a bio-item name (for example, a gene name, a disorder name, a protein name, a medical agent name, or the like) in a conventional method. However, in the present invention, a word or a phrase which is used in a description in a natural language such as a phenotype, a logical formula (AND, OR, NOT, or the like) of the word or the phrase, or an arbitrary keyword constituted by a wildcard ("*" expressing an arbitrary character string, "?" expressing an arbitrary one character, or the like) or the like can be used.

According to the present invention, when a document which describes a phenotype and a genotype of each patient in a searching study of a disorder-related polymorphism is used as each literature, and each genotype is used as each bio-item, a genotype which is most correlated with the phenotype can be rapidly searched for in an order of statistical significance probabilities by using a phrase related to the phenotype as a keyword.

According to the present invention, a statistical process based on the numbers of literatures related to the keyword and both the keyword and a bio-item (for example, a gene or the like) is performed to make it possible to rank a promising bio-item (for example, a gene) higher.

According to the present invention, ranking of bio-items is performed based on a correlation score to output the ranking (for example, display, printing, storing in a recording medium, or the like), so that a user may advantageously more precisely find a target bio-item.

According to the present invention, even when a bio-item related to a keyword is not present in a genome region (to be referred to as an "interval" hereinafter), i.e., when a searching result (answer by direct searching) of direct searching is not present, the related bio-item related to the bio-item and present in the interval can be inferred. In this manner, the inference of the bio-items is executed to calculate an answer by inference searching, so that a bio-item indirectly related to the keyword can also be searched for.

According to the present invention, by indirect searching (inference of a bio-item), a keyword to reach a target bio-item can be more flexibly selected.

According to the present invention, a user inputs a genome region (interval) information of the target bio-item to specify a position on a genome sequence. In extraction of a bio-item (for example, a gene or the like) present in the interval, even when a bio-item related to a keyword is not present in the interval, a gene which co-occurs with the above gene on a literature and is present in the interval can be advantageously acquired.

According to the present invention, a bio-item name includes a concept word to make it possible to improve more accurate detection precision.

According to the present invention, a literature set is searched for the number of literatures including a keyword input by the user to acquire the number of literatures, and a bio-item literature set is searched for the number of literatures including the keyword input by the user to acquire the number of literatures, and a correlation score is calculated from these scalars to make it possible to calculate the correlation score without an arithmetic process between matrices each having rows the number of which is equal to the number of literatures. Therefore, a processing time taken to search for a bio-item can be more shortened.

According to the present invention, even when a bio-item name is constituted by a combination of a plurality of words, only a literature including the bio-item is extracted as a bio-item literature set in advance, so that an unnecessary calculating process time is not required during searching.

According to the present invention, degree of relativity between a keyword input by a user and a bio-item (for example, a gene or the like) can be evaluated by a statistical significance probability, and the significance probability is integrated with another significance probability to make it possible to perform comprehensive evaluation. For this reason, reliability of a criterion used when the user selects a target bio-item can be more improved.

According to the present invention, since a bio-item related to the keyword and a related bio-item related to the bio-item related to the keyword can be rapidly ranked based on a statistical significant probability, the reliability of a criterion used when a user selects a target bio-item can be improved.

According to the present invention, even when there is no searching result (answer) of direct searching, for example, when a bio-item related to a keyword is not present in a bio-item group (to be referred to as a "group" hereinafter) specified by identifier information input by a user, a related bio-item which is related to the bio-item and present in the group can be inferred.

According to the present invention, with respect to three components including a keyword input by a user, one arbitrary bio-item, and another arbitrary bio-item, since a three-dimensional literature table (number-of-literatures three-dimensional table) constituted by the numbers-of-literatures classified into eight classification items classified by checking whether the keyword is included or not, whether the one bio-item is included or not, and whether the other bio-item is included or not, is rapidly created and a co-occurrence keyword correlation score is calculated to output by using the number-of-literatures three-dimensional table, a difference in degree of a co-occurrence relativity between the one bio-item and the other bio-item depending on the presence/absence of the keyword can be shown to the user.

BRIEF DESCRIPTION OF THE DRAWINGS

FIG. 2 is a diagram showing an example of a number-of-literatures table;

FIG. 3 is a diagram showing an example of a number-of-literatures table for correlation score calculation;

FIG. 9 is a diagram showing an example of a literature table for calculating a "keyword-included correlation score" and a "keyword-not-included correlation score";

FIG. 30 is a diagram showing an example which displays details of related literatures between a keyword "diabetes" and a mouse gene "Rrad";

FIG. 31 is a diagram showing an example which displays details of related literatures between a mouse gene "Insr" and a mouse gene "Irs1";

FIG. 35 is a flow chart showing an example of processes of the bio-item searching terminal apparatus 600.

Figure 1:
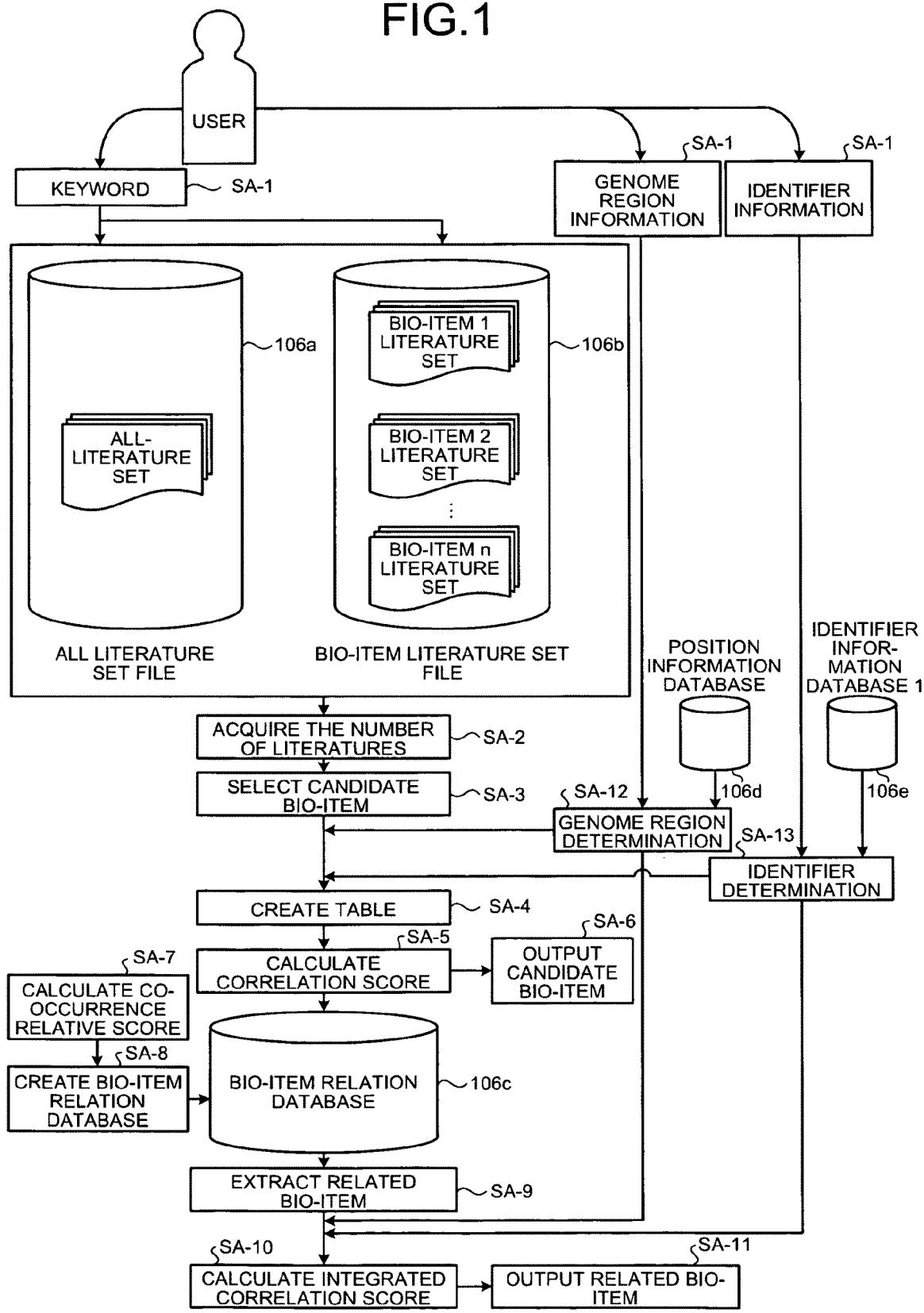
FIG. 1 is a principle block diagram showing a basic principle of the present invention.

EXPLANATIONS OF LETTERS OF NUMERALS 100 bio-item searching apparatus
102 control unit
102a number-of-literatures acquiring unit
102b candidate bio-item selecting unit
102c table creating unit
102d correlation score calculating unit
102e co-occurrence correlation score calculating unit
102f bio-item relation database creating unit
102g related bio-item extracting unit
102h integrated correlation score calculating unit
102i output unit
102j genome region determining unit
102k identifier determining unit
102m co-occurrence keyword correlation score calculating unit
102n search result order output unit
104 communication control interface unit
106 storage unit
106a all-literature set file
106b bio-item literature set file
106c bio-item relation database
106d position information database
106e identifier information database
108 input/output control interface unit
110 full text searcher
112 input device
114 output device
120 bio-item full text searcher
200 back-end
201 back-end management server
202 number-of-literatures acquiring server
203 interface
204 literature full text searcher
206d position information database
206c bio-item relation database
210 distributed literature searching server
211 interface
212 literature full text searcher
212i bio-item region determining unit
212d correlation score calculator
212e bio-item inferring unit
212f bio-item name table
250 external system
300 network
400 system management server
500 user client
600 bio-item searching terminal apparatus
602 control unit
602a input control unit
602b transmitting unit
602c receiving output unit 604 communication control interface unit
606 storage unit
608 input/output control interface unit
612 input unit
614 output unit

BEST MODES FOR CARRYING OUT THE INVENTION

Embodiments of a bio-item searching apparatus, a bio-item searching terminal apparatus, a bio-item searching method and a program according to the present invention will be explained in detail with reference to the accompanying drawings. The invention is not limited to the embodiments.

Outline of the Present Invention

An outline of the present invention will be explained with reference to FIGS. 1 to 3, and thereafter, the configuration, processes, and the like of the present invention will be explained in details. FIG. 1 is a principle block diagram showing a basic principle of the present invention. The present invention schematically has the following basic characteristics.

As an example, as shown in FIG. 1, the present bio-item searching apparatus searches for a target bio-item (for example, a gene, a polymorphism, an affection, a medical agent, a bio-resource, a literature folder, a protein, a person, a group, an organization, a compound, a technical term, and the like) with a keyword input by a user. The bio-item searching apparatus includes at least a control device, a storage device, and an output device. In this case, the "literature folder" is defined as a group of at least one literature. A folder which can store a file of document data on a computer is an example of the "literature folder". In this case, as a bio-item name of the literature folder, a folder name of the literature folder or a path name (an absolute path, a relative path, or Universal Resource Locator on the Internet) can be preferably used. A literature set having literatures included in the folder or having all literatures included in the literature holder and its subfolders can serve as a bio-item literature set of the bio-item.

The bio-item searching apparatus stores, for each bio-item, a bio-item literature set having a literature in which a bio-item name of the bio-item is described ("bio-item literature set file 106*b*" in FIG. 1). In this case, the bio-item searching apparatus may store an all-literature set having all literatures included in bio-item literature sets of bio-items 1 to n stored in the bio-item literature set files 106*b* ("all-literature set file 106*a*" in FIG. 1).

In this case, the "literature" means a set of document data which can be recorded in the storage device, and document data which can be specified by a file name or an identifier is one form of the literature. More specifically, records of a MEDLINE (Medical Literature Analysis and Retrieval System On-Line) database and an OMIM (Online Mendelian Inheritance in Man) database are an example of the literatures. Furthermore, when the document data is handled as a file, the document data and a file path name of the document data can serve as one literature. The "literature set" is data generated based on at least one literature and configured to make it possible to calculate, for an arbitrary keyword, the number of literatures in which the keyword is described. As an exemplary embodiment, the literature set is data which includes index information to make it possible to rapidly calculate the number of literatures for an arbitrary keyword. However, the present invention is not limited to the embodiment. The "bio-item name" is a name of a bio-item. In this case, the bio-item name may be constituted by a combination of a plurality of words or may include concept words.

As shown in FIG. 1, when the bio-item searching apparatus according to the present invention receives a keyword input by a user (SA-1), the bio-item searching apparatus searches with a keyword in each bio-item literature set stored in the bio-item literature set file 106*b* to acquire the number (Nh) of literatures each including the keyword in the bio-item literature set for each of bio-items 1 to n (SA-2). In this case, the bio-item searching apparatus may search with a keyword in all the literature sets stored in the all-literature set file 106*a* to acquire the number (Nk) of literatures each including the keyword in all the literature sets.

The bio-item searching apparatus selects a bio-item of a bio-item literature set in which the acquired number-of-literatures Nh is 1 or larger as a candidate bio-item (SA-3).

The bio-item searching apparatus creates a number-of-literatures table constituted by any one of a) the number-of-literatures Nh and b) the number of literatures including the bio-item name and not including the keyword (the number of literatures in a bio-item literature set of the bio-item—Nh) for each candidate bio-item (SA-4). In this case, the bio-item searching apparatus may create a number-of-literatures table constituted by at least one of the a), the b), c) the number of literatures including the keyword and not including the bio-item name (Nk–Nh), and d) the number of literatures not including the keyword and not including the bio-item name (the total number of literatures in the all-literature set—the number of literatures in the bio-item literature set—Nk+Nh). The "number-of-literatures table" will be explained below with reference to FIGS. 2 and 3. FIG. 2 is a diagram showing an example of the number-of-literatures table.

As shown in FIG. 2, the number-of-literatures table is constituted by at least one of the four items a) to d): a) the number of literatures each including the keyword and the candidate bio-item name, b) the number of literatures each not including the keyword and including the candidate bio-item name, c) the number of literatures each including the keyword and not including the candidate bio-item name, and d) the number of literatures each not including the keyword and not including the candidate bio-item name. An example of a method of storing the number of literatures in the number-of-literatures table to create the number-of-literatures table will be explained below with reference to FIG. 3. FIG. 3 is a diagram showing an example of a number-of-literatures table for correlation score calculation.

As shown in FIG. 3, an explanation will be made in association with the symbols used in the explanation in FIG. 2. The bio-item searching apparatus sets the number-of-literatures Nh as item a), (Ng–Nh) as item b), (Nk–Nh) as item c), and (Nall–Nk+Nh–Ng) as item d) to create a number-of-literatures table constituted by at least one of the four items a) to d). In this case, Ng denotes the number of literatures in a bio-item literature set of a corresponding bio-item, and Nall denotes the total number of literatures in the all-literature set stored in the all-literature set file 106*a*. In this case, as the literature table of the present invention, not only the one-dimensional or the two-dimensional literature table, but also a three-dimensional literature table may be used. An embodiment of the three-dimensional literature table will be explained below in detail.

Returning to FIG. 1, the bio-item searching apparatus calculates a correlation score between the candidate bio-item and the keyword for each candidate bio-item based on statistical calculation by using the created number-of-literatures table (SA-5). In this case, the statistical calculation may use a test such as a Fisher's exact test, a chi-square test, or a Bayes conditional probability. In this manner, a significance probability in the test is reflected on the correlation score between each candidate bio-item and the keyword to make it possible to calculate the correlation score which can be statistically interpreted. When the significance probability of the test is used as the correlation score, the correlation score decreases when the correlation becomes high. However, in contrast to this, the correlation score may be defined such that the correlation score increases when the correlation becomes high. In addition to this, as definition of the correlation score, a correlation score which is defined such that the correlation tends to be high when the item a) of the number-of-literatures table is large may be used, or a correlation score which is defined such that the correlation tends to be low when item b) of the number-of-literatures table is large may be used. A correlation score which is defined such that the correlation tends to be low when item c) of the number-of-literatures table is large may be used, and a correlation score which is defined from only item a) of the number-of-literatures table to satisfy the above tendencies. A correlation score defined from only item a) and item b) of the number-of-literatures table to satisfy the above tendencies may be used, and a correlation score which is defined from only item a) and item c) of the number-of-literatures table to satisfy the tendencies may be used. A correlation score which is defined from only item a), item b), and item c) of the number-of-literatures table to satisfy the tendencies may be used, and a correlation score which is defined from item a), item b), item c), and item d) of the number-of-literatures table to satisfy the tendencies may be used. When the definitions of the correlation scores are not based on all the values of item a), item b), item c), and item d) of the number-of-literatures table, an item which is not based on the definitions of the correlation scores need not be calculated. In addition, one correlation score defined based on at least two types of the correlation scores may be used as the correlation score.

Finally, the bio-item searching apparatus outputs the candidate bio-items to the output device based on the calculated correlation score (SA-6). In this case, the bio-item searching apparatus may rank the candidate bio-items and output the candidate bio-items to the output device.

Another aspect of the present invention will be explained below.

The bio-item searching apparatus according to another aspect of the present invention includes a bio-item relation database 106c that stores two arbitrary bio-items and a co-occurrence correlation score of the two bio-items in association with each other.

As an example of calculation of the co-occurrence correlation score, the bio-item searching apparatus uses a number-of-co-occurrence-literatures table constituted by at least one of i) the number of literatures each including one of the above two bio-item names and the other of the bio-item names, j) the number of literatures each not including one of the bio-item names and including the other of the bio-item names, k) the number of literatures each including one of the bio-item names and not including the other of the bio-item names, and m) the number of literatures each not including one of the bio-item names and not including the other of the bio-item names, obtained by searching for the other of the bio-items in a bio-item literature set of one of the bio-items, to calculate a co-occurrence correlation score based on statistical calculation (SA-7). The bio-item searching apparatus associates the calculated co-occurrence correlation score with the two bio-items, and stores the calculated co-occurrence correlation score in the bio-item relation database 106c (SA-8).

The bio-item searching apparatus according to another aspect of the present invention extracts a bio-item related to the selected candidate bio-item as a related bio-item based on the co-occurrence correlation score stored in the bio-item relation database 106c (SA-9).

The bio-item searching apparatus calculates an integrated correlation score between the related bio-item and the keyword by integrating the correlation score of the original candidate bio-item with the co-occurrence correlation score (SA-10).

In this case, the integrated correlation score may be calculated based on the following numerical expression 1:

$P=1-(1-P1)(1-P2)$ (Numerical Expression 1)

(where, P is an integrated correlation score, P1 is a correlation score of a candidate bio-item, and P2 is a co-occurrence correlation score).

In this case, as an approximate expression of the numerical expression 1, the following approximate expression (numerical expression 1-1) in which a product of P1 and P2 is regarded as 0 on the assumption that P1 or P2 is sufficiently smaller than 1.

$P=P1+P2$ (Numerical Expression 1-1)

When the numerical expression 1 is calculated while keeping logarithm, the following approximate expression (numerical expression 1-2) in which the numerical expression 1 is approximated such that the numerical expression 1 can be calculated by logarithm may be applied:

$\text{Log}(P)=\text{Max}\{\text{Log}(P1),\text{Log}(P2)\}$ (Numerical Expression 1-2)

(where Max{A,B} is a function of selecting not smaller one of A and B).

Finally, the bio-item searching apparatus outputs the related bio-item to the output device based on the calculated integrated correlation score (SA-11). This is the explanation of another aspect of the present invention.

In this case, the bio-item searching apparatus may store genome position information representing a position on a genome chromosome corresponding to a bio-item for each bio-item such that the genome position information is associated with each bio-item ("position information database 106d" in FIG. 1).

In this case, when a user inputs genome region information including a position on a genome chromosome corresponding to a target bio-item (SA-1), the bio-item searching apparatus determines, with respect to a candidate bio-item or a related bio-item, whether a position on the genome stored in the position information database 106d and corresponding to the bio-item is included in the genome region input by the user. When it is determined that the position is included in the genome region, the bio-item searching apparatus performs control to output the candidate bio-item or the related bio-item (SA-12).

In this case, the bio-item searching apparatus may store identifier information representing an identifier corresponding a bio-item such that the identifier information is associated with the bio-item for each bio-item ("identifier information database 106e" in FIG. 1).

In this case, when the user inputs one piece of identifier information or a plurality of pieces of identifier information corresponding to the target bio-item (SA-1), the bio-item searching apparatus determines, with respect to a candidate bio-item or a related bio-item, whether an identifier stored in the identifier information database 106e and based on identifier information corresponding to the bio-item is included in one identifier or a plurality of identifiers input by the user. When it is determined that the identifier is included in the one identifier or the identifiers, the bio-item searching apparatus performs control to output the candidate bio-item or the related bio-item (SA-13).

A program to transmit a keyword input by a user who operates a computer from the computer to the above control device of the bio-item searching apparatus through a network may be executed by the computer. Suitably, an HTML (Hyper Text Markup Language) file which can be interpreted by the web browser of the computer may be used as the program.

A bio-item searching terminal apparatus may be used as the computer. The bio-item searching terminal apparatus is connected to the bio-item searching apparatus through a network and includes at least a control unit, an input unit, and an output unit. The bio-item searching terminal apparatus may be designed to be controlled such that a user inputs a keyword, genome region information, or identifier information through the input unit, to transmit the keyword or the like to the bio-item searching apparatus 100, to receive a searching result (candidate bio-item, related bio-item, or co-occurrence keyword correlation score) output from the bio-item searching terminal apparatus 600, and to output the searching result to the output unit.

This is the outline of the present invention.

Configuration of Bio-item Searching Apparatus

Figure 4:
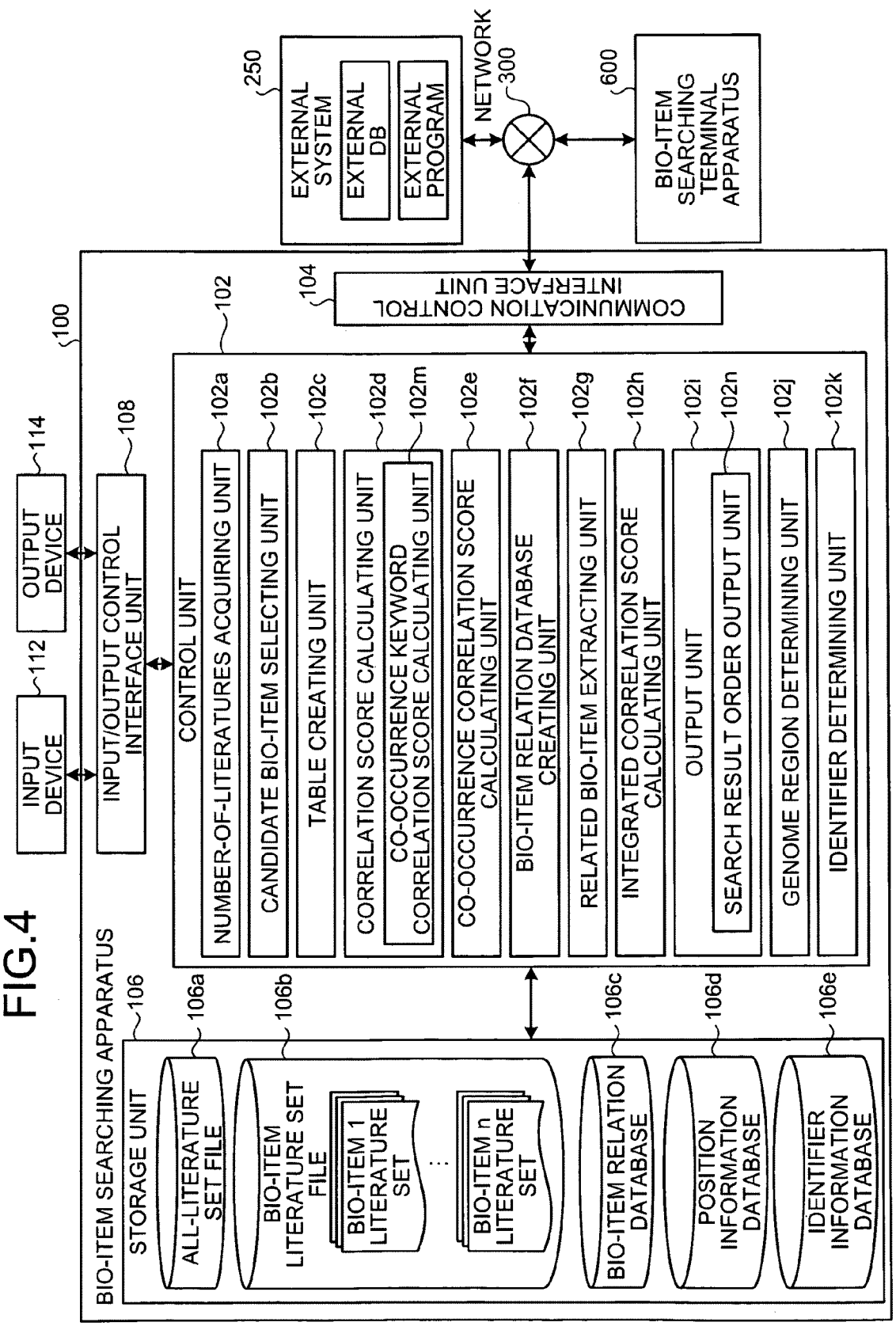
FIG. 4 is a block diagram showing an example of a configuration of a bio-item searching apparatus to which the present invention is applied.

A logical configuration of the bio-item searching apparatus will be explained below with reference to FIG. 4. FIG. 4 is a block diagram showing an example of a configuration of the bio-item searching apparatus to which the present invention is applied. FIG. 4 schematically depicts only a part related to the present invention in the configuration.

In FIG. 4, the bio-item searching apparatus 100 schematically includes a control unit 102 such as a CPU which integrally controls the entire operation of the bio-item searching apparatus 100, a communication control interface unit 104 connected to a communication device (not shown) such as a router connected to a communication line or the like, an input/output control interface unit 108 connected to an input device 112 or an output device 114, and a storage unit 106 that stores various databases or tables. These components are communicably connected to a network 300 through an arbitrary communication path.

The various databases or tables (all-literature set file 106a to identifier information database 106e) stored in the storage unit 106 are storage means such as a fixed disk device or the like, and store various programs, tables, files, databases, web pages, and the like which are used in various processes.

Of these constituent elements of the storage unit 106, the bio-item literature set file 106b stores a bio-item literature set having a literature in which a bio-item name of a bio-item is described for each bio-item. As shown in FIG. 4, the bio-item literature set file 106b stores a bio-item literature set which is a group of literatures including a bio-item name for each of bio-items 1 to n.

The all-literature set file 106a stores an all-literature set having all literatures included in the bio-item literature sets of these bio-items 1 to n.

The bio-item relation database 106c stores a correlation score between two arbitrary bio-items as a co-occurrence correlation score, and the two bio-items. In this case, as an exemplary embodiment, the bio-item relation database 106c may store the two bio-items which are determined to have a significant correlation since the co-occurrence correlation score is satisfied with a significant level, and are related to each other.

The position information database 106d stores genome position information representing a position on a corresponding genome chromosome in association with each other for each bio-item.

The identifier information database 106e stores identifier information representing a corresponding identifier in association with each other for each bio-item.

In FIG. 4, the communication control interface unit 104 performs communication control between the bio-item searching apparatus 100 and the network 300 (or a communication device such as a router). More specifically, the communication control interface unit 104 has a function of performing data communication with another terminal through a communication line.

In FIG. 4, the input/output control interface unit 108 controls the input device 112 and the output device 114. As the output device 114, not only a monitor but also a speaker may be used. As the input device 112, a keyboard, a mouse, a microphone, or the like may be used. The monitor can realize a pointing device function in cooperation with the mouse. The embodiment has a configuration in which a user can input a keyword, an interval, or an identifier through the input device 112 such as a keyboard and browse an output searching result through the output device 114 such as a monitor.

In FIG. 4, the control unit 102 has an internal memory to store a control program such as an OS (Operating System), a program that defines various procedures, and required data, and performs information processing to execute various processes by these programs or the like. The control unit 102 functionally conceptually includes a number-of-literatures acquiring unit 102a, a candidate bio-item selecting unit 102b, a table creating unit 102c, a correlation score calculating unit 102d, a co-occurrence correlation score calculating unit 102e, a bio-item relation database creating unit 102f, a related bio-item extracting unit 102g, an integrated correlation score calculating unit 102h, an output unit 102i, a genome region determining unit 102j, and an identifier determining unit 102k.

The number-of-literatures acquiring unit 102a searches with a keyword in a bio-item literature set of the bio-items 1 to n stored in the bio-item literature set file 106b to acquire the number (Nh) of literatures each including the keyword in each bio-item literature set for each of bio-items 1 to n. In this case, the number-of-literatures acquiring unit 102a may search with the keyword in the all-literature set stored in the all-literature set file 106a to acquire the number (Nk) of literatures each including the keyword in the all-literature set. The number-of-literatures acquiring unit 102a may search a bio-item literature set of one candidate bio-item in two arbitrary candidate bio-items with the other bio-item to acquire the number (Ns) of literatures each including the other bio-item name and the keyword.

The candidate bio-item selecting unit 102b selects a bio-item of a bio-item literature set in which the number-of-literatures Nh acquired by the number-of-literatures acquiring unit 102a is 1 or larger as a candidate bio-item.

The table creating unit 102c creates a number-of-literatures table constituted by at least one of four items a) to d): a) the number-of-literatures Nh, b) the number of literatures each not including the keyword and including the bio-item name (the number of literatures in the bio-item literature set of the bio-item—Nh), c) the number of literatures each including the keyword and not including the bio-item name (Nk−Nh), and d) the number of literatures each not including the keyword and not including the bio-item name (the total number of literatures in the all-literature set—the number of literatures in the bio-item literature set—Nk+Nh) for each candidate bio-item selected by the candidate bio-item selecting unit 102b (see FIGS. 2 and 3. The Nk and Nh are acquired by the number-of-literatures acquiring unit 102a.). In this case, the table creating unit 102c may create a three-dimensional literature table based on the number-of-literatures Ns acquired by the number-of-literatures acquiring unit 102a, number-of-literatures tables of two candidate bio-items, and a number-of-co-occurrence-literatures table related to the two candidate bio-items.

The correlation score calculating unit 102d calculates a correlation score between the candidate bio-item and the keyword for each candidate bio-item based on statistical calculation by using the number-of-literatures table created by the table creating unit 102c. In this case, the correlation score calculating unit 102d may use a test as the statistical calculation such as a Fisher's exact test and a chi-square test, or a Bayes conditional probability. In this case, the correlation score calculating unit 102d, as shown in FIG. 4, includes a co-occurrence keyword correlation score calculating unit 102m. The co-occurrence keyword correlation score calculating unit 102m calculates a co-occurrence keyword correlation score among two candidate bio-items and a keyword based on statistical calculation by using the three-dimensional number-of-literatures table created by the table creating unit 102c. In this case, the co-occurrence keyword correlation score calculating unit 102m may calculate the correlation score of two candidate bio-items when a keyword is included as a keyword-included correlation score, calculate a correlation score of two candidate bio-items when a keyword is not included as a keyword-not-included correlation score, and calculate any one of both the keyword-included correlation score and the keyword-not-included correlation score and a comparison result therebetween or both as a co-occurrence correlation score.

The co-occurrence correlation score calculating unit 102e calculates a co-occurrence correlation score based on statistical calculation by using a number-of-co-occurrence-literatures table constituted by at least one of i) the number of literatures each including one of two bio-item names and the other of the bio-item names, j) the number of literatures each not including one of the bio-item names and including the other of the bio-item names, k) the number of literatures each including one of the bio-item names and including the other of the bio-item names, and m) the number of literatures each not including one of the bio-item names and not including the other of bio-item names obtained by searching with the other of the bio-item names in a bio-item literature set of one of two arbitrary bio-items. In this case, the co-occurrence correlation score calculating unit 102e may obtain values of the items i) to m) by searching with any one of the bio-item names and the other of the bio-item names or both in the all-literature set stored in the all-literature set file 106a. In this case, the co-occurrence correlation score calculating unit 102e may use a test as the statistical calculation such as a Fisher's exact test and a chi-square test, or a Bayes conditional probability.

The bio-item relation database creating unit 102f stores the co-occurrence correlation score calculated by the co-occurrence correlation score calculating unit 102e in the bio-item relation database 106c in association with the two bio-items.

The related bio-item extracting unit 102g extracts a bio-item correlated to the candidate bio-item selected by the candidate bio-item selecting unit 102b as a related bio-item based on the co-occurrence correlation score stored in the bio-item relation database 106c.

The integrated correlation score calculating unit 102h calculates an integrated correlation score between the related bio-item and the keyword by integrating the correlation score between a candidate bio-item serving as a source of extraction by the related bio-item extracting unit 102g and the keyword with the co-occurrence correlation score stored in the bio-item relation database creating unit 102f. In this case, the integrated correlation score calculating unit 102h may calculate the integrated correlation score based on the following numerical expression 1 or an approximate expression (following numerical expressions 1-1 and 1-2) of the numerical expression 1. In the expressions, reference symbol P denotes an integrated correlation score, reference symbol P1 denotes a correlation score between the candidate bio-item and the keyword, and symbol P2 denotes a co-occurrence correlation score between the candidate bio-item and the correlated bio-item.

$$P = 1-(1-P1)(1-P2) \quad \text{(Numerical Expression 1)}$$

$$P = P1 + P2 \quad \text{(Numerical Expression 1-1)}$$

$$\text{Log}(P) = \text{Max}(\text{Log}(P1), \text{Log}(P2)) \quad \text{(Numerical Expression 1-2)}$$

(where Max{A,B} is a function of selecting not smaller one of A and B)

In this case, in a multiple interval mode in which two genome regions (intervals) are input, when a total correlation score (total P) among the two candidate bio-items (bio-item 1 and bio-item 2) and the keyword is calculated, the integrated correlation score calculating unit 102h may be designed to integrate the correlation scores by using any one of the following numerical expressions:

$$\text{Total } P = 1-(1-P1)(1-P2)(1-P3) \quad \text{(Numerical Expression 2)}$$

$$\text{Total } P = \text{Min}\{1-(1-P1)(1-P2), 1-(1-P1)(1-P3)\} \quad \text{(Numerical Expression 3)}$$

(where P1 is a correlation score between bio-item 1 and bio-item 2, P2 is a correlation score between bio-item 1 and a keyword, P3 is a correlation score between the bio-item 2 and the keyword, and Min{A,B} is a function of selecting not larger one of A and B (see FIG. 7)).

The output unit 102i outputs a candidate bio-item to the output device 114 based on the correlation score calculated by the correlation score calculating unit 102d. In this case, the output unit 102i may output a related bio-item to the output device 114 based on the integrated correlation score calculated by the integrated correlation score calculating unit 102h. The output unit 102i may output the co-occurrence keyword correlation score calculated by the co-occurrence keyword correlation score calculating unit 102m to the output device 114 in association with the two candidate bio-items. In this case, the output unit 102i may be designed not to output a corresponding candidate bio-item or a related bio-item when the correlation score or the integrated correlation score is not-satisfied with a predetermined significant level. In this case, the output unit 102i, as shown in FIG. 4, includes a search result order output unit 102n. The search result order output unit 102n ranks the corresponding candidate bio-items or the related bio-items based on the correlation score, the co-occurrence keyword correlation score, or the integrated correlation score to output the candidate bio-items or the related bio-items to the output device 114. As an example, the search result order output unit 102n may sequentially output the candidate bio-items or the related bio-items in an ascending order of the corresponding correlation scores or the integrated correlation scores.

The genome region determining unit 102j determines whether a position based on corresponding genome position information stored in the position information database 106d is included in a genome region (interval) based on genome region information input by a user with respect to a candidate bio-item or a related bio-item. When it is determined that the position is included in the genome region, the genome region determining unit 102j performs control to output the corresponding candidate bio-item or the related bio-item. In this case, in the embodiment, the genome region determining unit 102*j* may be designed to output an instruction to the related bio-item extracting unit 102*g* to extract a related bio-item related to the candidate bio-item when it is determined that a position on a genome of the candidate bio-item selected by the candidate bio-item selecting unit 102*b* is not included in the genome region (interval) input by the user.

The identifier determining unit 102*k* determines whether an identifier based on corresponding identifier information stored in the identifier information database 106*e* is included in one identifier or a plurality of identifiers based on identifier information input by a user with respect to a candidate bio-item or a related bio-item. When it is determined that the identifier is included in the identifier or the identifiers, the identifier determining unit 102*k* performs control to output the corresponding candidate bio-item or the related bio-item.

This is a logical configuration of the inside of the bio-item searching apparatus 100. In this case, the bio-item searching apparatus 100, as shown in FIG. 4, may be communicably connected to an external system 250 which provides an external program such as an external database related to literature information or a bio-item searching program, and a bio-item searching terminal apparatus 600 through the network 300. In FIG. 4, the network 300 has a function of connecting the bio-item searching apparatus 100, the external system 250, and the bio-item searching terminal apparatus 600 with each other. For example, the Internet, a LAN, a public telephone network, or the like is used as the network 300.

In FIG. 4, the external system 250 is mutually connected to the bio-item searching apparatus 100 through the network 300 and has a function of providing a web site which executes an external program such as an external database related to literature information or a bio-item searching program to a user. In this case, the external system 250 may be designed to serve as a WEB server or an ASP server. The hardware configuration of the external system 250 may be constituted by an information processing device such as a commercially available workstation or personal computer and a peripheral device thereof. The functions of the external system 250 are realized by a CPU, a disk device, a memory device, an input device, an output device, a communication control device, and the like in the hardware configuration of the external system 250 and programs which control these devices.

In FIG. 4, the bio-item searching terminal apparatus 600 is mutually connected to the bio-item searching apparatus 100 through the network 300 and includes at least a control unit, an input unit, and an output unit. The bio-item searching terminal apparatus 600 performs control to cause a user to input a keyword, genome region information, or identifier information through the input unit and is designed to transmit the keyword or the like to the bio-item searching apparatus 100, receive a candidate bio-item, a related bio-item or a co-occurrence keyword correlation score output from the bio-item searching terminal apparatus 600, and output the candidate bio-item, the related bio-item, or the co-occurrence keyword correlation score to the output unit.

This is the configuration of the bio-item searching apparatus and the bio-item searching system.

Process of the Bio-item Searching Apparatus

An example of a process of the bio-item searching apparatus 100 according to the embodiment constructed as described above will be explained below in detail with reference to FIGS. 5 and 6.

In this case, "direct searching" means searching for a bio-item directly related to a keyword, and is searching which outputs a candidate bio-item as a searching result (answer of direct searching). On the other hand, "indirect searching" means searching which performs inference between bio-items to search for a bio-item indirectly related to a keyword, and is searching which outputs a related bio-item as a searching result (answer of bio-item inference).

Direct Searching Process

The details of a direct searching process will be explained below with reference to FIG. 5. FIG. 5 is a flow chart showing an example of a direct searching process of this system according to the embodiment.

Figure 5:
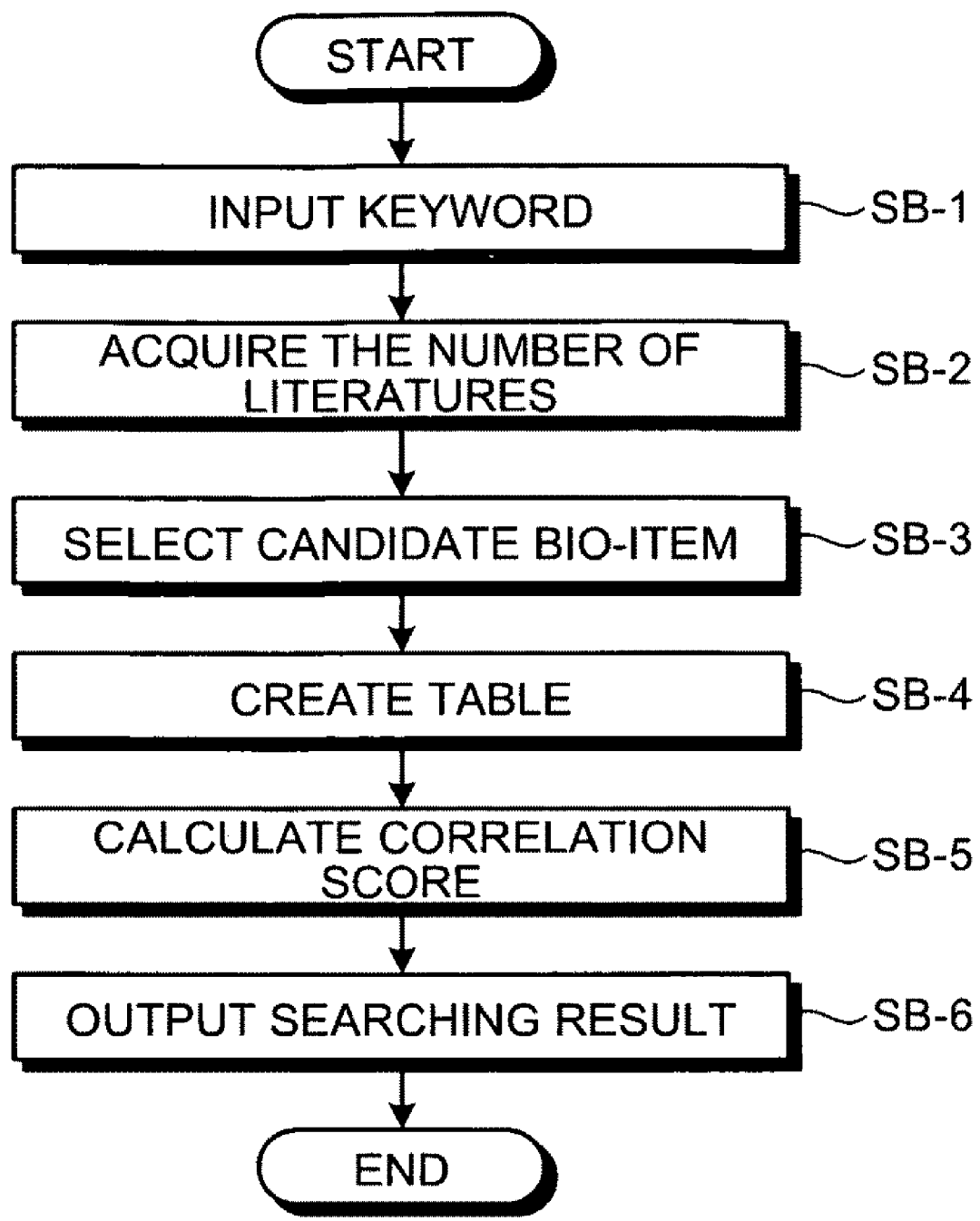
FIG. 5 is a flow chart showing an example of a direct searching process of a system according to an embodiment.

As shown in FIG. 5, the control unit 102 of the bio-item searching apparatus 100 causes a user to input a keyword through the input device 112. When the control unit 102 receives the keyword (SB-1), the number-of-literatures acquiring unit 102*a* searches with the keyword in each bio-item literature set stored in the bio-item literature set file 106*b* to acquire the number (Nh) of literatures each having the keyword in the bio-item literature set for each of bio-items 1 to n (SB-2). In this case, the number-of-literatures acquiring unit 102*a* may search with the keyword in the all-literature set stored in the all-literature set file 106*a* to acquire the number (Nk) of literatures each including the keyword in the all-literature set.

The candidate bio-item selecting unit 102*b* selects a bio-item of the bio-item literature set in which the acquired number-of-literatures Nh is 1 or larger as a candidate bio-item (SB-3).

Subsequently, the table creating unit 102*c* creates a number-of-literatures table constituted by at least one of four items: a) the number-of-literatures Nh, b) the number of literatures each not including a keyword and including a bio-item name (the number of literatures in a bio-item literature set of the bio-item—Nh), c) the number of literatures each including a keyword and not including a bio-item name (Nk−Nh), and d) the number of literatures each not including a keyword and not including a bio-item name (the total number of literatures in the all-literature set—the number of literatures in a bio-item literature set—Nk+Nh) for each candidate bio-item (SB-4).

The correlation score calculating unit 102*d* calculates correlation scores between candidate bio-items constituting a candidate bio-item group and the keyword based on a Fisher's exact test by using the number-of-literatures table created by the process of the table creating unit 102*c* (SB-5).

The output unit 102*i* outputs the candidate bio-items to the output device based on the correlation scores calculated by the correlation score calculating unit 102*d* (SB-6).

This is the process of direct searching.

Indirect Searching Process (Inference of Bio-Item)

An indirect searching process will be explained below with reference to FIG. 6. FIG. 6 is a flow chart showing an example of an indirect searching process of the system according to the embodiment.

A process of creating a bio-item relation database used in inference of a bio-item will be explained below. The co-occurrence correlation score calculating unit 102*e* calculates a co-occurrence correlation score between two bio-items based on a Fisher's exact test by using the number-of-co-occurrence-literatures table constituted by at least one of i) the number of literatures each including one of two bio-item names and the other of the bio-item names, j) the number of literatures each not including one of the bio-item names and including the other of the bio-item names, k) the number of literatures each including one of the bio-item names and not including the other of the bio-item names, and m) the number of literatures each not including one of the bio-item names and not including the other of the bio-item names, obtained by searching with the other of the bio-item names in a bio-item literature set of one of two arbitrary bio-items (SC-1).

The bio-item relation database creating unit 102f stores the co-occurrence correlation score calculated by the co-occurrence correlation score calculating unit 102e in the bio-item relation database 106c in association with the two bio-items (SC-2). This is the process of creating the bio-item relation database 106c. The creating process is executed in advance before direct searching or indirect searching is performed.

Subsequently, the bio-item searching apparatus 100 causes a user to input a keyword through the input device 112 and executes direct searching (SC-3 to 7). In this case, since SC-3 to 7 correspond to SB-1 to 5 of the direct searching, a description thereof will be omitted.

Figure 6:
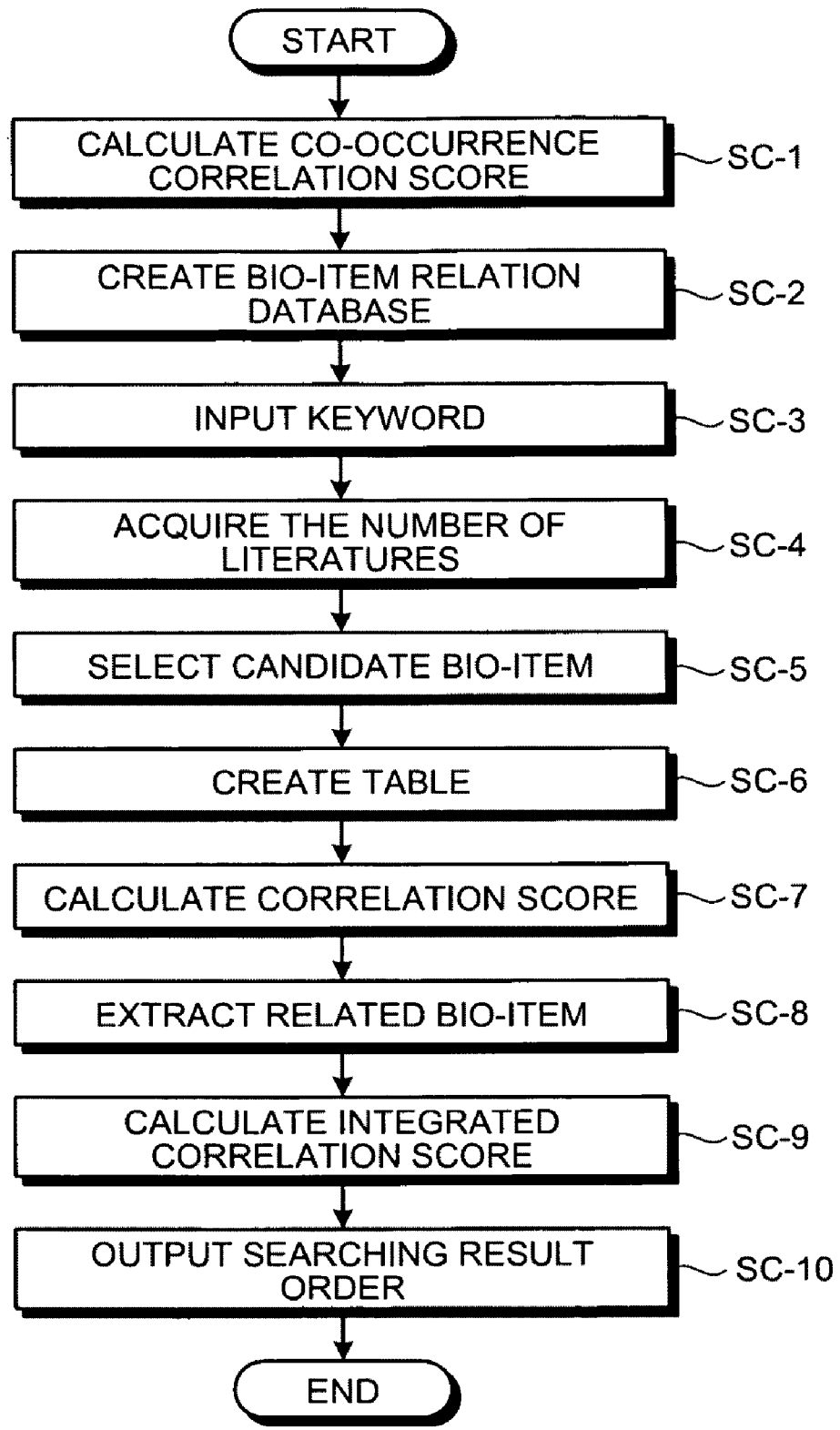
FIG. 6 is a flow chart showing an example of an indirect searching process of the system according to the embodiment.

A shift process from the direct searching to the indirect searching is constructed as a linear process as shown in FIG. 6. In addition, when it is determined by the process of the genome region determining unit 102j that the candidate bio-item selected in SC-5 is not included in an interval input by the user, the control operation may shift to SC-8 to instruct the related bio-item extracting unit 102g to extract a related bio-item correlated with the candidate bio-item determined not included in the interval.

The related bio-item extracting unit 102g extracts a related bio-item correlated based on the co-occurrence correlation score stored in the bio-item relation database 106c and corresponding to the candidate bio-item selected by the candidate bio-item selecting unit 102b (SC-8).

The integrated correlation score calculating unit 102h calculates an integrated correlation score P between a related bio-item extracted by the related bio-item extracting unit 102g and the keyword by integrating a correlation score (P1) calculated by the correlation score calculating unit 102d with a (co-occurrence) correlation score (P2), obtained by the bio-item relation database 106c, between the candidate bio-item obtained by the candidate bio-item selecting unit 102b and the related bio-item extracted by the related bio-item extracting unit 102g by using the following numerical expression 1 (SC-9).

Integrated $P=1-(1-P1)(1-P2)$ (Numerical Expression 1)

The output unit 102i outputs the related bio-items extracted by the related bio-item extracting unit 102g based on the integrated correlation score calculated by the integrated correlation score calculating unit 102h (SC-10).

This is the indirect searching process.

Genome Region Determining Process

A genome region determining process by the genome region determining unit 102j will be explained below in detail.

In the input device 112, a user can specify, in addition to the keyword, information (genome region information) related to a region (genome region) on a genome sequence called an "interval". By this genome region determining function, the user of the bio-item searching apparatus 100 can narrow down a searching result in consideration of the position on the genome sequence of the bio-item in, for example, solving a problem in positional cloning.

More specifically, the genome region determining unit 102j extracts corresponding genome position information based on the position information database 106d with respect to the candidate bio-item selected by the candidate bio-item selecting unit 102b or the related bio-item extracted by the related bio-item extracting unit 102g.

The genome region determining unit 102j determines whether a position on a genome based on the acquired genome position information is included in the genome region (interval) input by the user.

When the genome region determining unit 102j determines the candidate bio-item is included in the interval, the genome region determining unit 102j determines that the searching result (answer) is proper and instructs the output unit 102i to output this bio-item. On the other hand, when the genome region determining unit 102j determines that the candidate bio-item is not included in the interval, the genome region determining unit 102j discards the bio-item as an improper searching result (answer). At this time, the genome region determining unit 102j may be designed to instruct the related bio-item extracting unit 102g to extract a bio-item related to the bio-item. In this case, the "interval" may include a state in which an interval or a sequence of identifiers or both the interval and the sequence of identifiers are specified. In this case, more specifically, when a user input the interval or the sequence of identifiers or both the interval and the sequence of identifiers, the genome region determining unit 102j may execute the genome region determining process with respect to the input interval and the input sequence of identifiers.

Table Creating Process and Correlation Score Calculating Process

Figure 7:
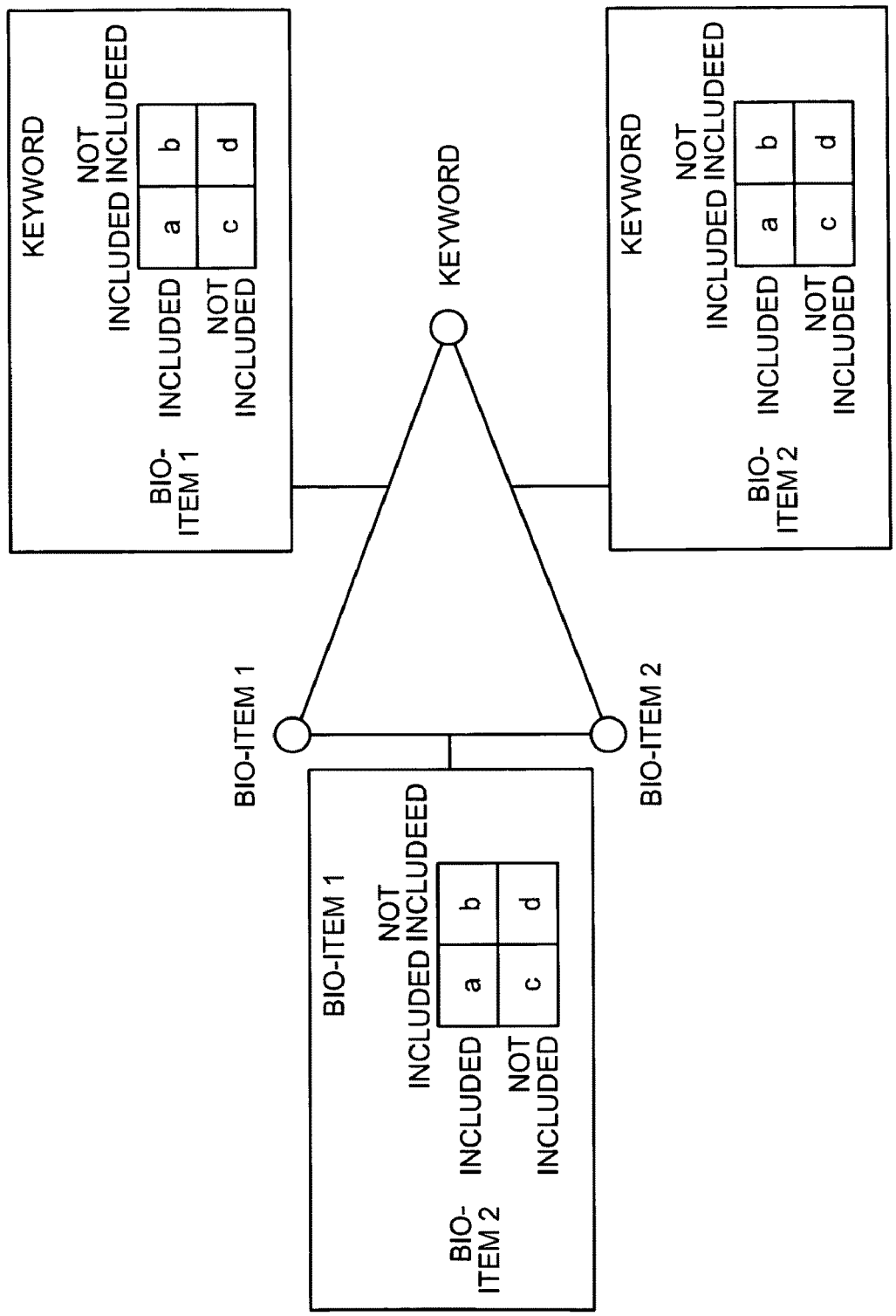
FIG. 7 is a pattern diagram showing a relation between a keyword and a bio-item.

In this case, as a method of quantitatively evaluating a relativity of a keyword and bio-items (candidate bio-items and related bio-items), a table creating process performed by the process of the table creating unit 102c and a correlation score calculating process performed by the processes of the correlation score calculating unit 102d, the co-occurrence correlation score calculating unit 102e, and the integrated correlation score calculating unit 102h will be explained in detail with reference to FIG. 7. FIG. 7 is a diagram typically showing a relationship between a keyword and a bio-item.

More specifically, as shown in FIG. 7, in direct searching, bio-item 1 corresponds to a candidate bio-item. The correlation score calculating unit 102d calculates a correlation score between the candidate bio-item and a keyword by using a number-of-literatures table between the bio-item 1 and the keyword.

In indirect searching, the bio-item 1 corresponds to a candidate bio-item related to a keyword, and bio-item 2 corresponds to a related bio-item obtained by inference.

In a multiple interval mode (when a user inputs two genome regions), the bio-item 1 corresponds to a bio-item belonging to one of the genome regions, and the bio-item 2 corresponds to a bio-item belonging to the other of the genome regions. In this case, the bio-item 1 in FIG. 7 serves as a bio-item belonging to interval 1, and the bio-item 2 serves as a bio-item belonging to the interval 2. More specifically, in the multiple interval mode, the bio-item 1 is a bio-item belonging to the interval 1 and related to a keyword, and the bio-item 2 is a bio-item belonging to the interval 2 and related to the keyword.

In this case, the multiple interval mode will be explained below. The correlation score calculating unit 102d calculates a correlation score between a candidate bio-item and the keyword by using a number-of-literatures table of the bio-item 1 and the keyword, and the co-occurrence correlation score calculating unit 102e calculates a co-occurrence correlation score by using a number-of-literatures table of the bio-item 1 and the bio-item 2. At this time, since the correlation score between the bio-item 2 and the keyword cannot be directly calculated by using the number-of-literatures table between the bio-item 2 and the keyword, the integrated correlation score calculating unit 102h integrates the correlation score calculated by the correlation score calculating unit 102d with the co-occurrence correlation score calculated by the co-occurrence correlation score calculating unit 102e to calculate an integrated correlation score.

More specifically, by the processes of the number-of-literatures acquiring unit 102a, the candidate bio-item selecting unit 102b, and the genome region determining unit 102j, for each interval 1 and 2, direct search is performed, and groups of bio-items (candidate bio-item group 1 and candidate bio-item group 2) are obtained as searching results. By a process of the co-occurrence keyword correlation score calculating unit 102m, each one bio-item is extracted from each of the two groups, and all constructed bio-item pairs are formed. It is checked whether each of the bio-item pairs corresponds to the two bio-items co-occurring in one of the literatures as described above.

When the bio-item pair corresponds to the two bio-items, three correlation scores including correlation scores (correlation score 1 and correlation score 2) between the two corresponding bio-items and a keyword and a co-occurrence correlation score between the two-bio items are integrated to calculate a new correlation score ("integrated correlation score"). Based on these correlation scores, ranking of the bio-item pairs is performed and displayed. As described above, even in the multiple interval mode, by a ranking function by a statistical process, precision of finding a target bio-item can be advantageously more improved.

In this case, attention is given to the relationship between the keyword and the bio-item 1. To quantatively evaluate the relativity, a number-of-literatures table in which the numbers of literatures as shown in FIG. 2 are tabularized may be created.

When names (bio-item names) m1, m2, ..., mp of the bio-items are given, a query which acquires a literature including at least one of these names is expressed by Q=m1 OR m2 OR ... OR mp and is called a "bio-item query". Inverted Q, i.e., a query which acquires a literature which does not include any one of these names is expressed by ¬Q. A bio-item query for the bio-item 1 is expressed by Q1.

In the number-of-literatures table shown in FIG. 2, a is the number of literatures which satisfy Q1 and include a keyword, b is the number of literatures which satisfy Q1 and do not include the keyword, c is the number of literatures which satisfy ¬Q1 and include the keyword, and d is the number of literatures which satisfy ¬Q and do not include the keyword.

A Fisher's exact test method or the like is applied as an example to the table to calculate a P value ("P" is written in italic in the international standards). The P value which is approximate to 0 shows that a relativity between a bio-item and a keyword is high. By using the value, retrieved bio-items are ranked.

Similarly, a number-of-literatures table is created in a relationship between the bio-item 1 and the bio-item 2 (for example, co-occurrence correlation between a candidate bio-item and a related bio-item). Values a), b), c), and d) in the table are the numbers of literatures (will be explained below). It is assumed that a bio-item query about the bio-item 1 and a bio-item query about the bio-item 2 are represented by $Q_1$ and $Q_2$ respectively.

At this time, in the number-of-literatures table in FIG. 2, a) is the number of literatures which satisfy Q1 and satisfy Q2, b) is the number of literatures which satisfy Q1 and satisfy ¬Q2, c) is the number of literatures which satisfy ¬Q1 and satisfy Q2, and d) is the number of literatures which satisfy ¬Q1 and satisfy ¬Q2.

By using the number-of-literatures table created as described above, based on statistical calculation, a co-occurrence correlation score is calculated. As the statistical calculation, for example, a test such as a Fisher's exact test or a chi-square test, or a Bayes conditional probability is applied to calculate the P value.

This is the table creating process and the correlation score calculating process.

Integrated Correlation Score Calculating Process

An example of an integrated correlation score calculating process will be described below. Even when a candidate bio-item having sufficiently high correlation is obtained by direct searching, if a position on a genome of the candidate bio-item is not included in an interval input by a user, the candidate bio-item is discarded because the candidate bio-item is not improper as an answer. However, when a related bio-item is derived from the candidate bio-item by using a bio-item relation database, a new correlation score must be calculated.

In this case, it is improper to directly calculate a correlation score between a related bio-item and a keyword. This is because the related bio-item is a searching result that is not obtained until indirect searching is performed through the candidate bio-item. Even when the number of literatures (almost 0) which is a result of the direct searching is assigned, the P value is approximate to 1, and a candidate bio-item group is not output at a higher rank in the searching result. For this reason, the problem of the conventional technique cannot be solved.

Therefore, without directly calculating a correlation score between a related bio-item and a keyword, a correlation score P ("integrated correlation score") between the related bio-item and the keyword is indirectly calculated by integrating a correlation score (co-occurrence correlation score) between the candidate bio-item and the related bio-item with a correlation score between the keyword and the candidate bio-item. Specifically, the following numerical expression is used in calculation.

$$P=1-(1-P1)(1-P2) \quad \text{(Numerical Expression 1)}$$

where P1 is a co-occurrence correlation score between a related bio-item and a candidate bio-item, and P2 is a correlation score between a candidate bio-item and a keyword.

In the multiple interval mode, direct searching is performed with respect to each interval, each group of bio-items is obtained as a searching result. One bio-item is extracted from each of the groups to form all constructed bio-item pairs. It is checked whether each of the bio-item pairs corresponds to the two bio-items co-occurring in one of the literatures as described above.

When the bio-item pair corresponds to the two bio-items, correlation scores between the two bio-items and the keyword are integrated with a correlation score between the two bio-items to calculate a new correlation score. Based on these correlation scores, ranking of the bio-item pairs is performed and displayed. In this case, an equation (a total correlation function) is expressed as, for example, the following numerical expression 2 or 3.

$$\text{Total } P=1-(1-P1)(1-P2)(1-P3) \quad \text{(Numerical Expression 2)}$$

$$\text{Total } P=\text{Min}\{1-(1-P1)(1-P2), 1-(1-P1)(1-P3)\} \quad \text{(Numerical Expression 3)}$$

where P1 is a correlation score between bio-item 1 and bio-item 2, P2 is a correlation score between bio-item 1 and a keyword, P3 is a correlation score between the bio-item 2 and the keyword, and Min{A,B} is a function of selecting not larger one of A and B (see FIG. 7).

Co-Occurrence Correlation Keyword Score Calculating Process: Number-of-Literatures Three-Dimensional Table A co-occurrence keyword correlation score calculating process using a three-dimensional number-of-literatures table will be explained below with reference FIGS. 8 and 9.

The number-of-literatures acquiring unit 102a searches a bio-item literature set of one of two arbitrary bio-items to acquire the number (Ns) of literatures each including the other of the bio-items and a keyword.

Figure 8:
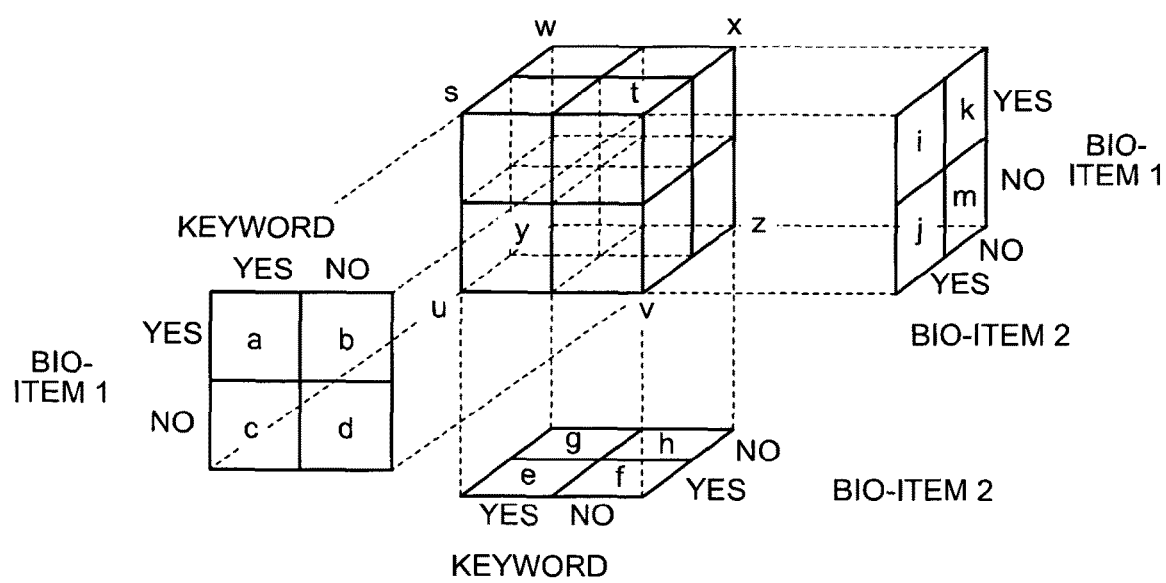
FIG. 8 is a pattern diagram showing a method of creating a three-dimensional number-of-literatures table.

The table creating unit 102c creates a three-dimensional number-of-literatures table based on the number-of-literatures Ns, number-of-literatures tables according to the two bio-items, and a number-of-co-occurrence-literatures table according to the two bio-items. In this case, a method of creating the three-dimensional literature table will be explained below with reference to FIG. 8. FIG. 8 is a diagram typically showing the method of creating the three-dimensional number-of-literatures table.

As shown in FIG. 8, the table creating unit 102c creates a table (three-dimensional number-of-literatures table) constituted by the numbers of literatures classified into eight classification items s), t), u), v), w), x), y), and z), i.e., whether a keyword is included or not, whether the bio-item 1 is included or not, and whether the bio-item 2 is included or not.

In this case, to rapidly create the three-dimensional literature table, the table creating unit 102c creates a database of number-of-co-occurrence-literatures tables created by the process of the co-occurrence correlation score calculating unit 102e and constituted by four items i), j), k), and m) about combinations of two arbitrary bio-items in advance.

When a user inputs a keyword, the number-of-literatures acquiring unit 102a to the table creating unit 102c create number-of-literatures tables between the bio-items and the keyword. The number-of-literatures tables created here correspond to number-of-literatures tables constituted by a), b), c), and d) in one of the bio-items and e), f), g), and h) in the other of the bio-items.

With respect to a combination of arbitrary candidate bio-items 1 and 2, the table creating unit 102c searches for a literature including the keyword and the bio-item name 2 by the process of the number-of-literatures acquiring unit 102a using the bio-item literature set corresponding to the bio-item 1 to acquire the number-of-literatures Ns as s).

The table creating unit 102c calculates w=a−s, u=e−s, and t=i−s, and further v=f−t, x=k−w, y=c−u, and z=d−v by using a fact that the following relational expressions hold:

$$a=s+w$$

$$b=t+x$$

$$c=u+y$$

$$d=v+z$$

$$e=s+u$$

$$f=t+v$$

$$g=w+y$$

$$h=x+z$$

$$i=s+t$$

$$j=u+v$$

$$k=w+x$$

$$m=y+z.$$

Furthermore, z=d−v is calculated to generate a three-dimensional number-of-literatures table constituted by eight items including s) to z). As described above, in comparison with acquisition of the eight items s) to z) by searching processes for each item, the three-dimensional literature table can be rapidly created.

The correlation score calculating process will be explained next. More specifically, the correlation score calculating unit 102d calculates a co-occurrence keyword correlation scores among the two candidate bio-items and the keyword based on statistical calculation by the process of the co-occurrence keyword correlation score calculating unit 102m using the three-dimensional number-of-literatures table.

In this case, the co-occurrence keyword correlation score calculating unit 102m may calculate a correlation score between two candidate bio-items including keywords as "keyword-included correlation scores" by using the three-dimensional number-of-literatures table, and calculate a correlation score of two candidate bio-items not including keywords as a "keyword-not-included correlation score". In this case, the co-occurrence keyword correlation score calculating unit 102m calculates any one of both the "keyword-included correlation score" and the "keyword-not-included correlation score" and a comparison result therebetween or both as a co-occurrence correlation score. In this manner, the "co-occurrence keyword correlation score" which reflects a manner of a change in degree of the co-occurrence correlation between the bio-item 1 and the bio-item 2 caused by the presence/absence of the keyword can be calculated.

An example of a method of calculating a co-occurrence correlation score will be explained below with reference to FIG. 9. The present invention is not limited to the example. FIG. 9 is a diagram showing an example of a literature table for calculating the "keyword-included correlation score" and the "keyword-not-included correlation score".

As shown in FIG. 9, the co-occurrence keyword correlation score calculating unit 102m divides the three-dimensional number-of-literatures table into two two-dimensional number-of-literatures tables, and calculates correlation scores between the bio-item 1 and the bio-item 2 with respect to a literature group including a keyword input by a user and a literature group not including the keyword. More specifically, the former is the "keyword-included correlation score", and the latter is the "keyword-not-included correlation score".

The co-occurrence keyword correlation score calculating unit 102m compares the "keyword-included correlation score" with the "keyword-not-included correlation score". In this case, if the former has a higher correlation, it can be determined that a relativity between the bio-item 1 and the bio-item 2 has high importance in a category specified by the keyword. The information can be shown to a user as a co-occurrence keyword correlation score. When the latter has a higher correlation, it can be determined that the relativity between the bio-item 1 and the bio-item 2 is high in a category except for the category specified by the keyword, and the information can be shown to the user as a co-occurrence correlation score.

Concept Word Query Adding Process

In the method in which only a bio-item name is used in association between the bio-items and the literatures, the bio-items may not be correctly associated with each other. This is because the same word may be used as words having different meanings. For example, a mouse gene fuzzy appears in a literature as a general term which means "flexible" or the like. In this manner, when the bio-item name is a name which causes confusion in literature searching, a correct searching result is not output.

In order to solve the problem, as a method of improving association accuracy, a process of adding a concept word query to each bio-item will be explained below.

In this case, the "concept word" is a word representing a specific thesis or a specific field. When concept words n1, n2, . . . , np are given, a concept word query R=n1 OR n2 OR . . . OR np is defined. The concept word query is a query which acquires a literature including at least one of the concept words. When the bio-item query and its concept word query are represented by Q and R, respectively, for example, a bio-item added with a concept word is defined by Q AND R. This is a query which acquires a literature which satisfies Q and R. In generation of the number-of-literatures table, a bio-item query added with a concept word is used in place of a bio-item query.

For example, when bio-item names are GRB2-related adaptor protein 2, Grap2, Gads, GRID, Grb2-related adaptor downstream of Sch, Mona, Grf40, GRB2L, GrbX, GRAP-2, and GrpL, a process of setting a bio-item query ("grb2-related adaptor protein 2" OR "grap2" OR "gads" OR "grid" OR "grb2-related adaptor downstream of sch" OR "mona" OR "grf40" OR "grb21" OR "grbx" OR "grap¥-2" OR "grpl") AND ("adaptor protein" OR "adaptor proteins" OR "monocytic" OR "monocyte") obtained by adding the concept word R to a bio-item query Q "grb2-related adaptor protein 2" OR "grap2" OR "gads" OR "grid" OR "grb2-related adaptor downstream of sch" OR "mona" OR "grf40" OR "grb21" OR "grbx" OR "grap¥-2" OR "grpl" is performed. A part subsequent to AND is a concept word query.

As another example, when bio-item names are X-ray repair complementing defective repair in Chinese hamster cells 6, Xrcc6, Ku p70, Ku70, Xrcc6, and G22pl, a process of setting a bio-item query ("x¥-ray repair complementing defective repair in chinese hamster cells 6" OR "xrcc6" OR "ku p70" OR "ku70" OR "xrcc6" OR "g22pl") AND ("x ray" OR "dna repair" OR "hamsters" OR "hamster" OR "thyroid" OR "autoantigen" OR "dna¥-binding proteins" OR "dna¥-pkcs" OR "bax¥-binding") obtained by adding the concept word R to the bio-item query Q "x¥-ray repair complementing defective repair in chinese hamster cells 6" OR "xrcc6" OR "ku p70" OR "ku70" OR "xrcc6" OR "g22pl" is performed. In this case, a part subsequent to AND is a concept word query.

This is the details of the concept word adding process.

EMBODIMENT

An embodiment of the present invention will be explained below with reference to FIGS. 10 to 33. In a bio-item searching system according to the embodiment, a genome region (range on a genome sequence) called "interval" input by a user and a keyword are received, and a bio-item related to the keyword and present in the interval is acquired. The bio-item searching system includes two types of searching methods using bio-item searching performed by a single interval mode in which one interval is specified and bio-item searching by a multiple interval mode in which two intervals are specified. When specifying the intervals, a sequence of identifiers of a bio-item can also be specified in place of the interval, or both a sequences of identifiers of the bio-item and an interval can also be specified. Even when a sequence of identifiers of the bio-item is specified in place of the interval or together with the interval, "the presence in the interval" also means that a searching result is included in the sequence of identifiers. As will be shown in the explanation of the bio-item searching system, the present invention does not prevent the bio-item searching system from being executed in the same housing (for example, the bio-item searching apparatus 100) or a plurality of different housings. More specifically, in the embodiment, for explanatory convenience, an explanation may be made by using respective components (102a to 102k) of the control unit 102 of the bio-item searching apparatus 100. However, these components do not always function in the same housing of the bio-item searching system.

The bio-item searching system according to the embodiment has the following characteristic features. More specifically, 1) even when a bio-item such as a gene related to a keyword is not present in an interval, another bio-item present in the interval can be obtained by inference by applying a relationship between two genes extracted from a literature in advance or a relationship between two genes obtained by an experiment to the bio-item.

2) With respect to a bio-item such as a medical agent or a cell in which an interval is not present, searching for a bio-item related to a keyword and inference searching can be performed.

3) In the bio-item searching system, a plurality of literature set types 1 to m can be handled. An example of a specific literature set type is literature sets or the like obtained by a MedLine database or an OMIM database.

4) The bio-item searching system makes it possible to calculate a related score between a keyword and a bio-item by a statistical process. Based on the value, searching result items can be ranked.

5) Searching for a bio-item can be executed within several seconds.

In this case, literature sets handled in the embodiment may be classified into 1) a literature set ("document set") in which bio-items are associated with literatures in a many-to-many relationship and 2) a literature set ("catalog set") in which bio-items are associated with literatures in a one-to-one relationship.

An example in which the document set and the catalog set are used in the literature sets, respectively, is executed with respect to two types of searching methods of a single interval mode and a multiple interval mode. This will be exemplified in detail.

a. Single Interval Mode Searching to Document Set

Figure 10:
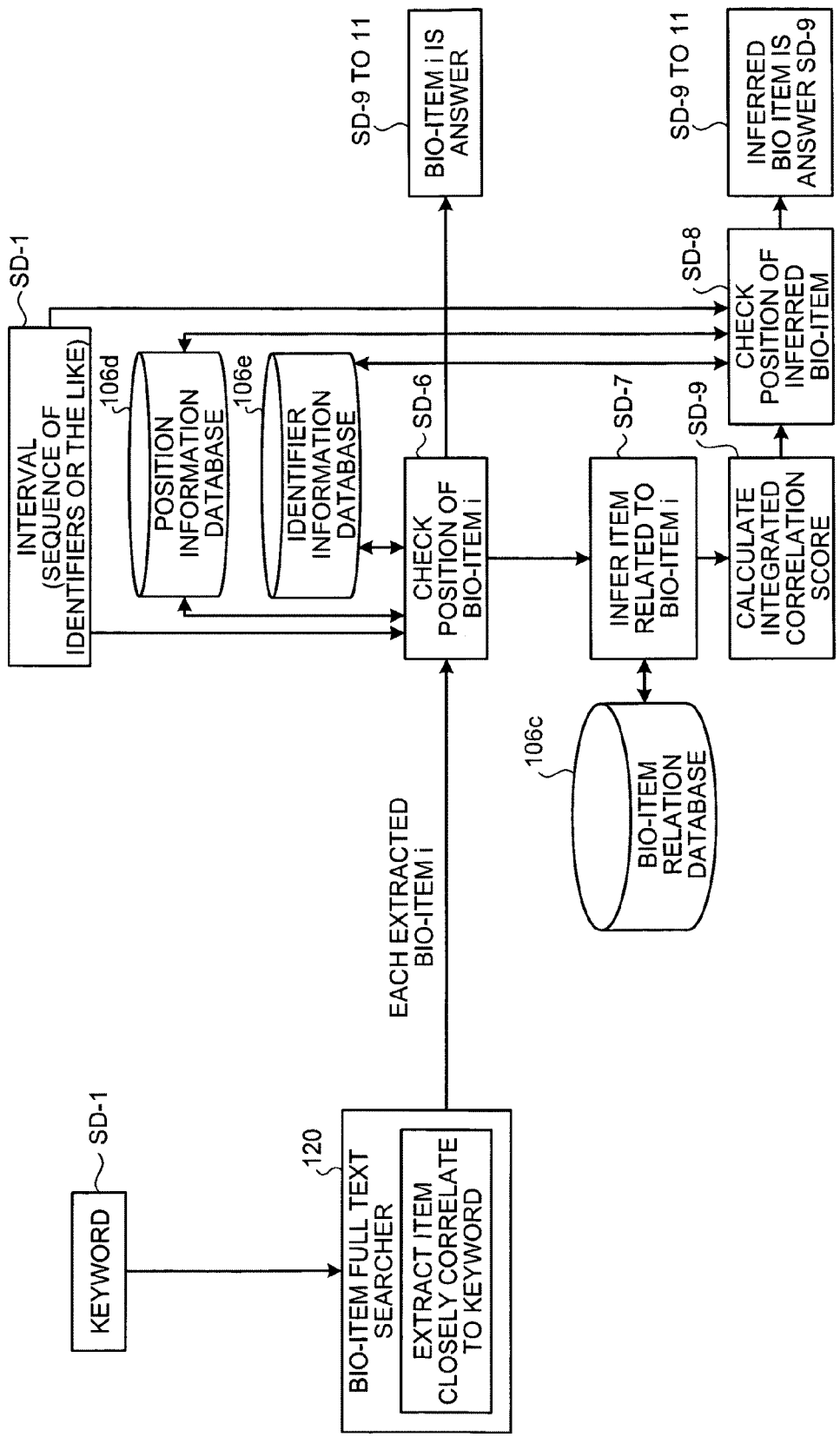
FIG. 10 is a diagram showing a flow of data when a bio-item is searched for in a single interval mode.
Figure 11:
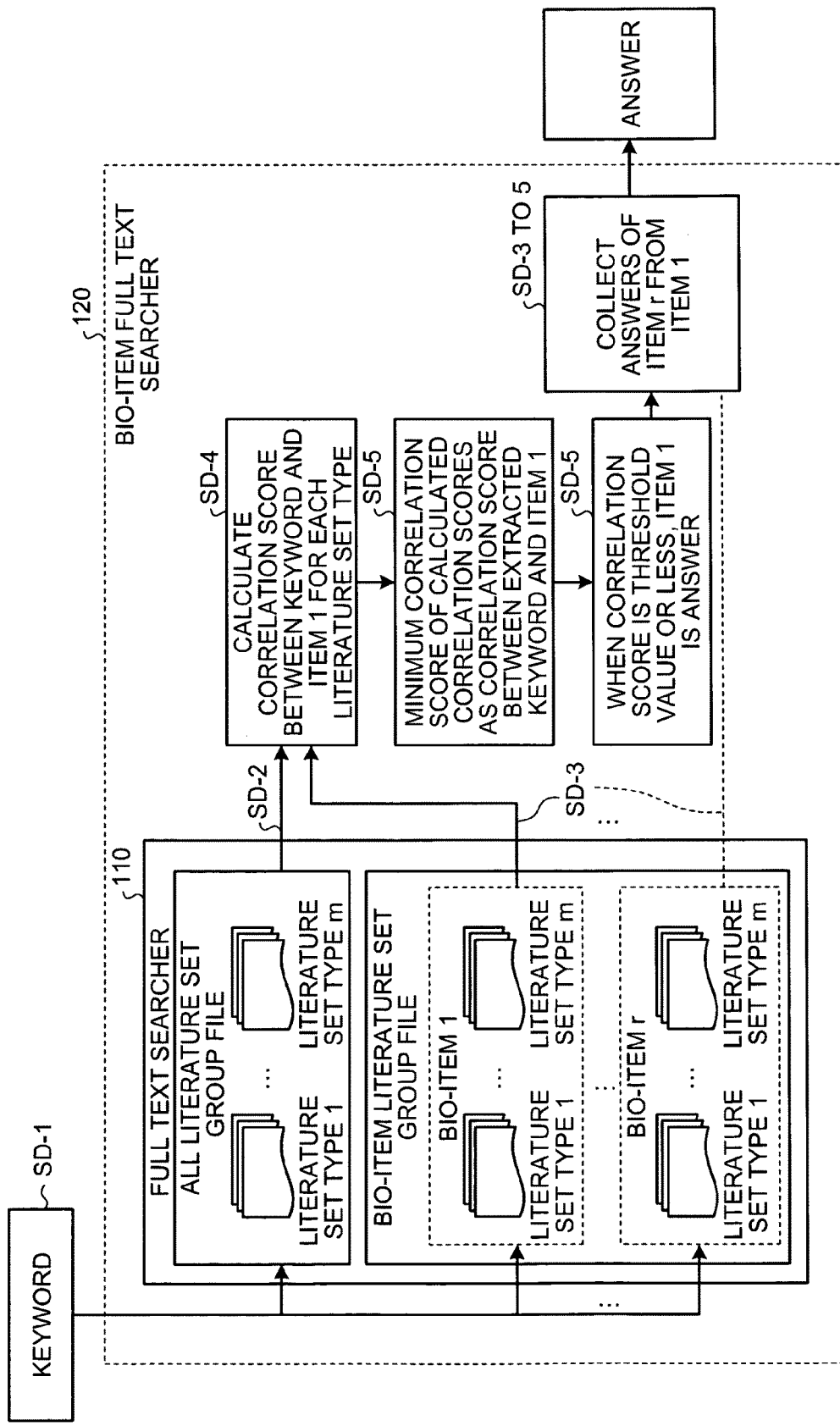
FIG. 11 is a diagram showing an outline of a bio-item full text searcher 120.
Figure 12:
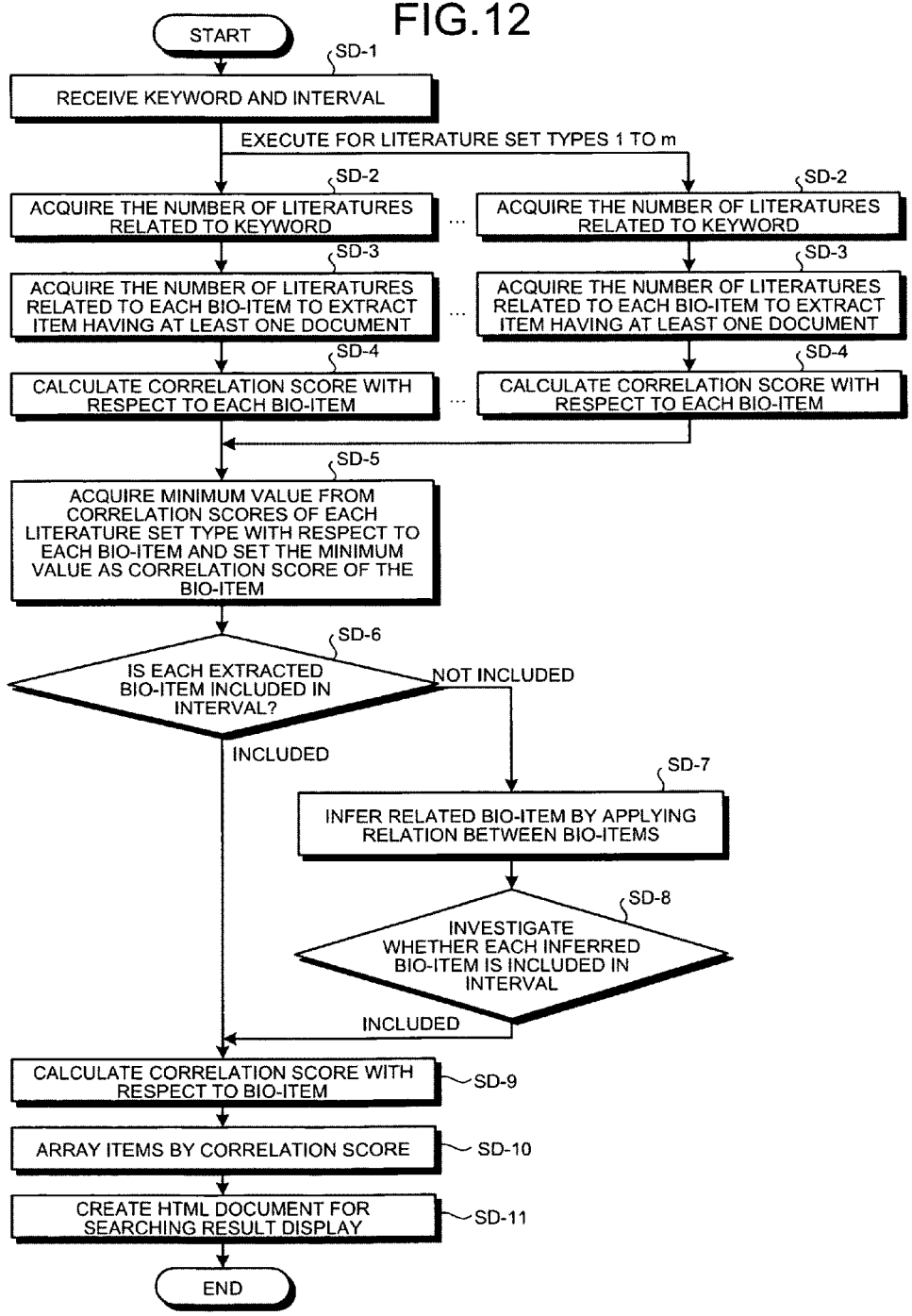
FIG. 12 is a flow chart showing an operation in the single interval mode.

Single interval mode searching to a document set will be described below with reference to FIGS. 10 to 12 and FIGS. 23 and 24. FIG. 10 is a diagram showing a flow of data when a bio-item is searched for in a single interval mode. FIG. 11 is a diagram showing an outline of a bio-item full text searcher 120. FIG. 12 is a flow chart showing an operation in a single interval mode. In FIGS. 10 and 12 or FIGS. 11 and 12, some steps are different in order or number. However, this means that the embodiment is not limited to the order of flows and the number of steps in FIG. 12.

According to the embodiment, as shown in FIG. 10, the bio-item full text searcher 120 acquires the number-of-literatures, selects the candidate bio-item, creates the table, and calculates the correlation score. Control devices of the bio-item searching system other than the bio-item full text searcher 120 in FIG. 10 mainly determine a genome region, extract related bio-items, calculate an integrated correlation score, and perform output.

As shown in FIG. 11, a storage device of the full text searcher 110 in the bio-item full text searcher 120 includes a literature set file which stores two types of literature data D1 and D2. More specifically, the literature data D1 is data obtained by collecting literatures associated with at least one bio-item with respect to literature set types 1 to m, and is used to acquire the number of literatures which are related to a keyword or are not related to the keyword (corresponding to an all-literature set). On the other hand, the literature data D2 is data obtained by collecting literature groups generated by literatures associated with each of bio-items 1 to r with respect to all the bio-items 1 to r. The literature data D2 is used to perform full-text searching by a keyword to the groups of literatures (literature sets) of each of the bio-items and to acquire the number of literatures related to the keyword and related to the bio-item (corresponding to a bio-item literature set).

As shown in FIGS. 10 to 12, when the bio-item full text searcher 120 receives a keyword and an interval (SD-1), the bio-item full text searcher 120 executes full-text searching by the keyword to two types (D1 and D2) literature sets of each literature set types 1 to m of each of the bio-items 1 to r to acquire the number (Nk) of literatures related to the keyword with respect to the data D1 and the number (Nh) of literatures related to the keyword with respect to the data D2 (SD-2 to 3).

The bio-item full text searcher 120 calculates a correlation score of each of the literature set types 1 to m by statistical calculation using a literature table for each of the bio-items 1 to r (SD-4).

The bio-item full text searcher 120 uses the minimum one of the correlation scores of the literature set types 1 to m as a correlation score of each of the bio-items 1 to r. In this case, the bio-item full text searcher 120 may perform control to remove a bio-item in which the minimum correlation score is a predetermined threshold value or larger from an answer of direct searching.

With respect to the processes of the SD-3 to 5, as shown in FIG. 11, in particular, a searching process for the bio-item 1 will be described below. More specifically, as shown in FIG. 11, the bio-item full text searcher 120 searches with a keyword by the process of the full text searcher 110 in each of the literature set types 1 to m of the bio-item 1 to acquire the numbers of literatures (Nk in D1 and Nh in D2) each including the keyword for each of the literature set types 1 to m (SD-3). The bio-item full text searcher 120 creates the number-of-literatures table by using any one of the number-of-literatures Nh and the number-of-literatures Nk or both, and calculates a correlation score between the bio-item 1 and the keyword for each of the literature set types 1 to m based on statistical calculation (SD-4). The bio-item full text searcher 120 uses a minimum correlation score of the correlation scores between the bio-item 1 and the keyword calculated with respect to the literature set types 1 to m as a correlation score to the keyword of the bio-item 1 (SD-5). In this case, the bio-item full text searcher 120 may exclude a bio-item in which a minimum correlation score is the threshold value or larger from the answer (SD-5).

As shown in FIGS. 11 and 12, the bio-item full text searcher 120 also executes the processes in the SD-3 to 5 with respect to items 2 to r to collect answers (SD-3 to 5). In this case, the correlation score indicates a P value ($0 \leq P \leq 1$) calculated based on a Fisher's exact test on a null hypothesis. As the null hypothesis, a hypothesis in which "a keyword is not related to appearance of a bio-item in a literature set" is set. More specifically, when the P value is sufficiently small, the null hypothesis is rejected. For this reason, a small correlation score means that the bio-item closely correlates with the keyword. Extraction of a bio-item i (candidate bio-item) in which the minimum correlation score is the threshold value or less means that a bio-item having significantly high correlation with the keyword is selected.

Furthermore, in the process in SD-3 to 5, with respect to each of the bio-items 1 to r, any one of the literature set types 1 to m or all the number-of-literatures tables are integrated to generate a new number-of-literatures table. By using the number-of-literatures tables, a correlation score between the bio-item and the keyword may be calculated based on statistical calculation. More specifically, with respect to each of the bio-items 1 to r, the number-of-literatures table shown in FIG. 2 is created for each of the literature set types 1 to m. However, a new number-of-literatures table constituted by a value A obtained by summing up all terms a of the number-of-literatures tables of the literature set types 1 to m, a value B obtained by summing up all terms b, a value C obtained by summing up all terms c, and a value D obtained by summing up all terms d (in FIG. 2, a table in which a value A is assigned to a, a value B is assigned to b, a value C is assigned to c, a value D is assigned to d) may be generated. The number-of-literatures table constructed as described above will be called an integrated number-of-literatures table in the following explanation.

Alternatively, at least one literature set type for which the integrated number-of-literatures table is created is arbitrarily selected from the literature set types 1 to m to generate an integrated number-of-literatures table. By using the integrated number-of-literatures table, a correlation score between a bio-item and a keyword is calculated, and a correlation score between a bio-item and a keyword is calculated from the number-of-literatures table for each of the literature set types for which the integrated number-of-literatures table is not created. A minimum correlation score may be selected as a correlation score of the bio-item from these correlation scores. Although the method of generating an integrated number-of-literatures table and calculating a correlation score is described above, the present invention is not limited to the correlation score calculating method.

Figure 24:
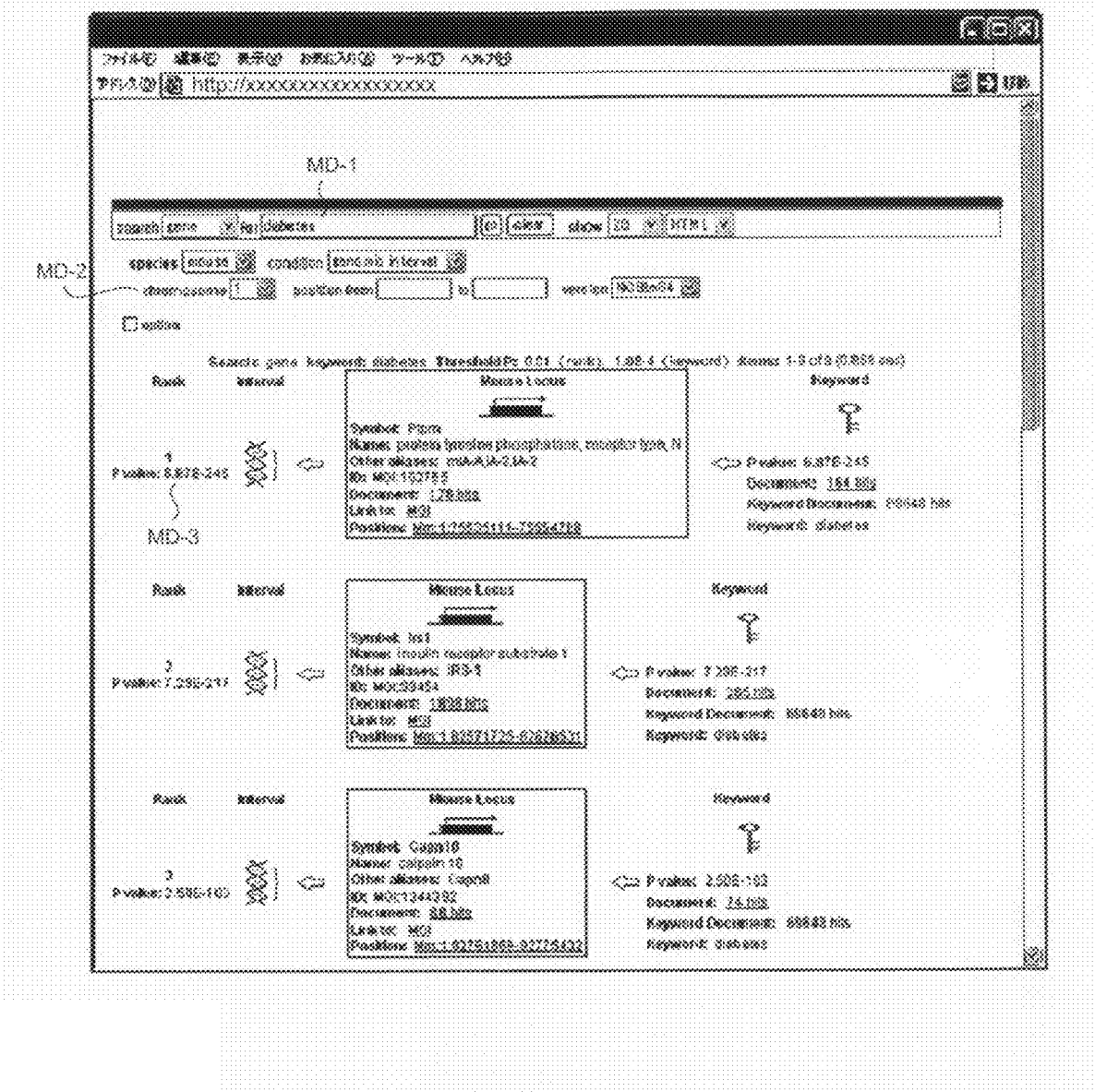
FIG. 24 is a diagram showing an example of a document direct searching result display screen in the single interval mode.

When a bio-item i is extracted as an answer by the bio-item full text searcher 120, as shown in FIG. 10 and FIG. 12, with respect to each bio-item i selected as an answer, the bio-item searching system determines, with reference to the position information database 106d or the identifier information database 106e, whether a position on a genome of each bio-item i is present in an interval (including a sequence of identifiers or the like) input by a user (SD-6). When the bio-item full text searcher 120 determines that the bio-item is present in the interval (SD-6, Yes), the bio-item searching system shifts the process to steps subsequent to SD-9 to output the bio-item to the output device based on the correlation score. More specifically, the answer output here, serves as an answer obtained by direct searching. An example of a result display screen of the direct searching will be explained with reference to FIG. 24. FIG. 24 is a diagram showing an example of the result display screen of the direct searching.

As shown in FIG. 24, a user inputs "diabetes" to a keyword input field (MD-1) and specifies a "first" chromosome for an interval input field (MD-2). In this example, "Ptprn" is given as a candidate bio-item at the top of the direct searching result, and the correlation score (P-value) of the bio-item is output as "6.87e-245" to a correlation score display field (MD-3). The candidate bio-items are arranged in an ascending order of correlation scores, i.e., in a descending order of degrees of correlation (6.87E-245<7.29E-217<2.50E-103).

Returning to the explanation of SD-6, as shown in FIGS. 10 and 12, when it is determined a position on a genome of the bio-item serving as an answer is not present in the interval (SD-6, No), a related bio-item related to the bio-item is extracted by referring to the bio-item relation database 106c (SD-7).

The bio-item searching system determines whether a position on a genome of the related bio-item of the extracted related bio-items is present in the interval input by the user, and shifts to the process subsequent to SD-9 with respect to the related bio-item present in the interval (SD-8, Yes). More specifically, when an answer obtained by inference of a bio-item is calculated, the user can obtain an answer of indirect searching which satisfies the interval even when the direct searching result does not satisfy the interval.

The bio-item searching system integrates a correlation score (co-occurrence correlation score) between the bio-item and the related bio-item with a correlation score between the keyword and the bio-item to calculate a new correlation score (integrated correlation score) by the process of the integrated correlation score calculating unit 102*h* (SD-9). When the bio-item searching system determines, as a result of calculation by the process of the integrated correlation score calculating unit 102*h*, that the integrated correlation score satisfies a predetermined level (predetermined threshold level or less), the bio-item searching system may reject the null hypothesis to perform control to output the related bio-item as an answer.

The bio-item searching system arranges obtained bio-item (candidate bio-item and related bio-item) groups by the process of the output unit 102*i* based on the correlation score or the integrated correlation score (SD-10), and outputs an HTML document which displays the searching result to the user (SD-11). In this case, FIG. 23 is an example of an indirect searching result display screen in a single interval mode.

Figure 23:
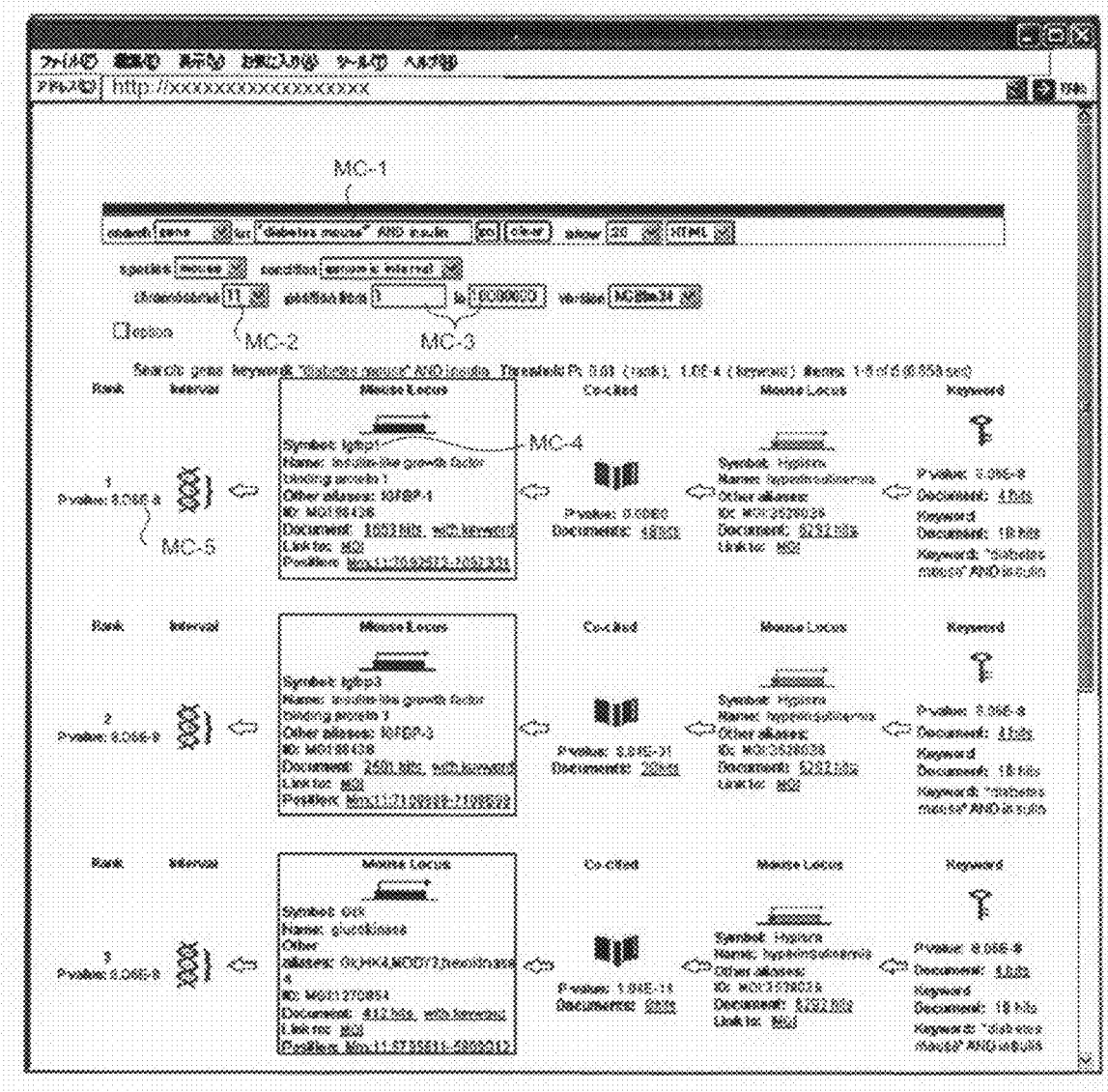
FIG. 23 is a diagram showing an example of a document indirect searching result display screen in the single interval mode.

The example in FIG. 23 depicts an example which searches for a mouse gene by using a literature set type MEDLINE. In the example in FIG. 23, a user inputs "diabetes mouse" and "insulin" to a keyword input field (MC-1), inputs "11" to a chromosome number input field (MC-2) in an interval input field, and sets "1" to "10000000" (bps) in a position input field (MC-3).

According to the searching result in FIG. 23, the related bio-item groups are rearranged according to integrated correlation scores (P values) between keywords and bio-items and output. In the top bio-item display field (MC-4), a related bio-item "Igfbp1" related to a candidate bio-item "Hypism", and "8.06E-8" is displayed in an integrated correlation score display field (MC-5).

This is the single interval mode searching. A bio-item relationship will be described below. The bio-item relationship is any one of the followings.

1) The bio-item relationship means two bio-items co-occurring on one literature, and a two-dimensional number-of-literatures table ("number-of-co-occurrence-literatures table") and a correlation score ("co-occurrence correlation score") between the two bio-items are calculated in advance. In this case, when the two bio-items are represented by bio-item 1 and bio-item 2 respectively, the number-of-co-occurrence-literature table is a two-dimensional table constituted by values of four items: A: the number of literatures each including both a name of bio-item 1 and a name of bio-item 2, B: the number of literatures each including the name of the bio-item 1 and not including the name of the bio-item 2, C: the number of literatures each not including the name of the bio-item 1 and including the name of the bio-item 2, and D: the number of literatures each not including the name of the bio-item 1 and not including the name of the bio-item 2. According to the number-of-co-occurrence-literature table, statistical calculation such as a test, for example, a Fisher's exact test is performed to calculate a P value as a co-occurrence correlation score. At this time, with respect to a direction of the bio-item relationship, only a relationship expressed by bio-item 1→bio-item 2 is given when B=0 and C≠0, only a relationship expressed by bio-item 2→bio-item 1 is given when B≠0 and C=0, and a bidirectional relationship expressed by bio-item 1⇔bio-item 2 is given in the other conditions.

2) The relationship means two bio-items the relativity of which is found by an experiment or the like. At this time, the correlation score is given as the P value. The bio-item relationship is not always required to have a direction. More specifically, even when there is a mono-directional relativity between two bio-items i1 and i2 expressed by i1→i2 or i1←i2, there may be a bi-directional relativity expressed by i1⇔i2. However, in inference of a bio-item in the single interval mode, when a bio-item of an inference source and a bio-item of an inference destination are represented by io and id, respectively, only a bio-item relationship: io→id is applied.

b. Single Interval Mode Searching to Catalog Set

Figure 13:
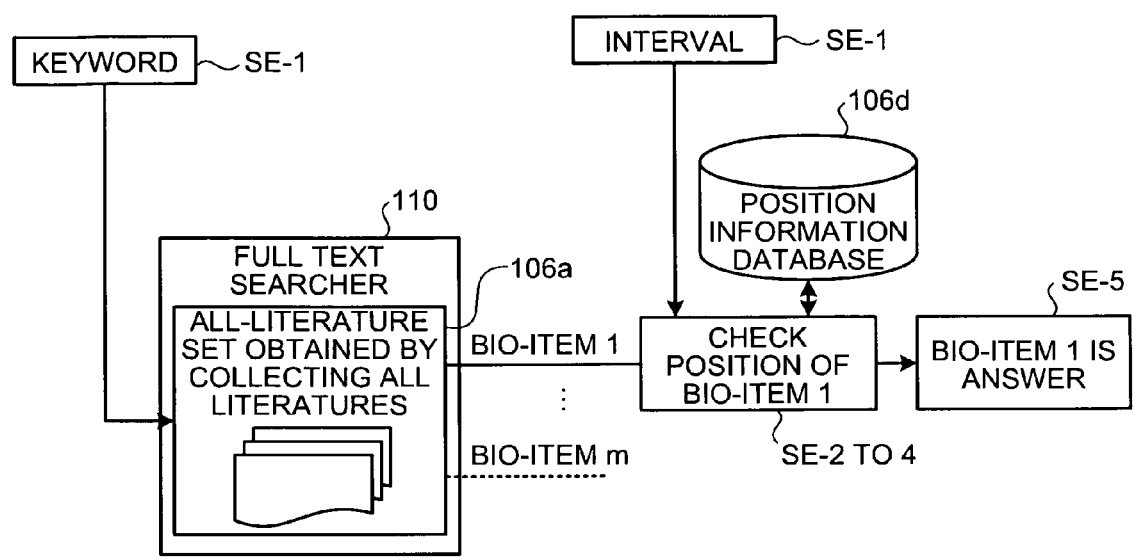
FIG. 13 is a diagram showing a flow of data when a bio-item is searched in a catalog set in the single interval mode.
Figure 14:
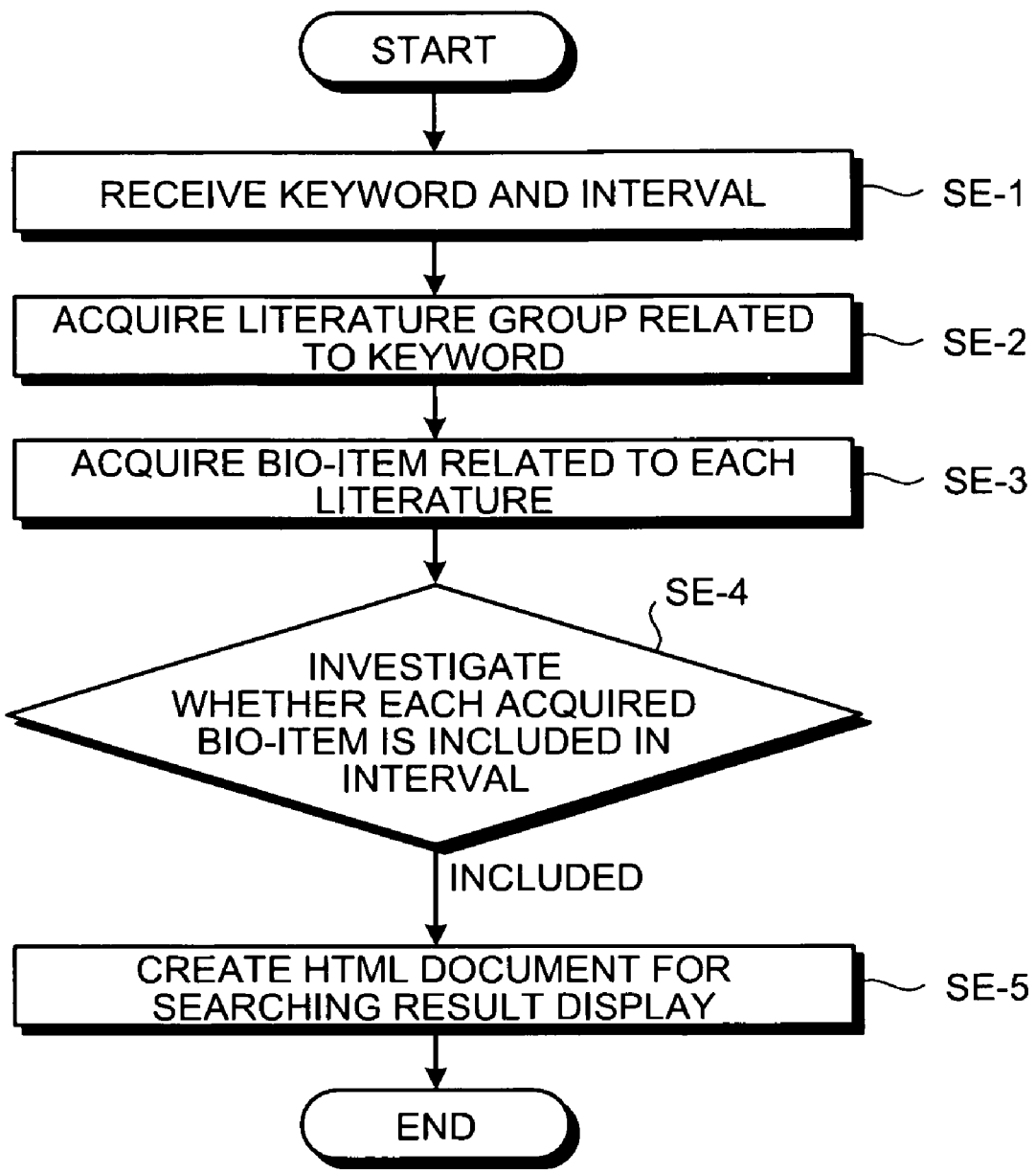
FIG. 14 is a flow chart showing an operation when a bio-item is searched in a catalog set in the single interval mode.

An example of a single interval mode searching process to a catalog set will be explained by using FIGS. 13, 14, and 21. When a literature set is a catalog set, a bio-item and a literature is stored in a one-to-one relationship. FIG. 13 is a diagram showing a flow of data when a bio-item is searched for with respect to a catalog set in a single interval mode. FIG. 14 is a diagram showing the operation as a flow chart.

When a literature set is a catalog set, the full text searcher 110 includes the all-literature set file 106*a* which stores an all-literature set having all catalog literatures. The all-literature set file 106*a* may include an all-literature set file for each of a plurality of catalog set types or include one all-literature set file obtained by collecting all-literature sets of all the catalog set types. When the full text searcher 110 receives a keyword and an interval (SE-1), the full text searcher 110 searches all the catalog sets (corresponding to the all-literature set) to acquire a literature related to the keyword (SE-2). The full text searcher 110 acquires a bio-item related to each literature as a result of searching (SE-3).

When the literature set is a catalog set, the full text searcher 110 does not store a bio-item literature set. For this reason, the number of literatures to calculate a correlation score is not acquired. At this time, a correlation score between a keyword and a bio-item is defined as 0 for convenience, and "0 is always derived.

Thereafter, the control device of the bio-item searching system determines, by the process of the genome region determining unit 102*j*, whether a retrieved bio-item is present in the interval (SE-4).

When it is determined by the process of the genome region determining unit 102*j* that the bio-item is present in the interval, the control device outputs the bio-item determined to be present in the interval as an answer by the process of the output unit 102*i* (SE-5). In this case, FIG. 21 is a diagram showing an example of a result display screen of single interval mode searching to the catalog set.

Figure 21:
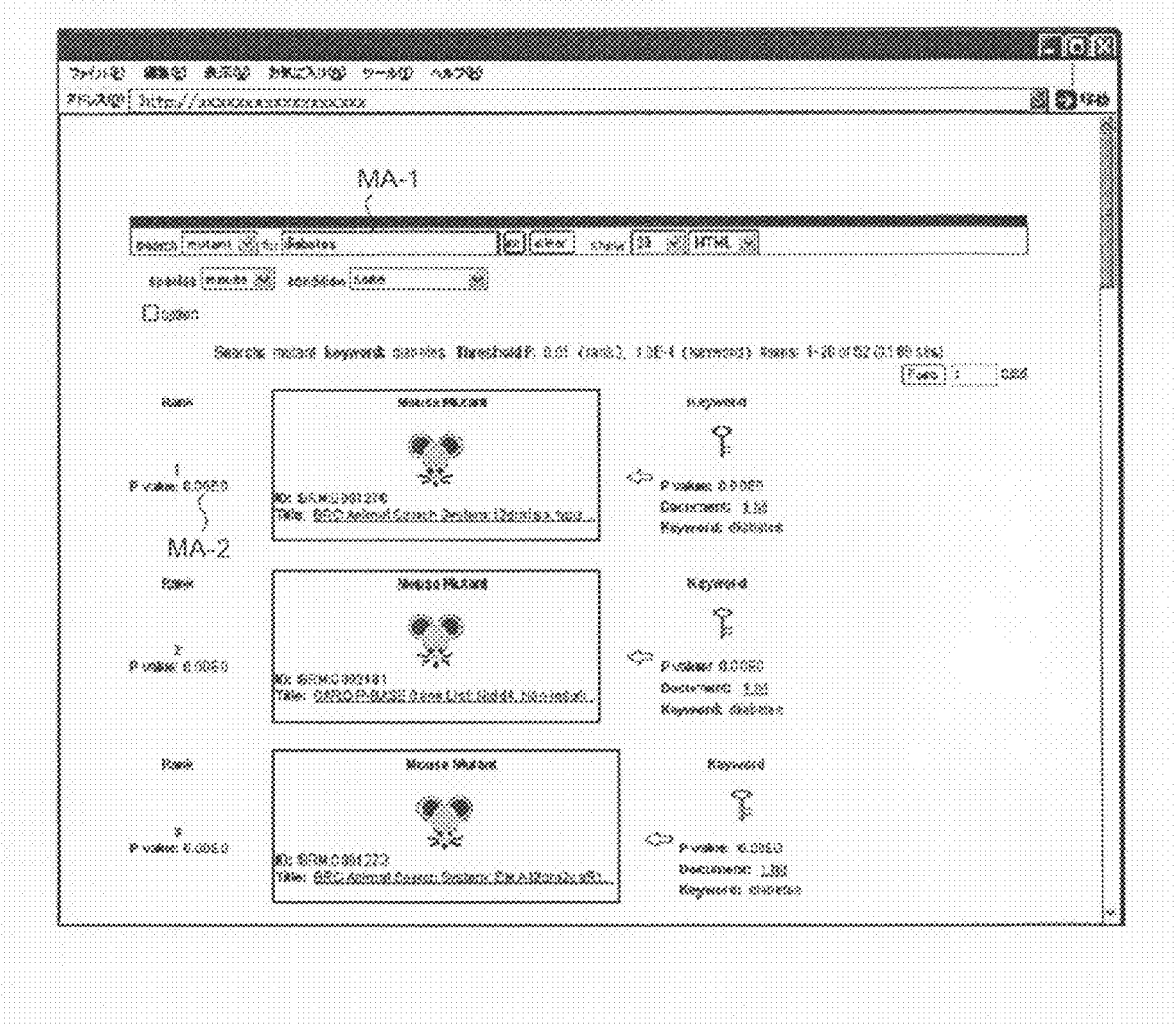
FIG. 21 is a diagram showing an example of a catalog searching result display screen in the single interval mode.

FIG. 21 depicts an example in which a mutant mouse is searched for by using a catalog set type mouse bio-resource catalog. In the result display screen shown in FIG. 21, a user inputs "diabetes" in a keyword input field (MA-1) (in this example, an interval is not specified), a correlation score (P value) display field (MA-2) in the result of the catalog searching is output as 0.00E0.

c. Multiple Interval Mode Searching

Figure 15:
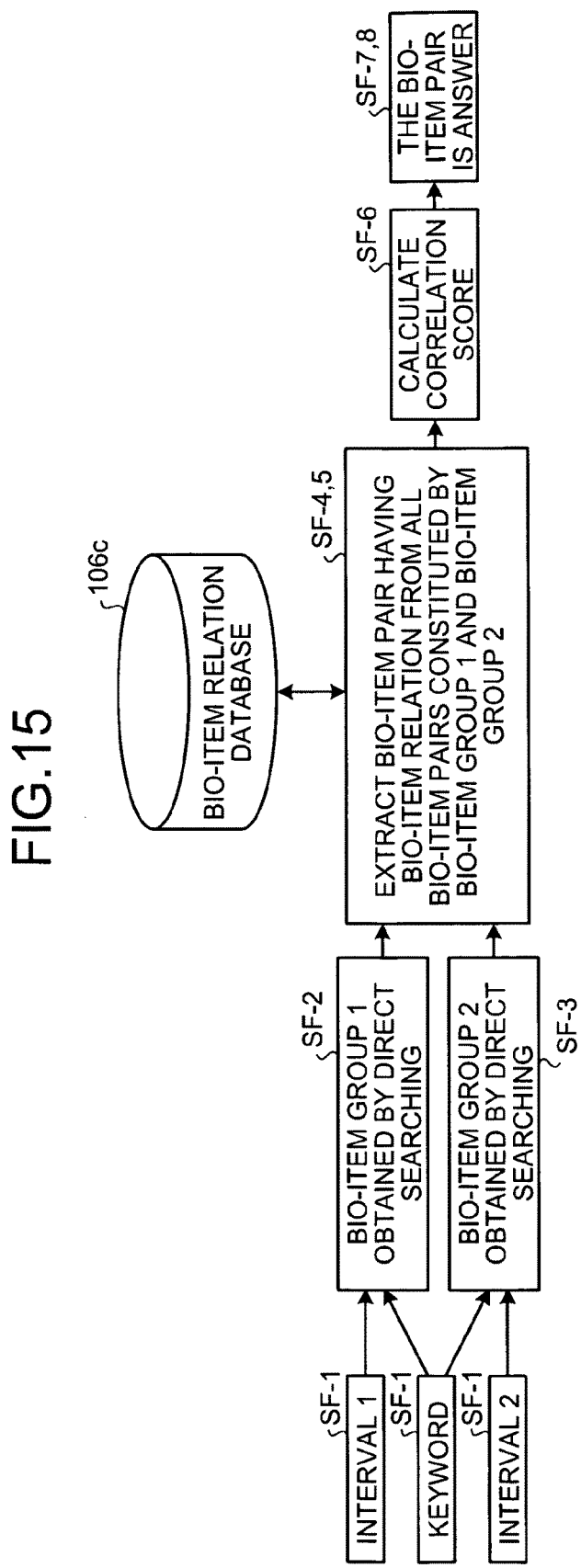
FIG. 15 is a conceptual diagram showing a flow of data in multiple interval mode searching.
Figure 16:
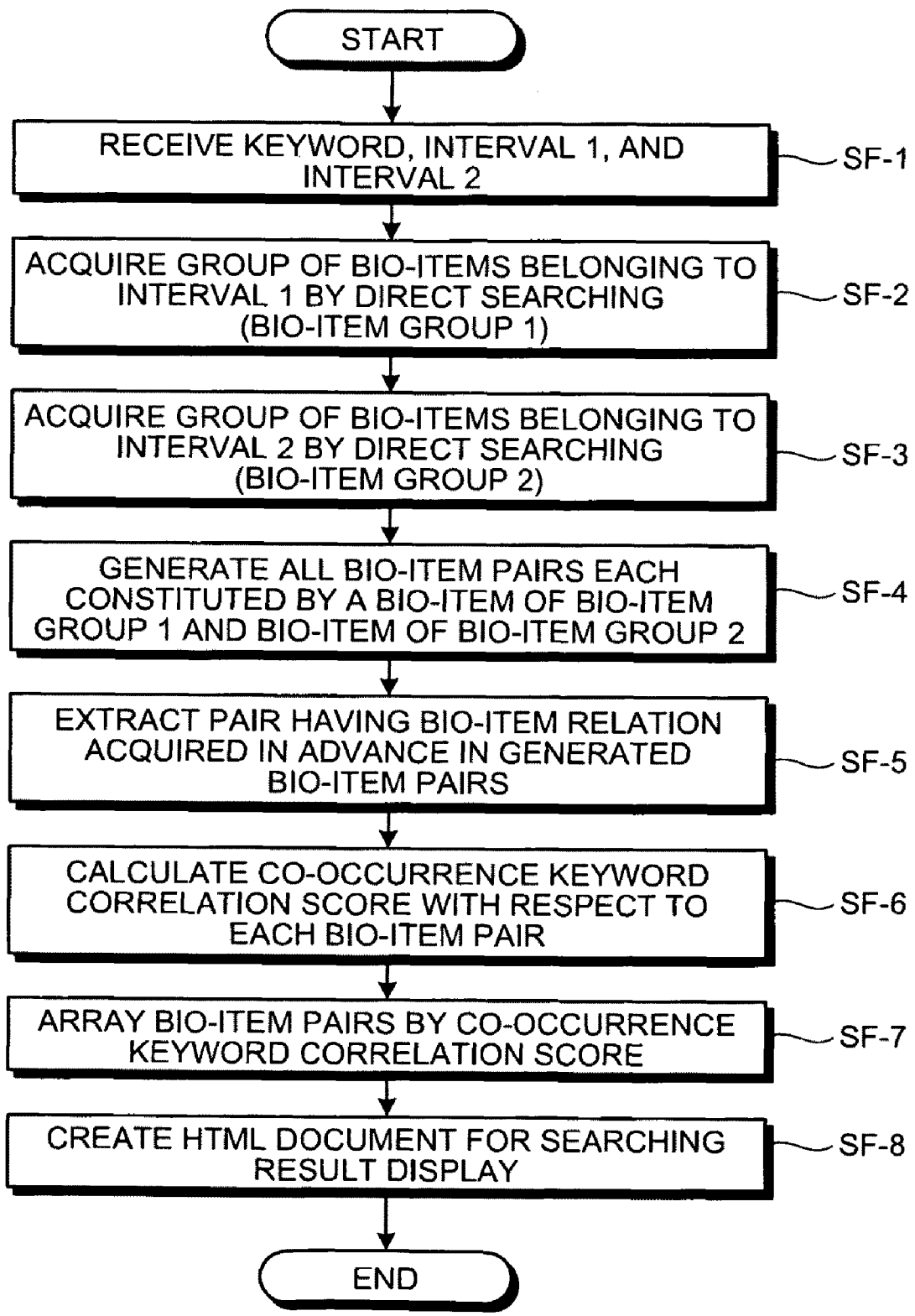
FIG. 16 is a flow chart showing an operation of the multiple interval mode searching.

Searching in a multiple interval mode will be explained with reference to FIGS. 15, 16, and 22. In the searching in the multiple interval mode, searching for a bio-item is not performed to a catalog set, and searching for a bio-item is performed to a document set. In this case, the two intervals input to the bio-item searching system by a user are called "interval 1" and "interval 2", respectively. FIG. 15 is a conceptual diagram showing a flow of data in multiple interval mode searching. FIG. 16 is a flow chart showing the operation.

As shown in FIGS. 15 and 16, when a keyword, the bio-item 1, and the bio-item 2 are received (SF-1), the bio-item searching system performs direct searching with the keyword to a document set with respect to the interval 1 and the interval 2 (SF-2 and 3). More specifically, a group of answers of direct searching which satisfy the interval 1 is acquired as bio-item group 1, and a group of answers of direct searching which satisfy the interval 2 is acquired as bio-item group 2. In this case, since processing contents of the direct searching are explained above, an explanation thereof will be omitted.

The bio-item searching system generates all combinations of bio-items constituted by a bio-item belonging to the bio-item group 1 and a bio-item belonging to the bio-item group 2 as bio-item pairs (SF-4).

The bio-item searching system extracts a bio-item pair having a predetermined bio-item relationship (for example, a co-occurrence correlation score is a threshold value or less) with reference to the bio-item relation database 106c (SF-5). In this case, the bio-item relationship is expressed by i2→i2, i1←i2, or i1⇔i2 when the bio-item pair is expressed by i1 and i2. However, the relationship between i1 and i2 may have any direction.

The bio-item searching system integrates correlation scores among two bio-items and the keyword calculated for each of the extracted bio-item pairs and a co-occurrence correlation score between the bio-items of the bio-item pair, based on the numerical expression 2, the numerical expression 3, or the like to calculate a new correlation score (co-occurrence keyword correlation score) (SF-6). In this case, the bio-item searching system may reject the null hypothesis and perform control to output the bio-item pair as an answer when it is determined as a result of calculation by the process of the co-occurrence keyword correlation score calculating unit 102m that the co-occurrence keyword correlation score satisfies a predetermined level.

The bio-item searching system arranges the bio-item pair groups obtained as answers by the process of the output unit 102i based on a total correlation score (co-occurrence keyword correlation score) (SF-7) and shows the bio-item pair groups to a user (SF-8). In this case, an example of a searching result display screen in the multiple interval mode will be explained with reference to FIG. 22. FIG. 22 is a diagram showing an example of a multiple interval searching result display.

Figure 22:
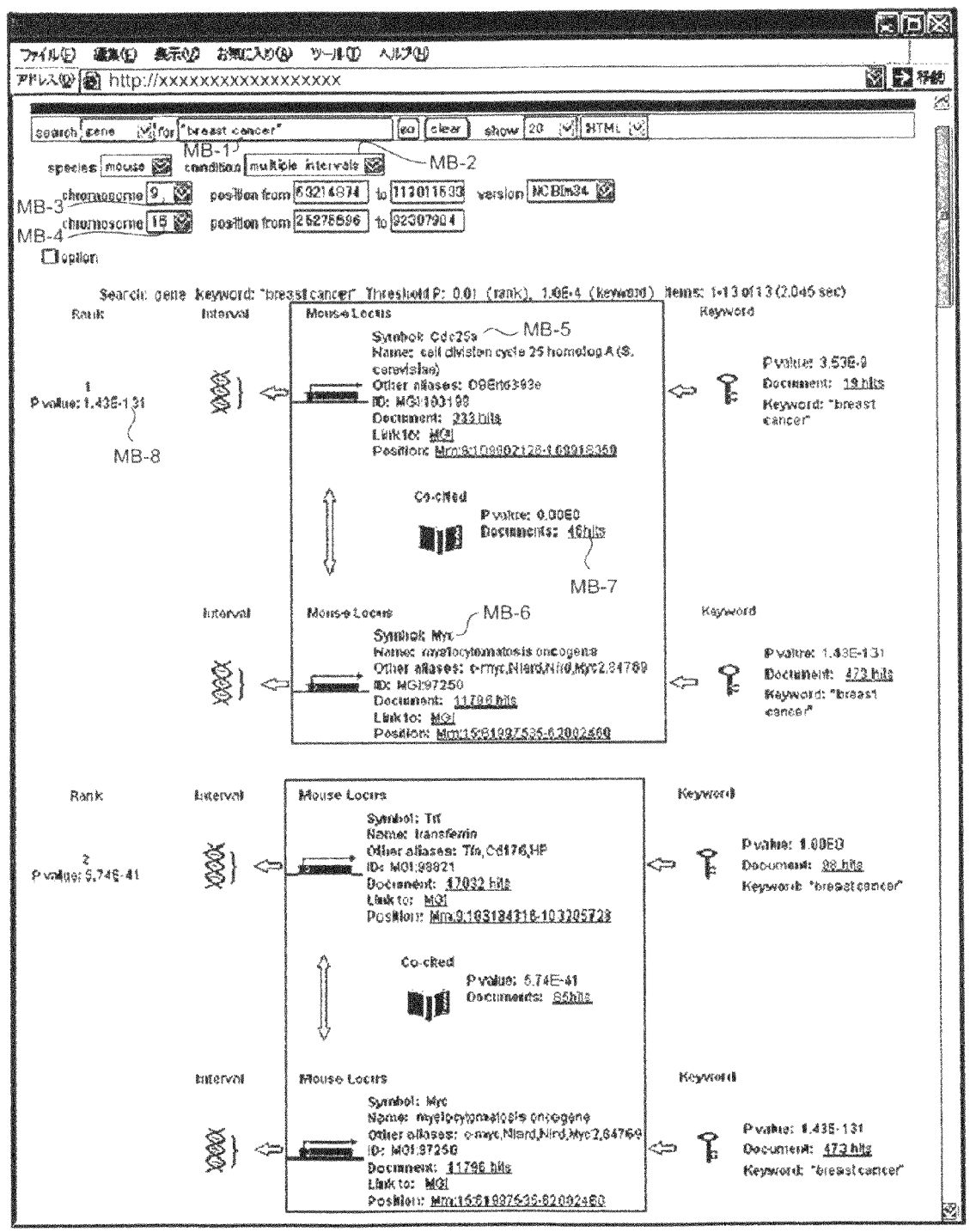
FIG. 22 is a diagram showing an example of a document searching result display screen in a multiple interval mode.

FIG. 22 depicts an example in which a mouse gene is searched for by using a literature set type MEDLINE. In the example shown in FIG. 22, a mode setting field (MB-2) is set in a multiple interval mode ("multiple intervals"), and a user inputs. "breast cancer" to a keyword input field (MB-1), inputs a region ("63214874" to "111011533") on the "ninth" chromosome to an interval 1 input field (MB-3), and inputs a region ("25275696" to "92307904") on the "15th" chromosome to an interval 2 input field (MB-4).

When the inputs are performed by the user, as shown in FIG. 22, as the top searching result, "Cdc25a" is displayed as a searching result on a bio-item 1 result display field (MB-5), and "Myc" is displayed as a searching result on a bio-item 2 result display field (MB-6). In a number-of-documents display field (MB-7) including both the bio-items (Co-cited), "46 cases" is displayed. In a correlation score (total P value) display field (MB-8) obtained by integrating both the bio-items, "1.43E-131" is displayed. In the multiple interval mode, the user can obtain a bio-item pair having a totally high correlation and formed in consideration of a genome region.

This is the example in which the searching methods of two types using the multiple interval mode and the single interval mode are executed.

Implementation of Bio-item Searching System

An implementation of a bio-item searching system in which the embodiment of the present invention is applied to a practical distributed architecture will be explained with reference to FIG. 17. According to the embodiment, searching functions are designed to be operated on a plurality of computers which are distributed. For this reason, when the searching functions perform processes in parallel to each other, a processing time can be shortened, and a series of searching operations are completed within several seconds to one second. In this case, FIG. 17 is a diagram showing an example of a system-architecture of a bio-item searching system.

Figure 17:
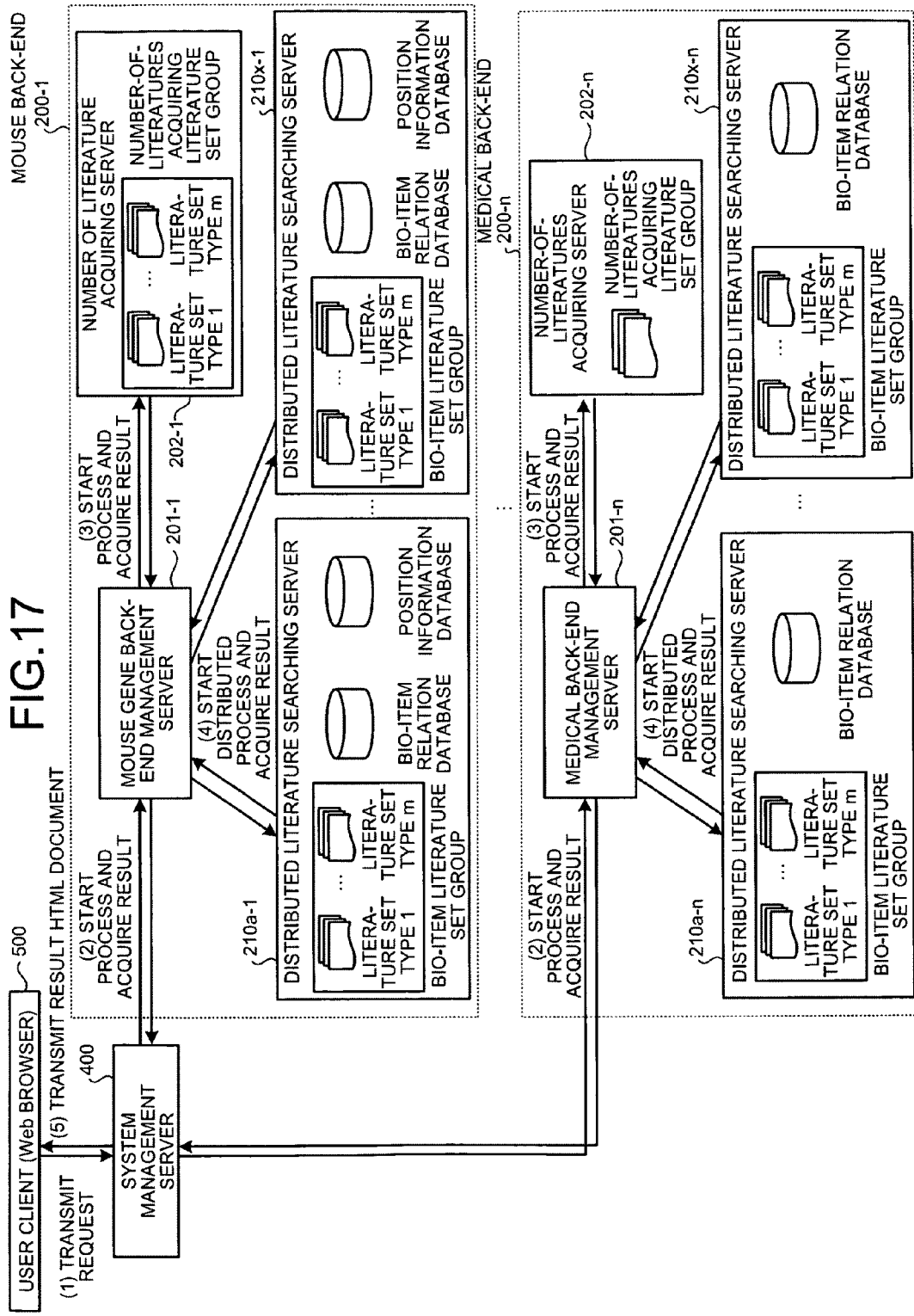
FIG. 17 is a diagram showing an example of a document searching system architecture.

As shown in FIG. 17, the bio-item searching system is roughly constituted by three software components. More specifically, the bio-item searching system, as shown in FIG. 17, includes a user client 500, a system management server 400, and a back-end 200. Furthermore, the back-end 200 includes a back-end management server 201, a number-of-literatures acquiring server 202, and distributed literature searching servers 210a to x which are distributed. The system management server 400 is connected to a plurality of back-ends 200-1 to n constructed for the bio-item types 1 to n (mouse gene, human gene, medical agent, metabolite, bio-resource, disease, and the like), respectively, and executes a distributed parallel processing between the back-ends as needed. In FIG. 17, a mouse back-end 200-1 and a medical agent back-end 200-n are exemplified. A bio-item, for example, a medical agent which is free from a genome sequence is handled as a virtual gene which does not have a position on a genome sequence. Operational procedures of the bio-item searching system will be explained below.

(1) Transmission of User Request

The user client (web browser) 500 causes a user to input a keyword, an interval, a sequence of identifiers, or the like. In this case, although the user can input the interval, the sequence of identifiers, or both the interval and the sequence of identifiers, even when only an "interval" is described, it expresses any one of the interval and the sequence of identifiers or both the interval and the sequence of identifiers. The user client 500 transmits these request data input by the user to the system management server 400.

(2) Start of Request Process of Processing to Back-End and Acquisition of Result The system management server 400 that receives request data analyzes a request, selects the back-end 200 to be requested to perform the processing, and transmits the request to the back-end management server 201 of the selected back-end 200.

(3) Start of Acquiring Process of the Number of Literatures Related to Keyword and Acquisition of Result The back-end management server 201 which receives the request transmits a keyword to the number-of-literatures acquiring server 202. The number-of-literatures acquiring server 202 which receives the keyword acquires a combination between the number (Nk) of literatures related to the keyword and the number (¬Nk) of literatures which is not related to the keyword for each of the literature set types 1 to m by using a number-of-literatures acquiring literature set (all-literature set) group to return the combinations to the back-end management server 201.

(4) Start of Literature Searching Process by Distributed Parallel Processing and Acquisition of Result The back-end management server 201 transmits the request received in (2) and the combinations of the number of literatures obtained in (3) to the distributed literature searching servers 210a to x to request the literature searching servers 210a to x to perform a literature searching process.

Operation of Distributed Literature Server in Document Set of One Type

Figure 19:
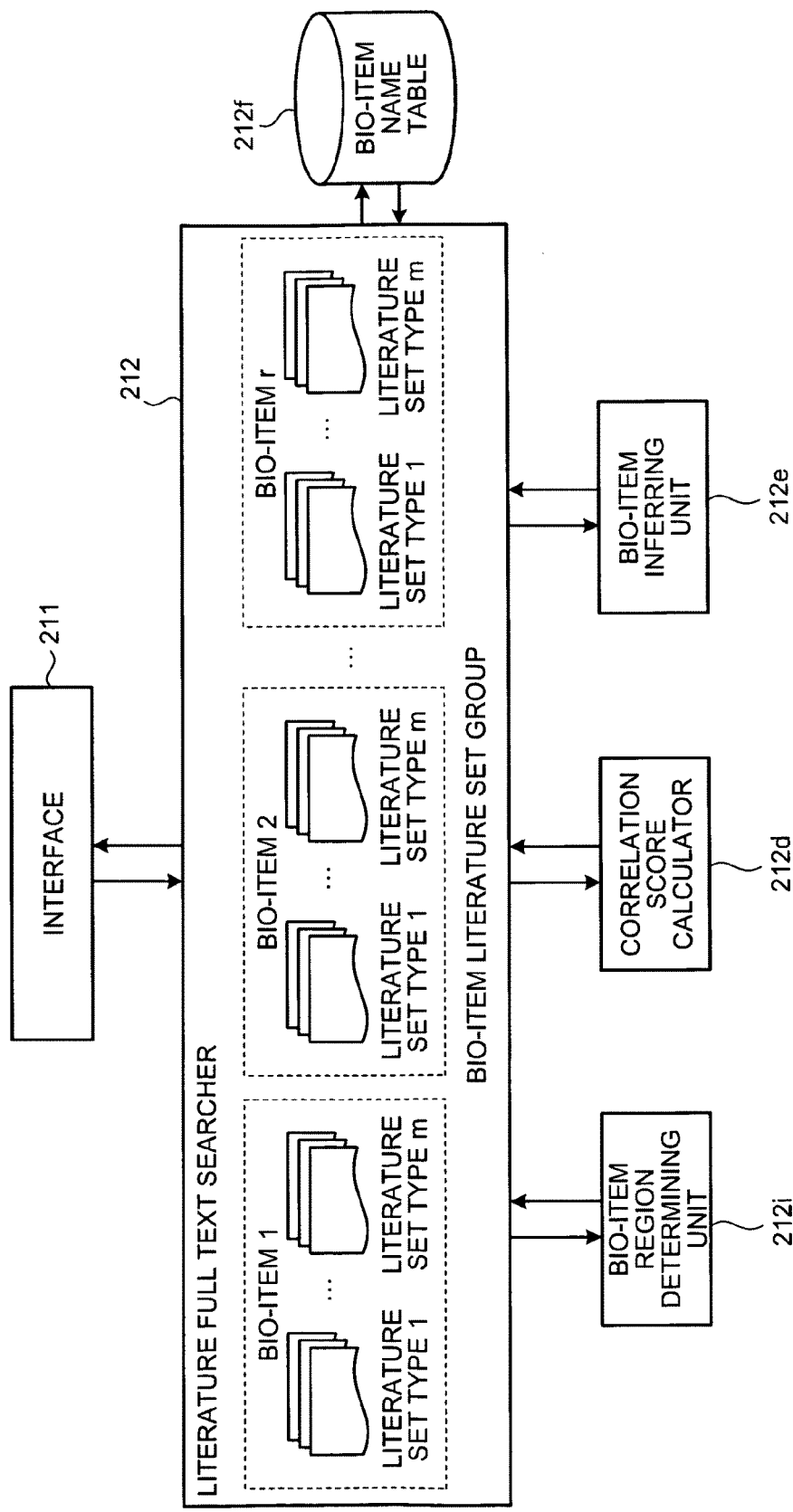
FIG. 19 is a diagram showing an example of an architecture of a distributed literature searching server.

An operation of a back-end when a literature set type is of one type and the literature set type is a document set will be described below with reference to FIGS. 17 and 19. More specifically, the operation of each of the distributed literature searching servers 210 is as follows. FIG. 17 is a diagram showing an example of a system-architecture of the bio-item searching system. FIG. 19 is a diagram showing an example of an architecture of the distributed literature searching server 210.

(1) The back-end management server 201 receives a combination between the request (keyword, interval, sequence of identifiers, or the like) obtained from the back-end management server 201, the number-of-literatures Nk obtained from the number-of-literatures acquiring server 202 and related to a keyword, and the number-of-literatures ¬Nk which are not related to the keyword through the interface 211 and transmits the combination to the literature full text searcher 212.

(2) The literature full text searcher 212 performs full-text searching by the keyword to a related literature set (the number of literature is N1) of the bio-item 1 to acquire the number-of-literatures Nh related to the bio-item 1. When the number-of-literatures Nh is 1 or larger, the bio-item region determining unit 212i checks whether the bio-item 1 is present in an interval.

(i) When it is determined that the bio-item 1 is included in the interval, the bio-item region determining unit 212i employs the bio-item 1 as a searching result to execute (3). More specifically, the bio-item region determining unit 212i transmits a combination between an identifier of the bio-item 1 and a P value of the bio-item 1 and the keyword obtained in (3) and calculated by the process of the correlation score calculator 212d to the literature full text searcher 212.

(ii) When the bio-item region determining unit 212i determines that the bio-item 1 is not included in the interval, the literature full text searcher 212 extracts a bio-item x related to the bio-item 1 by using a bio-item inferring unit 212e to acquire a correlation score $P_{g1-gx}$ (co-occurrence correlation score) between the bio-item 1 and the bio-item x. When it is determined that the bio-item x is present in the interval, the control device employs the bio-item x as a searching result, calculates a correlation score between the bio-item x and the keyword by the process of the correlation score calculating unit 102d, and calculates an integrated P value by integrating the correlation score and the co-occurrence correlation score. When this integrated P value is lower than a predetermined level, the bio-item inferring unit 212e transmits the combination between an identifier of the bio-item x and the integrated P value to the literature full text searcher 212.

In this case, in the determination whether the bio-item 1 is present in the interval, even when a species of the bio-item is different from a species of a genome sequence in a region (interval) specified by a user, when there is a homology relationship, this relationship may be applied.

(3) The distributed literature full text searcher 212 transmits Nh, N1, Nk, and ¬Nk (=Nall−Nk) to the correlation score calculator 212d. The correlation score calculator 212d creates a number-of-literatures table shown in FIG. 3, and calculates a P value from the table by statistical calculation such as a Fisher's exact test, a chi-square test, or a Bayes conditional probability.

(4) The literature full text searcher 212 executes (2) and (3) with respect to the other bio-items, i.e., from the bio-item 2 to the bio-item r.

(5) The literature full text searcher 212 returns a list of combinations between bio-items and P values obtained as a searching result to the back-end management server 201 through the interface 211.

In this case, an operation of the distributed literature searching server 210 in the multiple interval mode will be explained below.

To search for a bio-item present in the interval 1, operations in the single interval mode are executed in the order of (1), (2)(i), (3), (4), and (5).

To search for a bio-item present in the interval 2 to obtain a result, the following operations are performed.

(6) The interface 211 receives a request, i.e., the keyword and the interval from the back-end management server 201, the list obtained in (5), and a combination of the number (Nk) of literatures related to the keyword and the number (¬Nk) of literatures related to the keyword which are obtained from the number-of-literatures acquiring server to transmit the request and the combination to the literature full text searcher 212.

(7) The literature full text searcher 212 executes (2)(i) to the bio-item 1 and the bio-item 2.

(8) The literature full text searcher 212 creates all pairs between the bio-item group obtained in (5) and the bio-items. The literature full text searcher 212 executes the following to each of the bio-item pairs.

(i) It is assumed that bio-items constituting the pair are represented by $g_1$ and $g_x$, respectively. This pair is transmitted to the bio-item inferring unit 212e.

(ii) The bio-item inferring unit 212e checks, based on, for example, a co-occurrence correlation score, whether there is a relationship between the two bio-items constituting the bio-item pair received. When there is a relationship, the bio-item inferring unit 212e acquires a two-dimensional number-of-literatures table $T_{g1-gx}$ and a correlation score $P_{g1-gx}$ between the two bio-items. The bio-item inferring unit 212e transmits a combination $<T_{g1-gx}, P_{g1-gx}>$ to the literature full text searcher 212.

(9) The literature full text searcher 212 executes (3) to a bio-item to calculate a correlation score by the keyword. The literature full text searcher 212 calculates a total correlation score $P_{total}$ with respect to the combination received in (8) by using the numerical expression 2 or the numerical expression 3. When the total correlation score $P_{total}$ is lower than a predetermined level, a 6-piece combination including the bio-item x, the bio-item 1, the scores $P_{total}, P_{g1}, P_{g1-gx}$, and the combination received in (8) is transmitted as one of answers to the back-end management server 201.

(10) The literature full text searcher 212 executes (7), (8), and (9) to other bio-items.

This is the embodiment of the operation of the distributed literature searching server 210.

Operation of Distributed Literature Server in Catalog Set of One Type

Figure 20:
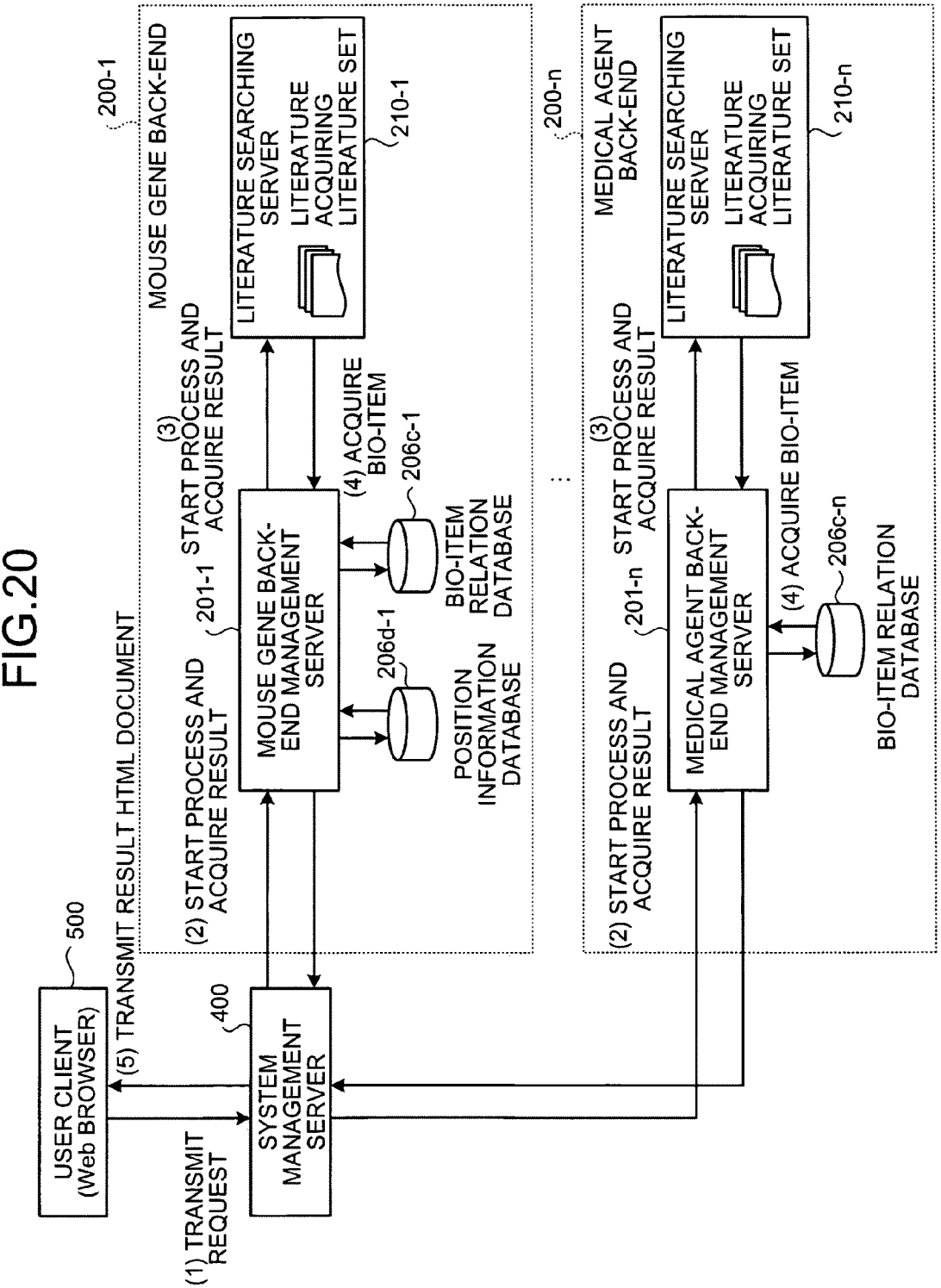
FIG. 20 is a diagram showing an example of an architecture of a catalog searching system.

An operation of a back-end when a literature set type is of one type and the literature set type is a catalog set will be explained with reference to FIG. 20. FIG. 20 is a diagram showing an example of an architecture of a catalog searching system.

The catalog set searching system is different from the document searching system in the configuration of the back-end 200. The procedure "(1) transmission of user request", "(2) start of request process of processing to back-end and acquisition of result" and "(5) display of searching result by transmission of result HTML document" are the same as the procedures in the document searching system.

(3) Start of Acquiring Process of Literature Related to Keyword and Acquisition of Result.

The distributed literature searching server 210 acquires a literature related to a keyword. More specifically, the distributed literature searching server 210 stores an all-literature set having all catalog literatures, performs full-text searching to the literature set by the keyword to acquire the literature related to the keyword.

(4) Acquisition of Bio-Item (Selection of Answer Bio-Item)

The back-end management server 201 acquires bio-items corresponding to the literatures obtained in (3) by using the bio-item relation database 206c to select a candidate bio-item. Furthermore, the back-end management server 201, for each of the bio-items, checks, by using the position information database 206d, whether the bio-item is present in the interval. In this case, the bio-item present in the interval is an answer.

This is the architecture of the catalog searching system.

Simultaneous Searching Function to Document Set and Catalog Set

Requests are simultaneously transmitted to the document set searching system and the catalog set searching system, and these results may be integrated to perform bio-item searching by using both the searching systems of the document set and the catalog set. At this time, since a correlation score of the catalog document searching results is always 0, the result of the catalog is always ranked high on a result display page displayed for a user.

Operation of Distributed Literature Server in Literature Set Types of Plurality of Types An operation of a back-end when a plurality of literature set types are used will be explained. In this case, as described above, requests are simultaneously transmitted to a plurality of document set searching systems and a plurality of catalog set searching system, and these results may be integrated. However, the following methods may be used.

An operation in the single interval mode will be explained. Each of the distributed literature searching servers 210 which receives a combination of a request and the number of literatures acquires the numbers of literatures Nh related to a keyword for each of the bio-item groups 1 to r handled by the distributed literature searching server 210 for each of the literature set types 1 to m. With respect to a bio-item in which the number-of-literatures Nh of any one of the literature set types 1 to m is 1 or larger, the following procedures (i) to (ii) will be executed.

(i) When the distributed literature searching server 210 determines, by the process of the genome region determining unit 102j with reference to the position information database, whether a position on a genome of a bio-item (candidate bio-item) in which the number-of-literatures Nh is 1 or larger is present in an interval (region on the genome), the distributed literature searching server 210 calculates a correlation score by statistical calculation based on any one of a combination of the numbers of literatures obtained in (3) and the acquired number-of-literatures Nh or both. When the distributed literature searching server 210 determines that the correlation score is lower (predetermined threshold value or less) than a predetermined significant level, the null hypothesis is rejected, and the distributed literature searching server 210 returns the bio-item as an answer to the back-end management server 201.

(ii) When the distributed literature searching server 210 determines, by the process of the genome region determining unit 102j, that the bio-item (candidate bio-item) in which the number-of-literatures Nh is 1 or larger is not present in an interval specified by a user, the distributed literature searching server 210 applies a bio-item-to-bio-item relationship (for example, based on a co-occurrence correlation score) acquired from a literature in advance to acquire a bio-item (related bio-item) related to the bio-item.

The distributed literature searching server 210 checks, by the process of the genome region determining unit 102j, whether each of the related bio-items (each related bio-item) is present in the interval. When the bio-item is determined to be present in the interval, the distributed literature searching server 210 calculates a correlation score of an original candidate bio-item by statistical calculation based on the combinations of the numbers of literatures obtained in (3). The distributed literature searching server 210 integrates a value of the correlation score with the correlation score (co-occurrence correlation score) of the bio-item-to-bio-item relationship to calculate a total correlation score (integrated correlation score) and returns the related bio-item as an answer to the back-end management server 201.

The back-end management server 201 receives searching results (answers) obtained from all the distributed literature searching servers 210a to x by the processes in (i) and (ii) and returns the results to the system management server 400.

Operations (i) to (v) in the multiple interval mode will be explained below. It is assumed that the two intervals are defined as interval 1 and interval 2, respectively.

(i) The distributed literature searching server 210 which receives the request and the combination of the numbers of literatures from the back-end management server 201 acquires the number (Nh) of literatures related to a keyword for each of the literature set types 1 to m for each of the bio-items 1 to r handled by the distributed literature searching server 210. With respect to a bio-item (candidate bio-item) in which the number-of-literatures Nh of any one of the literature set types 1 to m is 1 or larger, the following procedure is executed.

(ii) When the distributed literature searching server 210 determines that the bio-item (candidate bio-item) is present in the interval 1, the distributed literature searching server 210 calculates a correlation score between the keyword and the bio-item by statistical calculation based on any one of the combination of the numbers of literatures obtained in (3) and the acquired number-of-literatures Nh or both. When the distributed literature searching server 210 determines that the correlation score is lower than the predetermined significant level (predetermined threshold value), the null hypothesis is rejected, and the distributed literature searching server 210 returns the bio-item (candidate bio-item) to the back-end management server 201 as a bio-item present in the interval 1.

The back-end management server 201 receives searching results (answers) from all the literature searching servers 210a to x and transmits the request received in (2) and the three combinations of the numbers of literatures obtained in (3) to the distributed literature searching servers 210a to x to request the literature searching servers 210a to x to perform literature searching processes. The literature searching servers 210a to x execute the following procedures (iii) to (v).

(iii) Each of the distributed literature searching servers 210 acquires the number (Nh) of literatures related to the keyword for each of the literature set types 1 to m for each of the handled bio-items 1 to r. With respect to each bio-item (each candidate bio-item) in which the number-of-literatures Nh of any one of the literature set types 1 to m, the following procedures will be executed.

(iv) When it is determined that the bio-item (candidate bio-item) is present in the interval 2, each of the distributed literature searching servers 210 calculates a correlation score between the keyword and the bio-item by statistical calculation based on the combination of the number of literatures obtained in (3). When the correlation score is lower than the predetermined significant level (predetermined threshold value), the distributed literature searching server 210 executes (v).

(v) Each of the distributed literature searching server 210 generates all pairs of bio-items present in the interval 1 and the bio-items. Of these pairs, a pair having a bio-item-to-bio-item relationship (stored in the bio-item relation database) acquired from a literature in advance is selected based on a co-occurrence relationship. Furthermore, a correlation score about the selected bio-item pair is calculated by integrating the correlation score calculated in (iv) and the correlation score (co-occurrence correlation score) of the bio-item-to-bio-item relationship. A bio-item in which the correlation score is lower than the predetermined significant level (predetermined threshold value) is returned to the back-end management server 201.

After the back-end management server 201 receives the searching results obtained by the processes in (i) to (v) from all the literature searching servers 210*a* to *x*, the distributed literature searching server 210 returns these searching results to the system management server 400.

(5) Display of Searching Result by Result HTML Document Transmission

After the (4) is executed, the system management server 400 receives the searching results of all the selected back-end management servers 201 and integrates the searching results for each of answer bio-items. At this time, with respect to each of answer bio-items (candidate bio-items or related bio-items) serving as the searching results, a plurality of answers are generally obtained (a plurality of candidate bio-items passing through from a keyword to an answer bio-item are obtained). An answer having the minimum total correlation score is used as an answer of the bio-item. The system management server 400 sorts an obtained answer list in an ascending order of correlation scores, converts the results into HTML documents, and returns the HTML documents to the user client 500.

The system according to the embodiment may be implemented as a Web service. More specifically, the system management server 400 may be implemented as a Web server and receive a request from the Web browser serving as the user client 500 through the Internet and transmit the result in an HTML document format. In this case, an example of a display on the Web browser of the processing result transmitted from the Web server to the user client 500 according to the embodiment will be summarized.

Examples shown in FIGS. 21 to 29 are obtained by executing displays by using 20 distributed workstations each having a 3.6-GHz Xeon (brand name) available from Intel Corporation (registered trademark) as a CPU and a 2 GB memory.

Bio-items to be searched used in the embodiment are a mouse gene, a human gene, a metabolite, a medical agent, a disease name, and a mutant mouse. The numbers of bio-items are as follows. The number of mouse genes is 58,237, the number of human genes is 22,707, the number of metabolites is 9,350, the number of medical agents is 1,015, the number of disease names 1,884, and the number of mouse mutants is 12,280.

Furthermore, the literature set types used here are MEDLINE, PPI, a mutant mouse catalog, OMIM, a mouse gene catalog, a human gene catalog, a metabolite catalog, a medical agent catalog, and a disease name catalog. The numbers of literatures of the literature set types used as inputs of the bio-item searching apparatus are as follows. The MEDLINE has 16,335,424 literatures, the PPI has 22,476 literatures, the mutant mouse catalog has 12,280 literatures, the OMIM has 17,974 literatures, the mouse gene catalog has 58,237 literatures, the human gene catalog has 22,707 literatures, the metabolite catalog has 9,350 literatures, the medical agent catalog has 1,015 literatures, and the disease name catalog has 1,884 literatures.

The total numbers of literatures (the total numbers of literatures included in the literature sets integrated for each of bio-items) stored in the literature full text searcher 212, for each of literature set types are as follows. The MEDLINE has 16,112,256 literatures, the PPI has 87,288 literatures, the mutant mouse catalog has 27,035 literatures, the OMIM has 23,023 literatures, the mouse gene catalog has 58,237 literatures, the human gene catalog has 22,707 literatures, the metabolite catalog has 9,350 literatures, the medical agent catalog has 1,015 literatures, and the disease name catalog has 1,884 literatures. The numbers of literatures of the literature set types stored in the literature full text searcher 204 are as follows. The MEDLINE has 6,940,248 literatures, the PPI has 22,476 literatures, the mutant mouse catalog has 12,280 literatures, the OMIM has 14,451 literatures, the mouse gene catalog has 58,237 literatures, the human gene catalog has 22,707 literatures, the metabolite catalog has 9,350 literatures, the medical agent catalog has 1,015 literatures, and the disease name catalog has 1,884 literatures.

More specifically, FIG. 21 is a diagram showing an example of a catalog searching result display screen in the single interval mode and showing an example in which a mutant mouse is searched for by using a literature set type mutant mouse catalog. In this example, 52 answers were obtained, and a time required for the searching was 0.109 seconds.

FIG. 22 is a diagram showing an example of a document searching result display screen in the multiple interval mode and showing an example in which a mouse gene is searched for by using a literature set type MEDLINE. In this example, 13 answers were obtained, and a time required for the searching was 2.045 seconds.

FIG. 23 is a diagram showing an example of a document indirect searching result display screen in the single interval mode and showing an example in which a mouse gene is searched for by using the literature set type MEDLINE. In this example, 5 answers were obtained, and a time required for the searching was 0.858 seconds.

FIG. 24 is a diagram showing an example of a document direct searching result display screen in the single interval mode and showing an example in which a mouse gene is searched for by using the literature set type MEDLINE. In this example, 9 answers were obtained, and a time required for the searching was 0.858 seconds.

Figure 25:
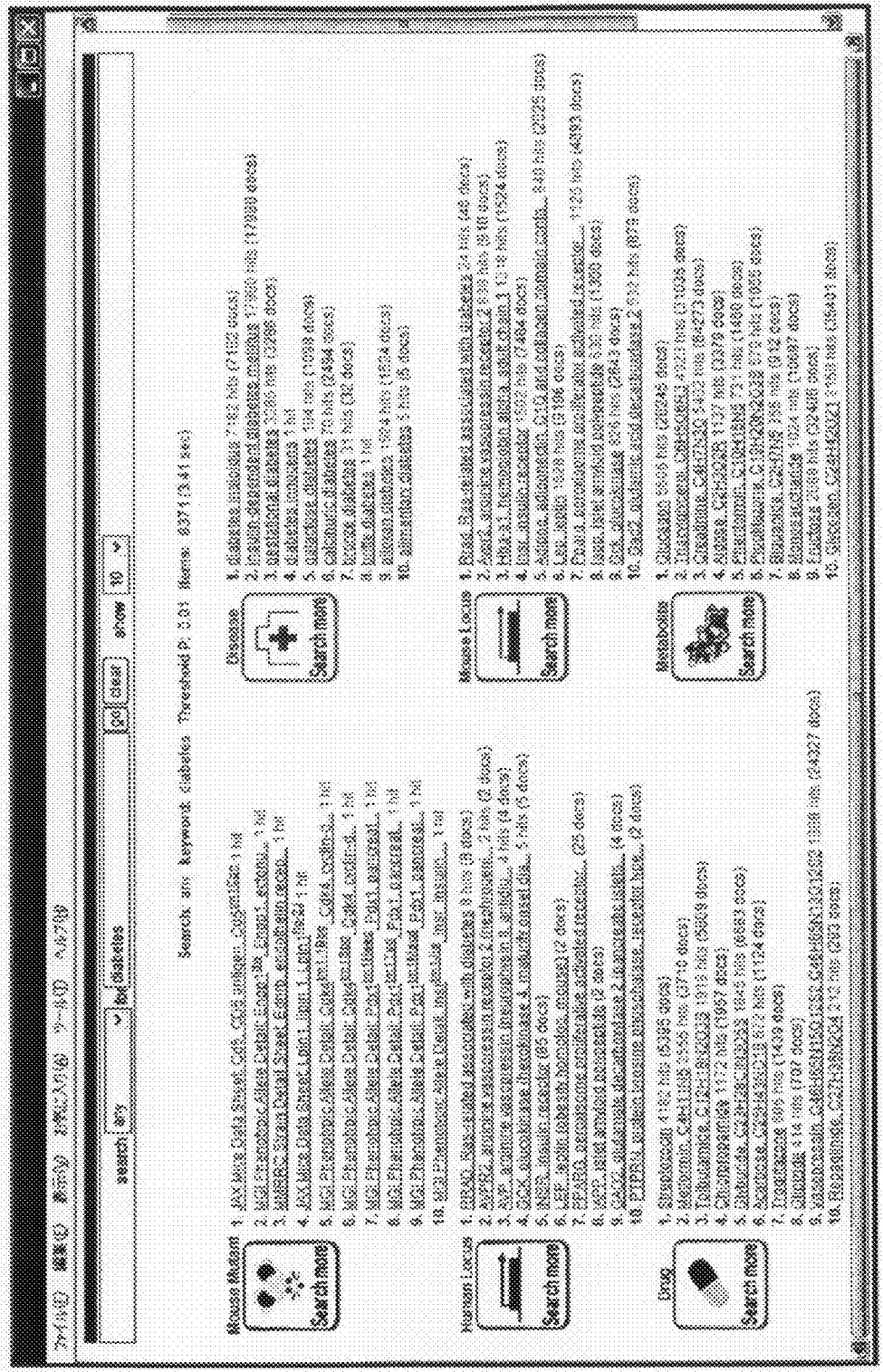
FIG. 25 is a diagram showing an example of a direct searching result display screen using a plurality of literature set types in the single interval mode (when an interval is not specified)

FIG. 25 is a diagram showing an example of a direct searching result display screen using a plurality of literature set types in the single interval mode (although an interval is not specified) and showing an example in which a mouse gene, a human gene, a metabolite, a medical agent, a mutant mouse, and a disease are searched for by using the literature set types, i.e., the MEDLINE, the PPI, the mutant mouse catalog, the OMIM, the mouse gene catalog, the human gene catalog, the metabolite catalog, the medical agent catalog, and the disease name catalog. In this example, 8371 answers were obtained, and a time required for the searching was 1.902 seconds.

Figure 26:
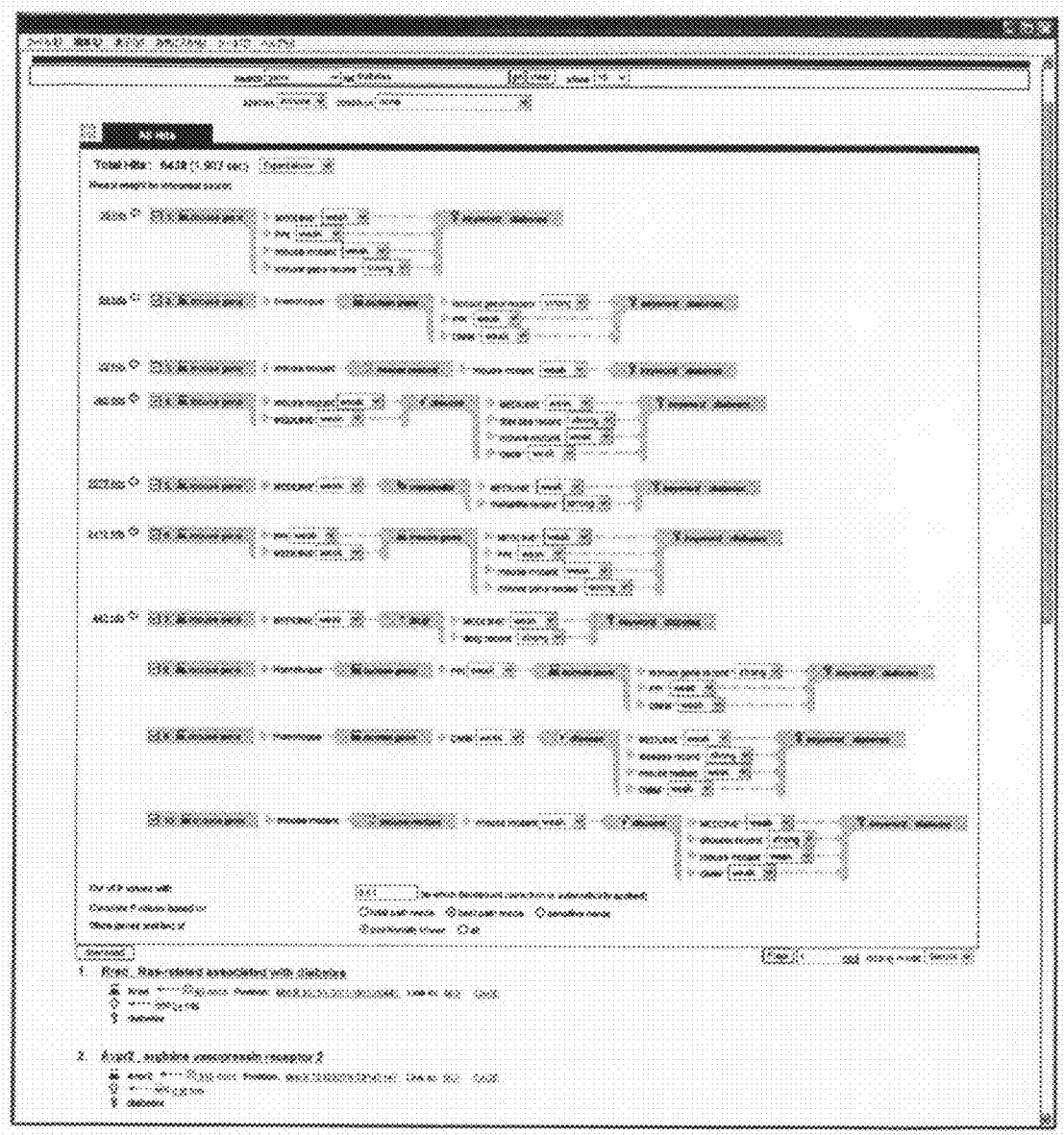
FIG. 26 is a diagram showing an example of a display screen of a direct searching result and an indirect searching result obtained by using a plurality of literature set types in the single interval mode.

FIG. 26 is a diagram showing an example of a display screen of a direct searching result and an indirect searching result obtained by using a plurality of literature set types in the single interval mode, and showing an example in which a mouse gene is searched for by using the literature set types, i.e., the MEDLINE, the PPI, the mutant mouse catalog, the OMIM, the mouse gene catalog, the human gene catalog, the metabolite catalog, the medical agent catalog, and the disease name catalog. In this example, 5438 answers were obtained, and a time required for the searching was 3.41 seconds.

Figure 27:
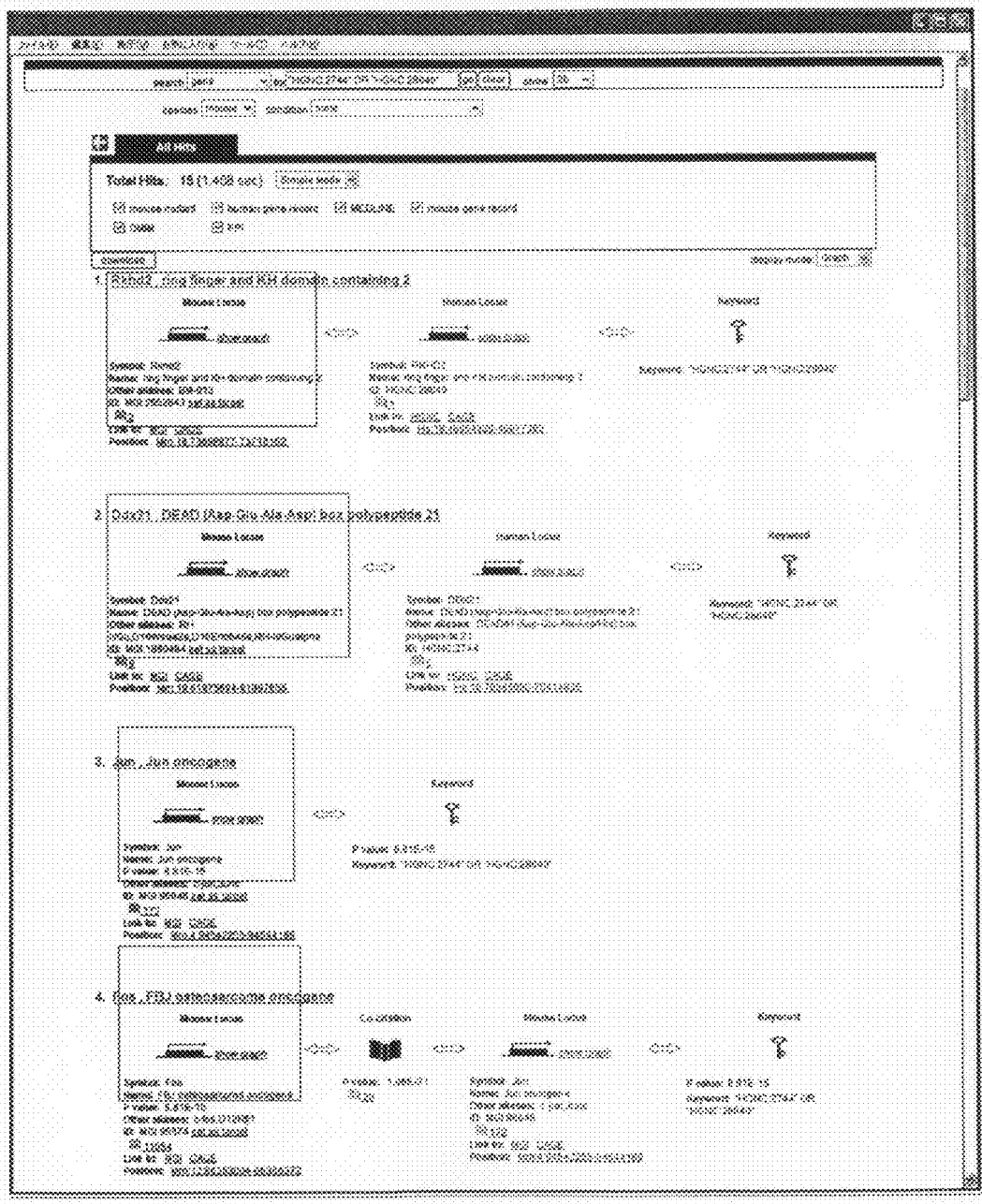
FIG. 27 is a diagram showing an example of a display screen of a direct searching result and an indirect searching result obtained by using a plurality of literature set types in the single interval mode.

FIG. 27 is a diagram showing an example of a display screen of a direct searching result and an indirect searching result obtained by using a plurality of literature set types in the single interval mode, in which a mouse gene is searched for by using the literature set types, i.e., the MEDLINE, the PPI, the mutant mouse catalog, the OMIM, the mouse gene catalog, the human gene catalog, the metabolite catalog, the medical agent catalog, and the disease name catalog, and in which a Boolean expression constituted by identifiers of human genes is used as a keyword. As shown in FIG. 27, as the identifiers of the human genes, "HGNC:2744" and "HGNC:28040" are input. In this example, 15 answers were obtained, and a time required for the searching was 1.468 seconds.

Figure 28:
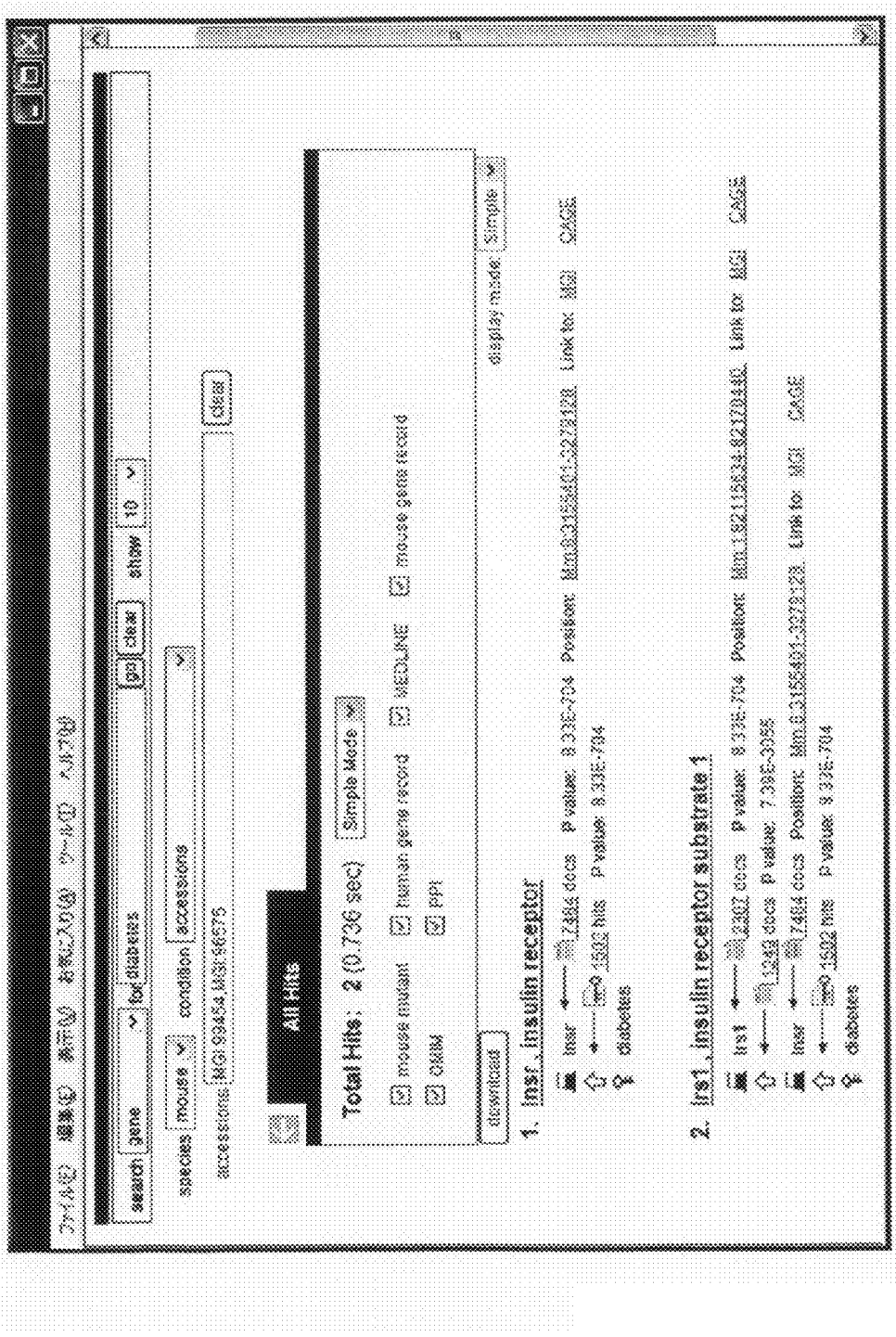
FIG. 28 is a diagram showing an example of a display screen of a direction searching result and an indirect searching result obtained by using a plurality of literature set types by specifying a sequence of identifiers in the single interval mode.

FIG. 28 is a diagram showing an example of a display screen of a direction searching result and an indirect searching result obtained by using a plurality of literature set types by specifying a sequence of identifiers in the single interval mode and showing an example in which a mouse gene is searched for by using the literature set types, i.e., the MEDLINE, the PPI, the mutant mouse catalog, the OMIM, the mouse gene catalog, the human gene catalog, the metabolite catalog, the medical agent catalog, and the disease name catalog. As shown in FIG. 28, as a sequence of identifiers, "HGI:99454,MGI:96575" is input by a user. In this example, 2 answers were obtained, and a time required for the searching was 0.736 seconds.

Figure 29:
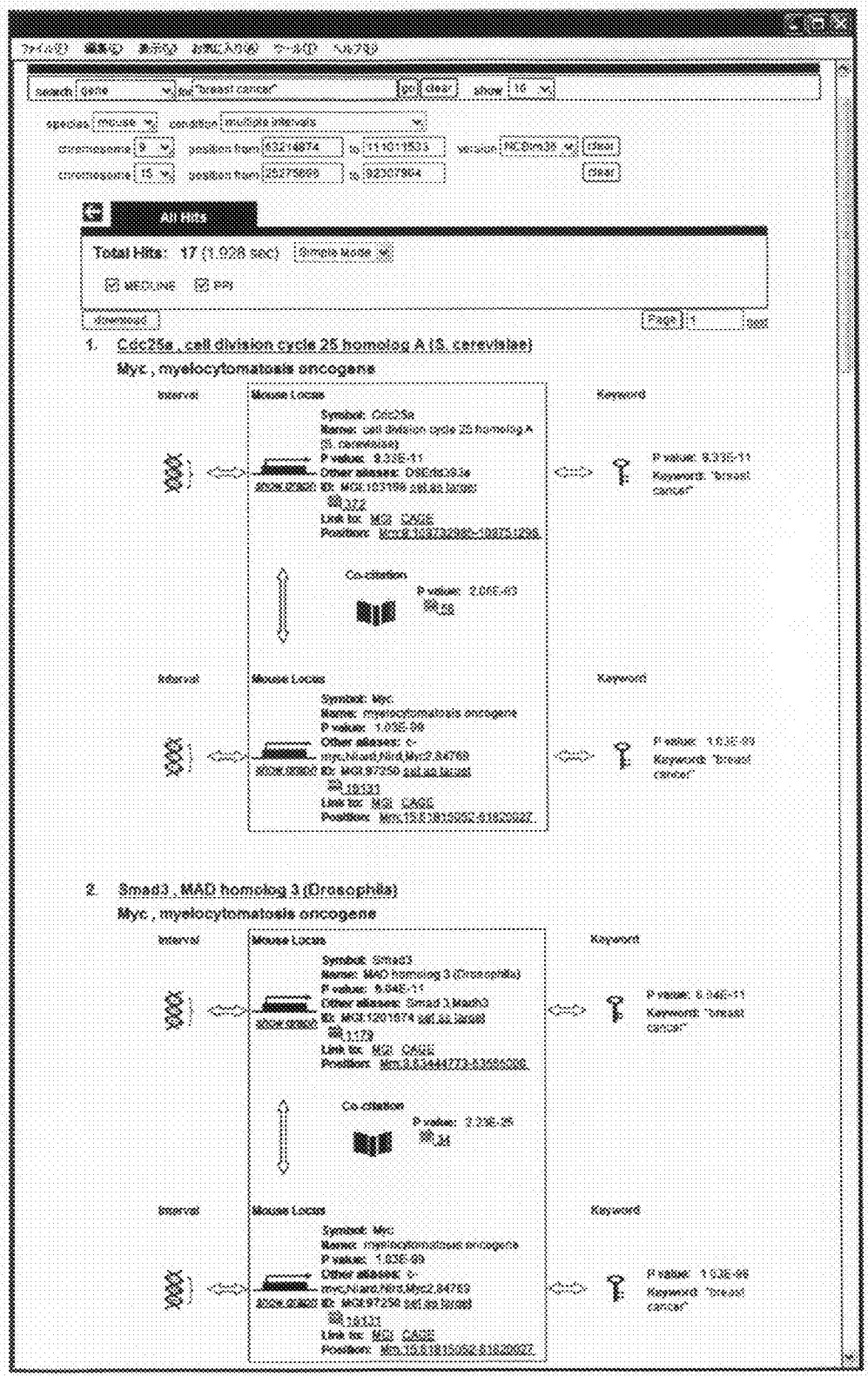
FIG. 29 is a diagram showing an example of a searching result display screen using a plurality of literature set types in the multiple interval mode.

FIG. 29 is a diagram showing an example of a searching result display screen using a plurality of literature set types in the multiple interval mode and showing an example in which a mouse gene is searched for by using the literature set types, i.e., the MEDLINE, the PPI, the mutant mouse catalog, the OMIM, the mouse gene catalog, the human gene catalog, and the disease name catalog. In this example, 17 answers were obtained, and a time required for the searching was 1.928 seconds.

Number-of-Literature Acquiring Server

Figure 18:
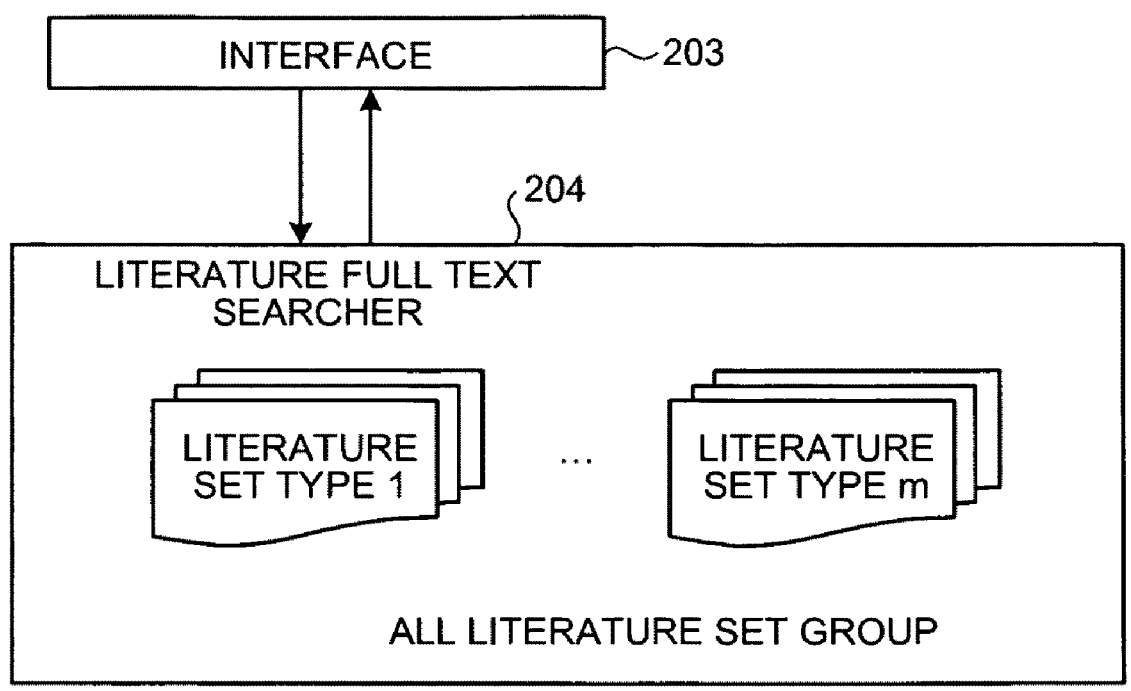
FIG. 18 is a diagram showing an example of an architecture of a number-of-literatures acquiring server.

An architecture of the number-of-literatures acquiring server 202 will be explained by using FIG. 18. FIG. 18 is a diagram showing an example of the architecture of the number-of-literatures acquiring server.

As shown in FIG. 18, the number-of-literatures acquiring server 202 includes an interface 203 and a literature full text searcher 204. The literature full text searcher 204 includes an all-literature set file in which a literature set (all-literature set: a group of all literatures associated with at least one bio-item) group obtained by collecting all literatures related to the bio-item literatures sets for each of literature set types 1 to m is stored. Full-text searching is performed to the all-literature set by a keyword to acquire the number (Nk) of literatures which is related to the keyword and the Nk which is not related to the keyword for each of the literature set types 1 to m. In this case, as a format of the all-literature set file, an index format of Apache Lucene™ is suitably used. However, the present invention does not limit the file format.

Distributed Literature Searching Server

An architecture of the distributed literature searching server 210 will be explained with reference to FIG. 19. FIG. 19 is a diagram showing an example of the architecture of the distributed literature searching server 210.

The distributed literature searching server 210 includes five components, i.e., the interface 211, the literature full text searcher 212, the bio-item region determining unit 212i, the correlation score calculator 212d, the bio-item inferring unit 212e, and a bio-item name table 212f.

The distributed literature searching server 210 includes a bio-item literature set file in which bio-item literature set groups obtained by equally dividing the bio-item literature set by the number of literature searching servers 210a to x are stored. More specifically, the related literature set (bio-item literature set) groups are arranged in the literature full text searcher 212 for the bio-items 1 to r of an allocated bio-item literature set, respectively. At this time, the related literature groups are integrated for each of literature set types as shown in FIG. 19. In this case, as a format of the bio-item literature set file, an index format of Apache Lucene™ is suitably used. However, the present invention does not limit the file format.

The bio-item inferring unit 212e includes a database (bio-item relation database) table in which relationship data between two bio-items is stored. As the relationships between the two bio-items, the following relationships of two types A) and B) are known.

A) Relationship Extracted from Co-Occurrence Relationship on Literature

Co-presence of two bio-item names in one literature is called that the two-bio items co-occur in the literature. With respect to the two bio-items extracted in the co-occurrence relationship, a two-dimensional number-of-literatures table and a correlation score (co-occurrence relationship correlation score) are calculated for each of the literature set types 1 to m in advance to create a database. In this case, when the two bio-items are defined as bio-item 1 and bio-item 2, respectively, the two-dimensional number-of-literatures table is constituted by values a, b, c, and d including a: the number of literatures each including both a name of the bio-item 1 and a name of the bio-item 2, b: the number of literatures each including the name of the bio-item 1 and not including the name of the bio-item 2, c: the number of literatures each not including the name of the bio-item 1 and including the name of the bio-item 2, and d: the number of literatures each not including the name of the bio-item 1 and not including the name of the bio-item 2. The co-occurrence relationship correlation score is a P value calculated by performing a Fisher's exact test to the two-dimensional number-of-literatures table.

B) Relationship Extracted by Experiment or the Like Other than Literature Co-Occurrence The P value is given to the relationship between the two bio-items as a correlation score (co-occurrence relationship correlation score) to create a database. At this time, the two-dimensional number-of-literatures table is not defined.

In an operation in the single interval mode, the operation of each of the distributed literature searching servers 210 is as follows.

Operation in Single Interval Mode (1) The interface 211 receives a request (keyword, interval, or the like) and a combination $\langle n_k^{d_i}, \neg n_k^{d_i} \rangle$ between the number of literatures $n_k^{d_i}$ ($1 \leq i \leq m$) which are related to a keyword of various literature sets $d_i$ ($1 \leq i \leq m$) and the number of literatures $\neg n_k^{d_i}$ ($1 \leq i \leq m$) which are not related to the keyword obtained from the number-of-literatures acquiring server 202 from the back-end management server 201, and transmits the request and the combination to the literature full text searcher 212.

(2) The literature full text searcher 212 performs the following operations (3), (4), and (5) with respect to, for example, the bio-item 1 (expressed by $g_1$).

(3) The literature full text searcher 212 performs full-text searching by a keyword to a bio-item-1-related literature (bio-item literature set of the bio-item 1) group (the number of literatures: $n_{g_1}^{d_1}$) of literature set type 1 (expressed by $d_1$) to acquire the number of retrieved literatures $n_h^{d_1}$. When the number of literatures $n_h^{d_i}$ is 1 or larger, the literature full text searcher 212 transmits a 4-piece combination $\langle n_h^{d_1}, n_{g_1}^{d_1}, n_k^{d_1}, \neg n_k^{d_1} \rangle$ to the correlation score calculator 212d and executes (8) to calculate a two-dimensional number-of-literatures table $T_{k-g_1}^{d_1}$ and a correlation score $P_{k-g_1}^{d_1}$ and to generate a 3-piece combination $\langle d_1, T_{k-g_1}^{s_1}, P_{k-g}^{d_1} \rangle$.

(4) The literature full text searcher 212 executes (3) to other literature set types, i.e., literature set type 2 to literature set type m.

(5) The literature full text searcher 212 calculates a minimum value of correlation scores $P_{k-d_1}^{d_1} \ldots P_{k-g_1}^{d_m}$ of the various literature sets 1 to m obtained in (3) and (4) and uses the minimum value as a correlation score $P_{k-g_1}$. When the correlation score $P_{k-g_1}$ is lower than a predetermined level, the bio-item region determining unit 212i checks whether the bio-item 1 is included in the interval, and executes (i) and (ii).

(i. Direct Searching) When the bio-item 1 is included in the interval, the bio-item 1 is employed as a searching result, and a combination constituted by a list of the 3-piece combination $\langle d_i, T_{k-g_1}^{d_i}, P_{k-g_1}^{d_i} \rangle$ ($1 \leq i \leq m$) obtained by the (3) and (4), the bio-item 1, and the correlation score $P_{k-g_1}$ is stored in a storage device (memory) as one of answers.

(ii. Inference Searching) When the bio-item 1 is not included in the interval, bio-item groups $x_1 \ldots, x_q$ (these are expressed as $g_{x1} \ldots, g_{xq}$) related to the bio-item 1 are obtained by using the bio-item inferring unit 212e. With respect to each bio-item $x_i$ ($1 \leq i \leq q$), a bio-item included in the interval is selected by using the bio-item region determining unit 212i. (6) and (7) are executed to each of the selected bio-items $x_i$.

In this case, in determination whether a bio-item is present in an interval, when the bio-item belongs to a bio-item set such as a medical agent which does not have a position, the processing is performed on the assumption that the bio-item is always present in the interval. Even when a biological species of the bio-item is different from a biological species of a genome sequence in a region (interval) specified by a user, when a homological relationship is present, the homological relationship is applied. Furthermore, even when the bio-item 1 is included in the interval, (ii) can be executed at the instruction of the user.

At an instruction of a user, the correlation score $P_{k-g_1}$ between the keyword and the bio-item 1 may be integrated with any one or all of number-of-literatures tables $T_{k-g_1}^{d_1} \ldots T_{k-g_1}^{d_m}$ of the literature set types 1 to m to generate new number-of-literatures tables. By using the number-of-literatures tables, a correlation score between the bio-item and the keyword may be calculated based on statistical calculation. More specifically, by the (3) and (4), the number-of-literatures tables $T_{k-g_1}^{d_1} \ldots T_{k-g_1}^{d_m}$ shown in FIG. 2 are created for each of literature set types 1 to m. However, a new number-of-literatures table (in FIG. 2, a table obtained by assigning A, B, C, and D to a, b, c, and d, respectively) constituted by A obtained by summing up all terms a of each of the number-of-literatures tables $T_{k-g_1}^{d_1} \ldots T_{k-g_1}^{d_m}$ of each of the literature set types 1 to m, B obtained by summing up all terms b, C obtained by summing up all terms c, and D obtained by summing up all terms d may be generated. The number-of-literatures table constituted as described above will be called an integrated number-of-literatures table hereinafter.

Alternatively, at least one literature set type for which the integrated number-of-literatures table is created is arbitrarily selected from the literature set types 1 to m to generate an integrated number-of-literatures table. By using the integrated number-of-literatures table, a correlation score between the bio-item and the keyword is calculated. Furthermore, with respect to each of the literature set types for which the integrated number-of-literatures tables are not created, a correlation score between the bio-item and the keyword may be calculated from the number-of-literatures table, and a minimum correlation score selected from the correlation scores may be used as the correlation score $P_{k-g_1}$ of the of the bio-item.

(6) With respect to one bio-item $x_1$ (this is expressed by $g_{x1}$) of the bio-items related to the bio-item 1, by using the bio-item inferring unit 212e, according the following method, a correlation score between the bio-item 1 and the bio-item $x_1$ and a two-dimensional number-of-literatures table is acquired. When a relation between the bio-item 1 and the bio-item $x_1$ is obtained by co-occurrence on a literature, two-dimensional number-of-literatures tables $T_{g_1-g_{x1}}^{d_i}$ and correlation scores $P_{g_1-g_{x1}}^{d_i}$ of all the literature sets $d_i$ ($1 \leq i \leq m$) are acquired to generate a 3-piece combination $\langle d_i, T_{g_1-g_{x1}}^{d_i}, P_{g_1-g_{x1}}^{d_i} \rangle$, otherwise, a correlation score $P_{g_1-g_{x1}}^{e_j}$ ($1 \leq j \leq s$, s is the number of bio-item relationships $e_j$ found by an experiment or the like but co-occurrence on a literature) is acquired to generate a 3-piece combination $\langle e_j, \phi, P_{g_1-g_{x1}}^{e_j} \rangle$, where $\phi$ is an empty number-of-literatures table. A minimum value of all the obtained correlation scores $P_{g_1-g_{x1}}^{d_i}$ and the obtained $P_{g_1-g_{x1}}^{e_j}$ ($1 \leq j \leq s$) is calculated. The minimum value is used as the correlation score $P_{g_1-g_{x1}}$ between the bio-item 1 and the bio-item $x_1$.

Figure 31:
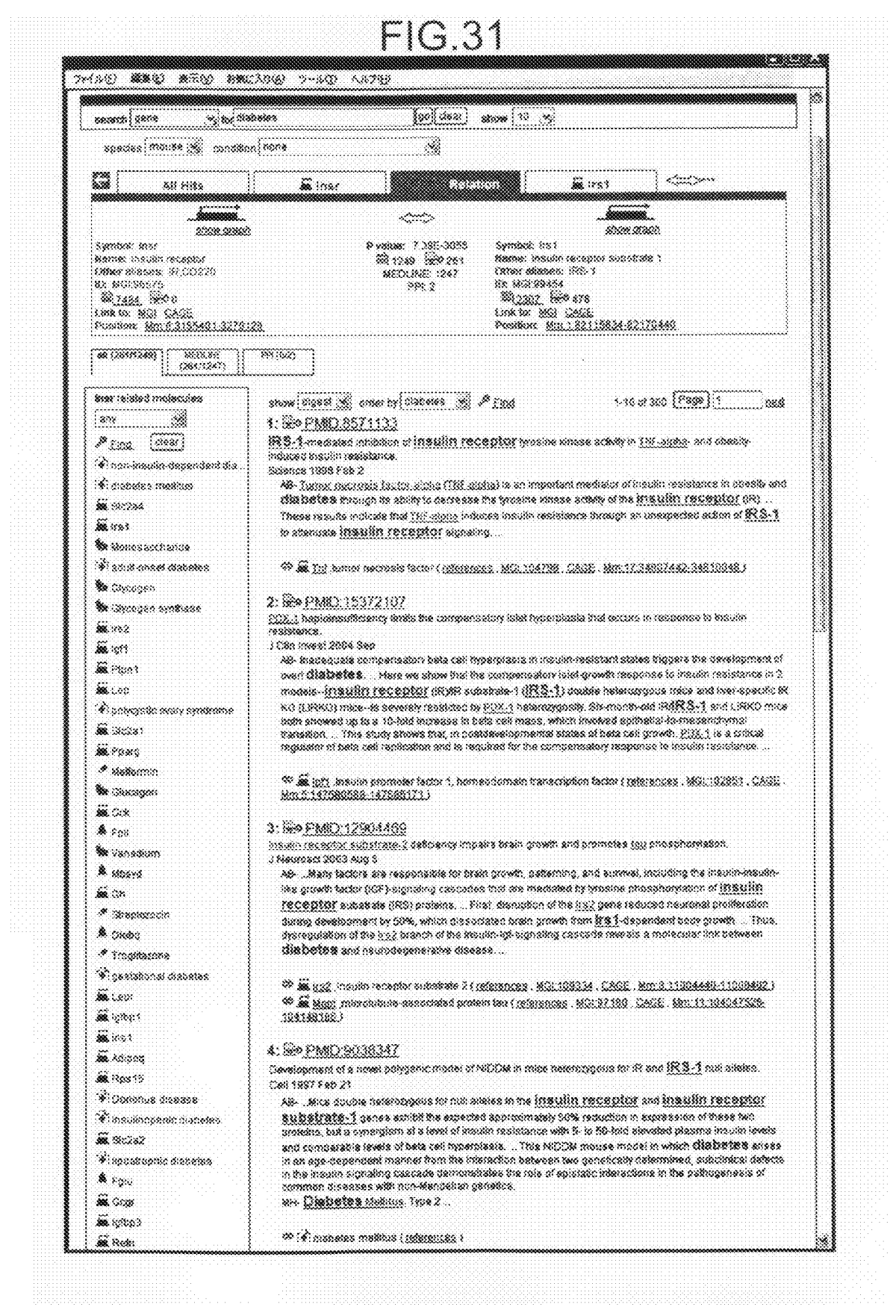

At an instruction of a user, in calculation of the correlation score $P_{g_1-g_{x1}}$, the $P_{g_1-g_{x1}}$ between the bio-item 1 and the bio-item $x_1$ may be integrated with any one or all of number-of-literatures tables $T_{g_1-g_{x1}}^{d_1} \ldots T_{g_1-g_{x1}}^{d_m}$ of the literature set types 1 to m to generate new number-of-literatures tables. By using the number-of-literatures tables, a correlation score between the bio-item and the keyword may be calculated based on statistical calculation. More specifically, the number-of-literatures tables $T_{k-g_1}^{d_1} \ldots T_{k-g_1}^{d_m}$ shown in FIG. 31 are created for each of literature set types 1 to m. However, a new integrated number-of-literatures table (in FIG. 31, a table obtained by assigning A, B, C, and D to a, b, c, and d, respectively) constituted by A obtained by summing up all terms a of each of the number-of-literatures tables $T_{k-g_1}^{d_1} \ldots T_{k-g_1}^{d_m}$ of each of the literature set types 1 to m, B obtained by summing up all terms b, C obtained by summing up all terms c, and D obtained by summing up all terms d may be generated. A minimum value of the correlation score calculated from the integrated number-of-literatures table and the correlation score $P_{g_1 g_2}^{e_j}$ ($1 \leq j \leq s$) of the bio-item found by an experiment or the like but co-occurrence on a literature is calculated. The minimum value is used as $P_{g_1-g_{x1}}$ between the bio-item 1 and the bio-item $x_1$.

Alternatively, at least arbitrary one literature set type for which the integrated number-of-literatures table is created may be arbitrarily selected from the literature set types 1 to m to generate an integrated number-of-literatures table. By using the integrated number-of-literatures table, a correlation score between the bio-item and the keyword is calculated, and the correlation score between the bio-item and the keyword is calculated from the number-of-literatures table for each of the literature set types for which the integrated number-of-literatures table is not created. A minimum value of the correlation scores and the correlation score $P_{g1-gx1}^{ej}$ ($1 \leq j \leq s$) of the bio-item found by an experiment or the like but co-occurrence on a literature is calculated. The value may be used as the $P_{g1-gx1}$ between the bio-item 1 and the bio-item $x_1$.

Figures 32, 33:
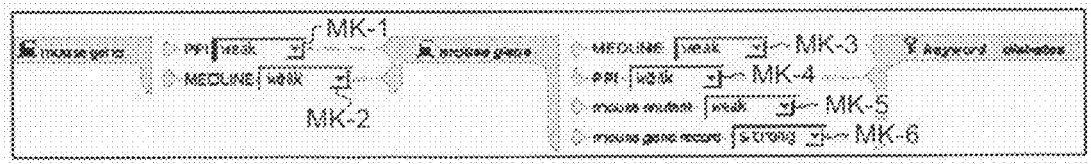
FIG. 32 is a diagram showing an example of a number-of-literatures table between bio-item 1 and bio-item 2.
FIG. 33 is a diagram showing an example in which a user specifies a method of creating an integrated number-of-literatures table in the (5) and (6) on a Web browser serving as a user client 500.

In this case, FIG. 32 is a diagram showing an example of a number-of-literatures table between the bio-item 1 and the bio-item 2. As shown in FIG. 32, the number-of-literatures table is constituted by at least one of four items a) to d): a) the number of literatures each including the bio-item 1 and the bio-item 2 name, b) the number of literatures each not including the bio-item 1 and including the bio-item 2 name, c) the number of literatures each including the bio-item 1 and not including the bio-item 2 name, and d) the number of literatures each not including the bio-item 1 and not including the bio-item 2 name. FIG. 33 is a diagram showing an example in which a user specifies a method of creating an integrated number-of-literatures table in the (5) and (6) on the Web browser serving as the user client 500.

As shown in a right portion of FIG. 33, selected tabs (MEDLINE selecting tab MK-3, PPI selecting tab MK-4, mouse mutant selecting tab MK-5, and mouse gene record selecting tab MK-6) of the literature set types used in association between a keyword and mouse genes in (5) are displayed. More specifically, for each of the literature set types, the integrated number-of-literatures table creating method in (5) can be selected from methods of three types, i.e., weak, strong, and none (not shown). In this case, for literature set types in which weak is set, an integrated number-of-literatures table is created from the two-dimensional number-of-literatures table of the literature set types. For the literature set type in which strong is set, when the number ($n_h$) of literatures retrieved with a keyword obtained in (3) of the literature set type is 1 or larger, a correlation score between the keyword of the literature set type and the bio-item is set to 0. In this manner, for the literature set type in which strong is set, the same advantage as that of an operation of a literature server for a catalog set can be achieved, and a function of simultaneously searching for a document set and a catalog set is realized. A literature set type in which none is set is excluded from the literature set types to be searched.

Figure 30:
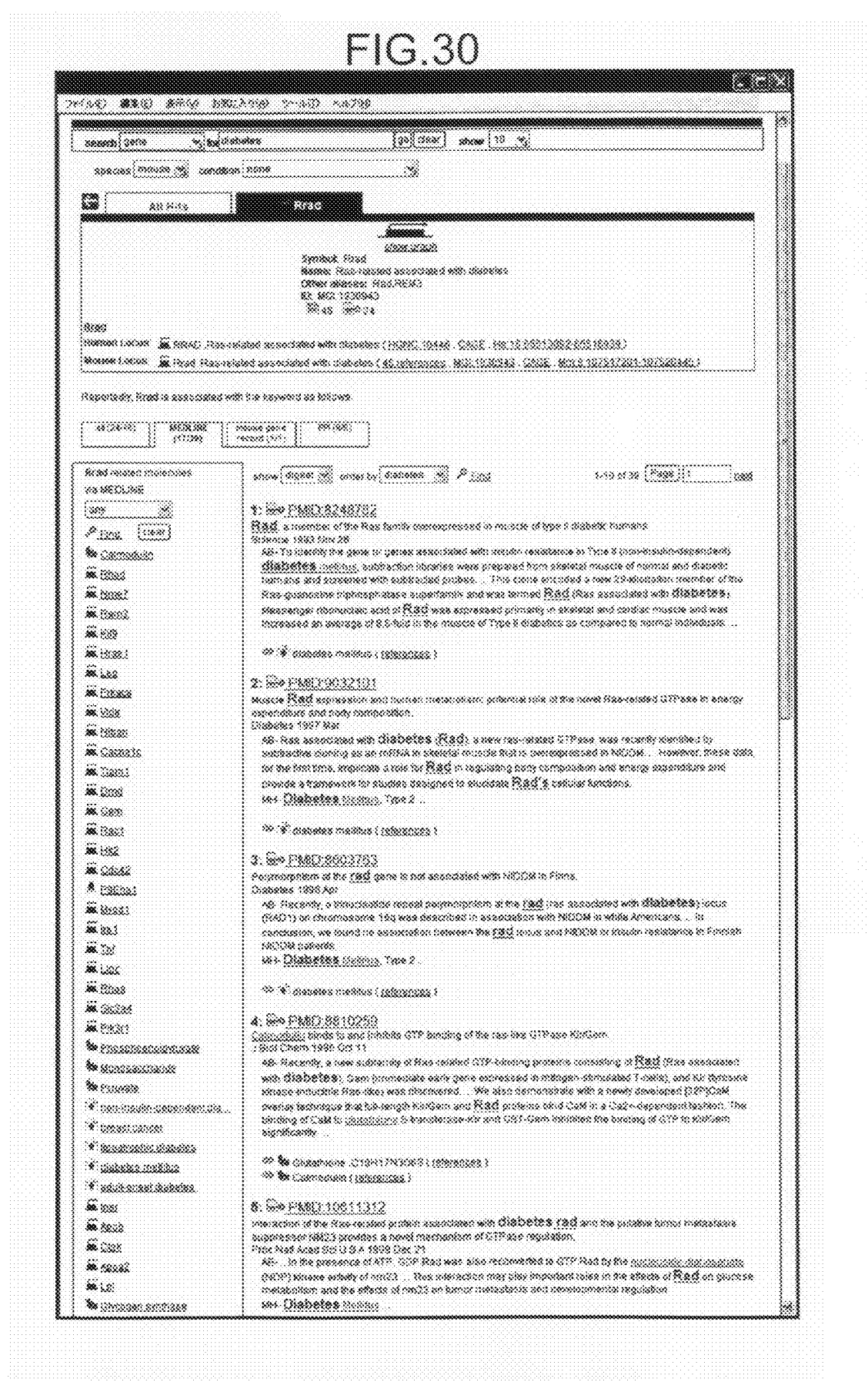

As shown in a left portion of FIG. 33, an inter-mouse-genes relationship used in (6) is specified. More specifically, as shown in the left portion of FIG. 33, with respect to the inter-mouse-genes relationship extracted based on a co-occurrence relationship on a literature, selecting tabs (PPI selecting tab MK-1 and MEDLINE selecting tab MK-2) of the literature set type are displayed. More specifically, for each of the literature set types, the integrated number-of-literatures table creating method in (6) can be selected from methods of three types, i.e., weak, strong, and none (not shown). In this case, for a literature set type in which weak is set, an integrated number-of-literatures table is created from the two-dimensional number-of-literatures table of the literature set type. For the literature set type in which strong is set, when at least one co-occurrence literature is present, a correlation score between the two bio-items of the literature set type is set to 0. A literature set type in which none is set is excluded from the literature set types to be searched. In this manner, when a user performs various selections of the literature set types, a searching display result as shown in FIG. 30 or 31 can be obtained. FIG. 30 is a diagram showing an example which displays details of related literatures between a keyword "diabetes" and a mouse gene "Rrad" retrieved under the conditions in FIG. 33 are displayed. FIG. 31 is a diagram showing an example which displays details of related literature between a mouse gene "Insr" and a mouse gene "Irs1".

(7) The correlation scores $P_{g1}$ and $P_{g1-gx1}$ are transmitted to the correlation score calculator 212d, and (9) is executed to obtain a total correlation score $P_{total}$. When the total correlation score $P_{total}$ obtained here is lower than a predetermined level, a 6-piece combination constituted by the bio-item $x_1$, the bio-item 1, the correlation score $P_{total}$, $P_{k-g1}$, $P_{g1-gx1}$, and all the 3-piece lists obtained in (6) is held on the storage device (memory) as one of answers.

(8) The correlation score calculator 212d receives a 4-piece combination $<n_h, n_{g1}, n_k, n_k>$ from the literature full text searcher 212. The correlation score calculator 212d creates a two-dimensional number-of-literatures table shown in the following table 1, and calculates a P value from the table 1 by applying a Fisher's exact test. A combination of the calculated P value and the two-dimensional number-of-literatures table is returned to the literature full text searcher 212.

TABLE 1

TWO-DIMENSIONAL NUMBER-OF-LITERATURES TABLE FOR CORRELATION SCORE CALCULATION

| | KEYWORD IS INCLUDED | KEYWORD IS NOT INCLUDED |
|---|---|---|
| BIO-ITEM 1 IS DESCRIBED | $n_h$ | $n_{g1}-n_h$ |
| BIO-ITEM 1 IS NOT DESCRIBED | $n_k-n_h$ | $\neg n_k-(n_{g1}-n_h)$ |

(9) The correlation score calculator 212d receives correlation scores $P_{k-g1}$ and $P_{g1-gx1}$ from the literature full text searcher 212, and the correlation score calculator 212d calculates the total correlation score $P_{total}=1-(1-P_{k-g1})(1-P_{g1-gx1})$ and returns to the value to the literature full text searcher 212.

(6), (7), and (8) are executed to other bio-items related to the bio-item 1.

(10) The distributed literature searching server 210 executes (2) to the other bio-items, i.e., the bio-item 2 to the bio-item r.

(11) The distributed literature searching server 210 returns all the answers held on the storage device (memory) to the back-end management server 201 through the interface 211.

In this case, in the operation in the multiple interval mode, an operation of each of the distributed literature searching servers 210 is as follows.

Operation in Multiple Interval Mode

The distributed literature searching server 210 sequentially executes the operations (1), (2), (3), (4), and (5)(i) in the single interval mode to search for a bio-item present in the interval 1 and returns an obtained answer to the back-end management server 201 through the interface 211. The back-end management server 201 integrates the answers returned from all the distributed literature searching servers 210a to x to generate an answer list L.

The back-end management server 201 transmits a request including the answer list L to the distributed literature searching servers 210a to x to search for a bio-item present in the interval 2 and to obtain a result. The literature full text searcher 212 performs the following operation.

(12) The interface 211 receives the request, i.e., a keyword, an interval, and a sequence of identifiers from the back-end management server 201 and a combination between the number of literatures $n_k^{d_i}$ ($1 \leq i \leq m$) which is related to a keyword and the number of literatures $\neg n_k^{d_i}$ ($1 \leq i \leq m$) which is not related to the keyword of each literature set type $d_i$ ($1 \leq i \leq m$)

obtained from the number-of-literatures acquiring server 202 and transmits the request to the literature full text searcher 212.

(13) The literature full text searcher 212 executes (3), (4), and (5)(i) to the bio-item 1 and the interval 2. When the bio-item 1 is an answer, (14) is executed.

(14) The literature full text searcher 212 creates all bio-item pairs each of which can be constituted by each answer bio-item of the answer list L and the bio-item 1. The following (a) and (b) are executed to the bio-item pairs.

(a) With respect to one of the bio-item pairs, bio-items constituting the bio-item pair are represented by $g_x$ and $g_1$, respectively. The bio-item pair is transmitted to the bio-item inferring unit 212e to check whether $g_x$ and $g_1$ are related to each other.

(b) As a result of (a), when $g_x$ and $g_1$ are related to each other, (15) is executed.

(c) (a) is also executed to other bio-item pairs.

(15) The literature full text searcher 212 executes (6) to the bio-item 1 (expressed by $g_1$) and the bio-item x (expressed by $g_x$) to obtain a correlation score $P_{g1\text{-}gx}$ therebetween. It is assumed that a correlation score between the keyword and the bio-item 1 is represented by $P_{k\text{-}g1}$ and a correlation score between the keyword and the bio-item x is represented by $P_{k\text{-}gx}$. A 3-piece combination $<g_1, g_x, P_{g1\text{-}gx}>$ is transmitted to the correlation score calculator 212d, and (16) is executed to obtain a total correlation score $P_{total}$. When the total correlation score $P_{total}$ is lower than a predetermined level, a 7-piece combination constituted by the bio-item 1, the bio-item x, the correlation score $P_{total}, P_{k\text{-}g1}, P_{k\text{-}gx}, P_{g1\text{-}gx1}$ and all the 3-piece lists obtained in (6) is held on the storage device (memory) as one of answers.

(16) The correlation score calculator 212d receives the 3-piece combination $<g_1, g_x, P_{g1\text{-}gx}>$ from the literature full text searcher 212. The correlation score calculator 212d calculates a total correlation score $P_{total}=\text{Min}\{1-(1-P_{k\text{-}g1})(1-P_{g1\text{-}gx}), 1-(1-P_{k\text{-}gx})(1-P_{g1\text{-}gx})\}$ and returns the total correlation score to the literature full text searcher 212. In the equation, Min{a,b} is a function of returning not larger one of a and b.

(17) The distributed literature searching server 210 executes (13) to the other bio-items, i.e., the bio-item 2 to the bio-item r.

(18) The distributed literature searching server 210 returns all the answers held on the storage device (memory) to the back-end management server 201 through the interface 211.

More Detailed Analysis of the Number of Retrieved Literatures

More detailed analysis of the number of retrieved literatures will be explained with reference to FIG. 8. With respect to an answer of inference searching in the single interval mode and an answer in the multiple interval mode, and the two bio-items which constitute an answer, i.e, the bio-item 1 and the bio-item 2, the relationships between the bio-item 1 and the keyword, between the bio-item 2 and the keyword, and between the bio-item 1 and the bio-item 2 are given, and for each of the three relationships, a 3-piece list constituted by a literature set, a correlation score, and a two-dimensional number-of-literatures table obtained in (3), (4), and (6) is present. When the two-dimensional number-of-literatures tables for all the three parts are present for a literature set $d_i$ ($1 \leq i \leq m$), a three-dimensional number-of-literatures table shown in FIG. 8 can be constructed.

The distributed literature searching server 210 has a function of realizing the three-dimensional number-of-literatures table. A detailed operation will be described below. Variables a, b, c, d, e, f, g, h, i, j, k, m, s, t, u, v, w, x, y, and z to be used in the following explanation correspond to variables in FIG. 8, respectively.

(1) The interface 211 receives one of answers and the keyword from the back-end management server 201 and transmits the answer and the keyword to the literature full text searcher 212.

(2) The literature full text searcher 212 acquires a name of the bio-item 2 from the bio-item name table 212f.

(3) The literature full text searcher 212 acquires a 3-piece list constituted by the literature set, the correlation score, and the two-dimensional number-of-literatures table with respect to three relationships, i.e., the relationships between the bio-item 1 and the keyword, the bio-item 2 and the keyword, and between the bio-item 1 and the bio-item 2 which constitute an answer. At this time, all literature sets in each of which the two-dimensional number-of-literatures tables are present in all the three-piece combinations of the three parts are acquired. (4) is executed to each of the acquired literature sets $d_i$.

(4) The literature full text searcher 212 searches a bio-item-1-related literature set (bio-item literature set of the bio-item 1) group of the literature set $d_i$ for a literature including the keyword and the name of the bio-item 2 to obtain the number of literatures and to set the number of literatures as s. Furthermore, it is assumed that two-dimensional number-of-literatures table of the keyword and the bio-item 1 of the literature sets $d_i$ are represented by a), b), c), and d), two-dimensional number-of-literatures table of the keyword and the bio-item 2 are represented by e), f), g), and h), and two-dimensional number-of-literatures table of the bio-item 1 and the bio-item 2 are represented by i), j), k), and m). At this time, w=a−s, u=e−s, t=i−s, v=f−t, x=k−w, y=c−u, and z=d−v are calculated to generate the three-dimensional number-of-literatures table shown in FIG. 8.

(5) The literature full text searcher 212 generates a combination between an answer received in (1) and the three-dimensional number-of-literatures table group received in (4) and returns the combination to the back-end management server 201 through the interface 211. This is the more detailed analysis of the number of retrieved literatures.

Effect of Introduction of Concept Word

When a P value is calculated by a bio-item query constituted by only a bio-item name, ranking of a retrieved bio-item is not correct. However, the P value may be calculated by a bio-item query to which a concept word is introduced. In this case, the accuracy of a ranking result is considerably improved.

ANOTHER EMBODIMENT

The embodiment of the present invention has been described above. However, the present invention may be executed in not only the embodiment described above but also various different embodiments within the technical idea described in the scope of the invention.

The present invention used in searching for a literature folder will be described below. For example, as a path name of the literature folder, there is /home/document/diabetes/. When three literatures are present in the literature folder with the following file path names, all the file path names of these literatures include the path name of the literature folder. For this reason, when the method of the present invention is applied such that the path name of the literature folder is used as a bio-item name, a literature set including these literatures can be created as a bio-item literature set of the literature folder.

/home/document/diabetes/patient1
/home/document/diabetes/patient2
/home/document/diabetes/patient3

Figure 34:
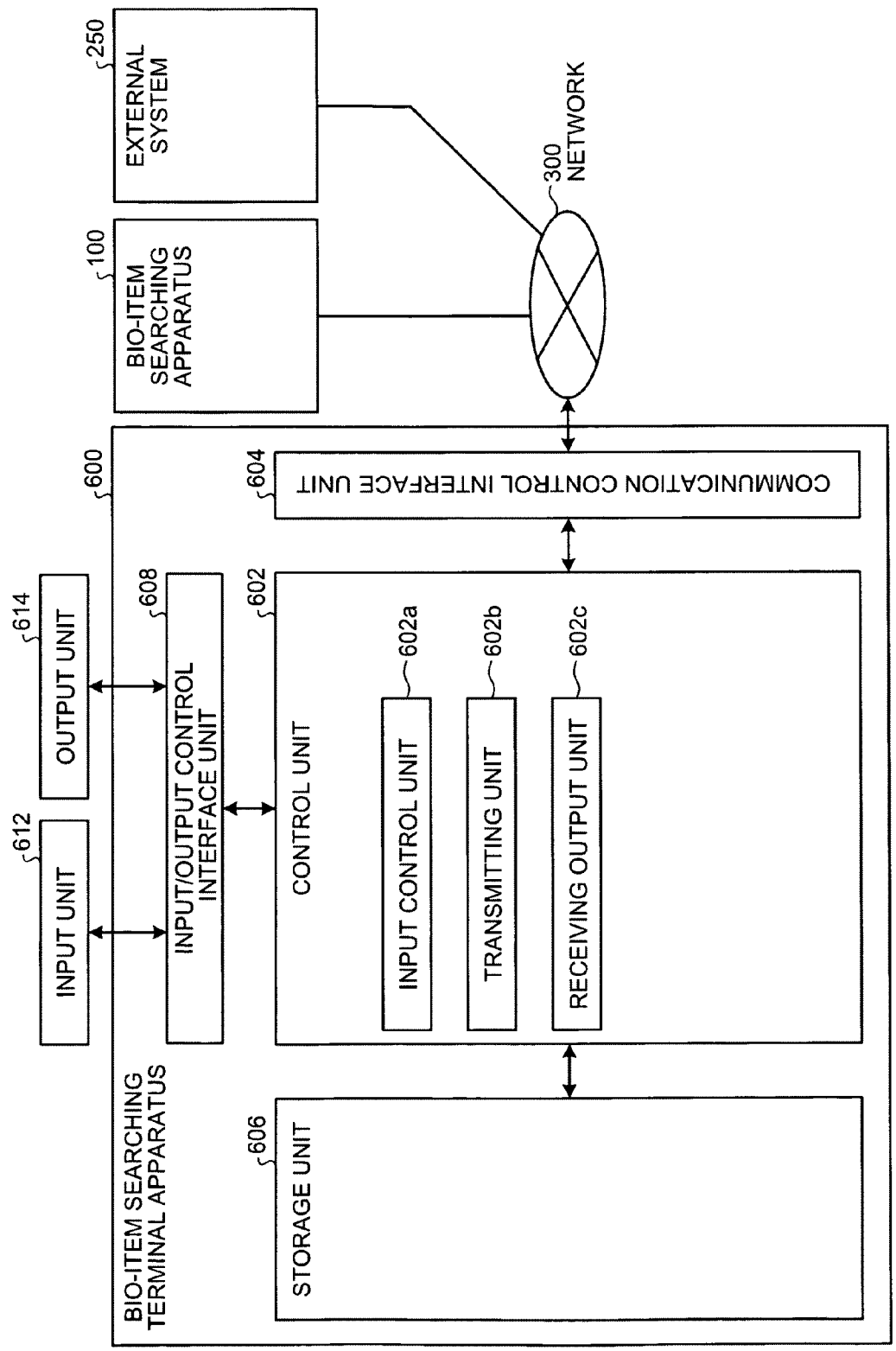
FIG. 34 is a block diagram showing an example of a configuration of a bio-item searching terminal apparatus 600.

In the above embodiment, an example in which the bio-item searching apparatus 100 mainly performs the processes in a standalone mode is explained. However, as described in the embodiment, a process may be performed in response to a request from another terminal apparatus constituted by a housing different from that of the bio-item searching apparatus 100, and the process result may be returned to the client terminal. FIG. 34 is a block diagram showing an example of a configuration of a bio-item searching terminal apparatus 600.

More specifically, as shown in FIG. 34, the bio-item searching terminal apparatus 600 is mutually connected to the bio-item searching apparatus 100 through a network 300 and includes at least a control unit 602, an input unit 612, and an output unit 614.

In the bio-item searching terminal apparatus 600, control is performed by the process of the input control unit 602a such that a user inputs a keyword, genome region information, and identifier information through the input unit 612, the keyword and the like are transmitted to the bio-item searching apparatus 100 by the process of the transmitting unit 602b, a candidate bio-item, a related bio-item, or a co-occurrence keyword correlated score output from the bio-item searching apparatus 100 is received by the process of the receiving output unit 602c and output to the output unit 614. In this case, FIG. 35 is a flow chart showing an example of processes of the bio-item searching terminal apparatus 600.

As shown in FIG. 35, the bio-item searching terminal apparatus 600 controls an input/output control interface unit 608 by the process of the input control unit 602a to cause a user to input user input information such as a keyword, genome region information, and identifier information through the input unit 612 (SG-1).

The bio-item searching terminal apparatus 600 controls the communication control interface unit 604 by the process of the transmitting unit 602b to transmit user input information such as a keyword to the bio-item searching apparatus 100 (SG-2).

The bio-item searching terminal apparatus 600 controls the communication control interface unit 604 by the process of the receiving output unit 602c to receive a candidate bio-item, a related bio-item, a co-occurrence keyword correlated score, or the like output from the bio-item searching apparatus 100 (SG-3).

The bio-item searching terminal apparatus 600 controls the input/output control interface unit 608 based on a corresponding correlation score or the like to output the candidate bio-item or the related bio-item to the input unit 612 (SG-4). This is another embodiment in which the present invention is applied to the client terminal (bio-item searching terminal apparatus 600).

Of each of the processes explained in the embodiment, all or some processes explained to be automatically performed may be manually performed. Alternatively, all or some processes explained to be manually performed can also be automatically performed by a known method.

In addition, the procedures, the control procedures, the specific names, the information including parameters such as registered data and searching conditions, the screens, and the database configurations which are described in the literatures or the drawings can be arbitrarily changed unless otherwise noted.

With respect to the bio-item searching apparatus 100, the constituent elements shown in the drawings are functionally schematic. The constituent elements need not be always physically arranged as shown in the drawings.

For example, all or some processing functions of the devices in the bio-item searching apparatus 100, in particular, processing functions performed by the control unit 102 can be realized by a CPU (Central Processing Unit) and a program interpreted and executed by the CPU or can also be realized by hardware realized by a wired logic. The program is recorded on a recording medium (will be described later) and mechanically read by the bio-item searching apparatus 100 as needed. More specifically, on the storage unit 106 such as a ROM or an HD, a computer program which gives an instruction to the CPU in cooperation with an OS (Operating System) to perform various process is recorded. The computer program is executed by being loaded on a RAM, and constitutes a control unit in cooperation with the CPU.

The computer program may be stored in an application program server connected to the bio-item searching apparatus 100 through an arbitrary network 300. The computer program in whole or in part can be downloaded as needed.

A program which causes a computer to execute a method according to the present invention can also be stored in a computer readable recording medium. In this case, the "recording medium" includes an arbitrary "portable physical medium" such as a flexible disk, a magnet-optical disk, a ROM, an EPROM, an EEPROM, a CD-ROM, an MO, or a DVD.

The "program" is a data processing method described in an arbitrary language or a describing method. As a format of the "program", any format such as a source code or a binary code may be used. The "program" is not always singularly constructed, and includes a program obtained by distributing and arranging a plurality of modules or libraries or a program that achieves the function in cooperation with another program typified by an OS (Operating System). In the apparatuses according to the embodiments, as a specific configuration to read a recording medium, a read procedure, an install procedure used after the reading, and the like, known configurations and procedures can be used.

Various databases or the like (all-literature set file 106a to identifier information database 106e) stored in the storage unit 106 are a memory device such as a RAM or a ROM, a fixed disk device such as a hard disk drive, and a storage unit such as a flexible disk or an optical disk and store various programs, tables, databases, Web page files used in various processes or Web site provision.

The bio-item searching apparatus 100 may be realized by connecting a known information processing apparatus such as a personal computer or a workstation and installing software (including a program, data, or the like) which causes the information processing apparatus to realize the method according to the present invention.

Furthermore, a specific configuration of distribution and integration of the devices is not limited to that shown in the drawings. All or some devices can be configured such that the devices are functionally or physically distributed and integrated in arbitrary units depending on various additions.

INDUSTRIAL APPLICABILITY

As described above in detail, according to the present invention, a bio-item searching apparatus, a bio-item searching terminal apparatus, a bio-item searching method, and a program which does not require an excessive calculation process time during searching and make it possible to display a ranking or find related item can be provided. For this reason, the present invention can be used in an information processing field which includes biology (including genetic sciences, epidemiology, and system biology), chemistry, or the like and which requires information searching.

The invention claimed is:

1. A bio-item searching apparatus that searches for a target bio-item with a keyword input by a user, comprising a processor, a storage device, and an output device, wherein
the storage device includes:
a bio-item literature set storage unit that stores one or more bio-item literature sets having a literature in which a bio-item name is described for each of a plurality of bio-items, and
an all-literature set storage unit that stores an all-literature set having all literatures included in each of the bio-item literature sets, and
the control processor includes:
a number-of-literatures acquiring unit that searches each of the bio-item literature sets with the keyword to acquire a number-of-literatures, Nh, including the keyword for each of the bio-items, and searches the all-literature set with the keyword to acquire a number-of-literatures including the keyword, Nk;
a candidate bio-item selecting unit that selects the bio-items in which the number-of-literatures Nh is 1 or larger as candidate bio-items;
a table creating unit that creates, for each of the candidate bio-items, a number-of-literatures table constituted by
a) the number-of-literatures Nh,
b) a number-of-literatures each not including the keyword and including the bio-item name, the number-of-literatures in the bio-item literature set of the bio-item minus Nh;
c) a number-of-literatures each including the keyword and not including the bio-item name, Nk−Nh, and
d) a number-of-literatures each not including the keyword and not including the bio-item, the total number-of-literatures in the all-literature set minus the number-of-literatures in the bio-item literature set minus Nk+Nh;
a correlation score calculating unit that calculates a correlation score between the bio-item and the keyword based on a statistical calculation by using the number-of-literatures table for each of the candidate bio-items; and
an output unit that outputs the candidate bio-items to the output device based on the correlation score calculated by the correlation score calculating unit.

2. The bio-item searching apparatus according to claim 1, wherein
the storage device further includes:
a bio-item relation database that stores two of the bio-items arbitrarily and a co-occurrence correlation score between the two bio-items in association with each other,
the processor further includes:
a related bio-item extracting unit that extracts a bio-item having correlation with the candidate bio-item as a related bio-item based on the co-occurrence correlation score stored in the bio-item relation database; and
an integrated correlation score calculating unit that calculates an integrated correlation score between the related bio-item and the keyword by integrating the correlation score of the candidate bio-item with the co-occurrence correlation score, and
the output unit
outputs the related bio-item to the output device based on the integrated correlation score calculated by the integrated correlation score calculating unit.

3. The bio-item searching apparatus according to claim 2, wherein
the processor includes:
a co-occurrence correlation score calculating unit that calculates, for each of the two arbitrary bio-items, the co-occurrence correlation score based on the statistical calculation by using a number-of-co-occurrence-literatures table constituted by at least one of
i) a number-of-literatures each including the one bio-item name and including an other bio-item name,
j) a number-of-literatures each not including the one bio-item name and including the other bio-item name,
k) a number-of-literatures each including the one bio-item name and including the other bio-item name, and
m) a number-of-literatures each not including the one bio-item name and not including the other bio-item name, which are acquired by searching the bio-item literature set of the one bio-item with the other bio-item name, and
a bio-item relation database creating unit that stores the co-occurrence correlation score calculated by the co-occurrence correlation score calculating unit in the bio-item relation database in association with the two bio-items.

4. The bio-item searching apparatus according to claim 2, wherein
the integrated correlation score calculating unit
integrates the integrated correlation score based on the following numerical expression 1, 1-1 or 1-2, $$P=1-(1-P1)(1-P2) \quad \text{(Numerical Expression 1)},$$

$$P=P1+P2 \quad \text{(Numerical Expression 1-1)},$$

$$\mathrm{Log}(P)=\mathrm{Max}\{\mathrm{Log}(P1),\mathrm{Log}(P2)\} \quad \text{(Numerical Expression 1-2)},$$

where P is the integrated correlation score, P1 is the correlation score of the candidate bio-item, P2 is the co-occurrence correlation score, and Max {A,B} is a function of selecting a not smaller one of A and B.

5. The bio-item searching apparatus according to claim 2, wherein
the storage device further includes:
a position information database that stores genome position information representing a position on a genome chromosome corresponding to the bio-item in association with each other for each of the bio-items; and
a region information storage unit that stores genome region information input by the user and indicating a genome region including a position on the genome chromosome corresponding to the target bio-item, and
the processor further includes:
a genome region determining unit that determines whether the position based on the genome position information corresponding to the candidate bio-item or the related bio-item, stored in the position information database is included in the genome region of the genome region information, and performs control to output the candidate bio-item or the related bio-item when it is determined that the position is included in the genome region.

6. The bio-item searching apparatus according to claim 2, wherein
the storage device further includes:
an identifier information database that stores identifier information indicating an identifier corresponding to the bio-item in association with the bio-item for each of the bio-items; and a target bio-item identifier storage unit that stores the one piece of identifier information or the pieces of identifier information input by the user and corresponding to the target bio-item, and the processor further includes:

an identifier determining unit that determines whether the identifier stored in the identifier information database and based on the identifier information of the bio-item is included in the one identifier or the plurality of identifiers of the identifier information stored in the target bio-item identifier storage unit for the candidate bio-item or the related bio-item, and performs control to output the candidate bio-item or the related bio-item when it is determined that the identifier is included in the one identifier or the plurality of identifiers.

7. The bio-item searching apparatus according to claim 3, wherein the number-of-literatures acquiring unit searches, for two of the candidate bio-items arbitrarily, the bio-item literature set of the one candidate bio-item to acquire a number Ns of literatures each including the other bio-item name and including the keyword, the table creating unit creates a three-dimensional number-of-literatures table based on the number-of-literatures Ns, the number-of-literatures table related to the two candidate bio-items, and the number-of-co-occurrence-literatures table related to the two candidate bio-items, the correlation score calculating unit includes a co-occurrence keyword correlation score calculating unit that calculates a co-occurrence keyword correlation score among the two candidate bio-items and the keyword based on the statistical calculation by using the three-dimensional number-of-literatures table, and the output unit outputs the co-occurrence keyword correlation score calculated by the co-occurrence keyword correlation score calculating unit to the output device in association with the two candidate bio-items.

8. The bio-item searching apparatus according to claim 7, wherein the co-occurrence keyword correlation score calculating unit by using the three-dimensional number-of-literatures table, calculates a correlation score of the two candidate bio-items when the keyword is included as a keyword-included correlation score, calculates a correlation score of the two candidate bio-items when the keyword is not included as a keyword-not-included correlation score, and calculates any one of both the keyword-included correlation score and the keyword-not-included correlation score and a comparison result therebetween or both as the co-occurrence keyword correlation score.

9. The bio-item searching apparatus according to claim 1, wherein the statistical calculation calculates the correlation score based on a test.

10. The bio-item searching apparatus according to claim 1, wherein the statistical calculation uses a Fisher's exact test, a chi-square test, or a Bayes conditional probability.

11. The bio-item searching apparatus according to claim 1, wherein the output unit includes:

a searching result order output unit that ranks the candidate bio-item or a related bio-item to be output to the output device, based on the correlation score, the co-occurrence keyword correlation score, or a integrated correlation score.

12. The bio-item searching apparatus according to claim 1, wherein the bio-item name includes a concept word.

13. A bio-item searching terminal apparatus comprising a control unit, an input unit, and an output unit connected to the bio-item searching apparatus according to claim 1, wherein the control unit includes:

an input control unit that performs control to cause a user to input any one, two or all of the keyword, genome region information and identifier information through the input unit;

a transmitting unit that transmits any one, two, or all of the keyword, the genome region information and the identifier information input by control of the input control unit to the bio-item searching apparatus; and a receiving output unit that receives and outputs the candidate bio-item, the related bio-item, or a co-occurrence keyword correlation score based on at least the keyword transmitted by the transmitting unit and output from the bio-item searching apparatus, to the output unit.

14. A bio-item searching method for searching for a target bio-item with a keyword input by a user, executed by a bio-item searching apparatus comprising a control device, a storage device, and an output device, wherein the storage device includes:

a bio-item literature set storage unit that stores one or more bio-item literature sets having a literature in which a bio-item name is described for each of a plurality of bio-items, and an all-literature set storage unit that stores an all-literature set having all the literatures included in each of the bio-item literature sets, and the bio-item searching method includes:

searching each of the bio-item literature sets with the keyword to acquire a number-of-literatures, Nh, including the keyword for each of the bio-items and searching the all-literature set with the keyword to acquire the number-of-literatures including the keyword, Nk;

selecting the bio-items in which the number-of-literatures Nh is 1 or larger as candidate bio-items;

creating, for each of the candidate bio-items, a number-of-literatures table constituted by a) the number-of-literatures Nh, b) a number-of-literatures each not including the keyword and including the bio-item name, the number-of-literatures in the bio-item literature set of the bio-item minus Nh;

c) a number-of-literatures each including the keyword and not including the bio-item name, Nk−Nh, and d) a number-of-literatures each not including the keyword and not including the bio-item, the total number-of-literatures in the all-literature set minus the number-of-literatures in the bio-item literature set minus Nk+Nh;

calculating a correlation score between the bio-item and the keyword based on a statistical calculation by using the number-of-literatures table for each of the candidate bio-items; and outputting the candidate bio-items to the output device based on the correlation score calculated at the calculating, that are executed by the control device.

15. A non-transitory computer-readable recording medium that stores therein a computer program that makes a bio-item searching apparatus execute a method for searching for a target bio-item with a keyword input by a user, wherein
- the bio-item searching apparatus comprises a control device, a storage device, and an output device,
- the storage device includes:
  - a bio-item literature set storage unit that stores one or more bio-item literature sets having a literature in which a bio-item name is described for each of a plurality of bio-items, and
  - an all-literature set storage unit that stores an all-literature set having all the literatures included in each of the bio-item literature sets, and
- the method includes:
  - searching each of the bio-item literature sets with the keyword to acquire a number-of-literatures, Nh, including the keyword for each of the bio-items, and
searching the all-literature set with the keyword to acquire the number-of-literatures including the keyword, Nk;
  - selecting the bio-items in which the number-of-literatures Nh is 1 or larger as candidate bio-items;
  - creating, for each of the candidate bio-items, a number-of-literatures table constituted by
    a) the number-of-literatures Nh,
    b) a number-of-literatures each not including the keyword and including the bio-item name, the number-of-literatures in the bio-item literature set of the bio-item minus Nh;
    c) a number-of-literatures each including the keyword and not including the bio-item name, Nk−Nh, and
    d) a number-of-literatures each not including the keyword and not including the bio-item, the total number-of-literatures in the all-literature set minus the number-of-literatures in the bio-item literature set minus Nk+Nh;
  - calculating a correlation score between the bio-item and the keyword based on a statistical calculation by using the number-of-literatures table for each of the candidate bio-items; and
  - outputting the candidate bio-items to the output device based on the correlation score calculated at the calculating,
that are executed by the control device.

* * * * *